(12) United States Patent
Nitzan et al.

(10) Patent No.: US 10,960,189 B2
(45) Date of Patent: *Mar. 30, 2021

(54) SYSTEMS AND METHODS FOR TREATMENT OF FLUID OVERLOAD

(71) Applicant: White Swell Medical Ltd, Shfayim Center (IL)

(72) Inventors: Yaacov Nitzan, Hertzeliya (IL); Sagi Raz, Tel-Aviv (IL); Shani Chen, Givatayim (IL); Or Inbar, Tel-Aviv (IL)

(73) Assignee: White Swell Medical Ltd, Kibbutz Shefayim (IL)

( * ) Notice: Subject to any disclaimer, the term of this patent is extended or adjusted under 35 U.S.C. 154(b) by 530 days.

This patent is subject to a terminal disclaimer.

(21) Appl. No.: 15/799,562

(22) Filed: Oct. 31, 2017

(65) Prior Publication Data

US 2018/0126130 A1    May 10, 2018

Related U.S. Application Data

(60) Provisional application No. 62/415,684, filed on Nov. 1, 2016, provisional application No. 62/415,964, filed on Nov. 1, 2016, provisional application No. 62/445,231, filed on Jan. 11, 2017.

(51) Int. Cl.
*A61M 27/00* (2006.01)
*A61M 1/00* (2006.01)
(Continued)

(52) U.S. Cl.
CPC ..... *A61M 27/002* (2013.01); *A61B 17/12045* (2013.01); *A61B 17/12136* (2013.01);
(Continued)

(58) Field of Classification Search
CPC .................. A61M 27/002; A61M 1/00; A61M 25/10184; A61M 2025/1052;
(Continued)

(56) References Cited

U.S. PATENT DOCUMENTS 3,211,150 A    10/1965    Foderick
4,714,460 A    12/1987    Calderon
(Continued)

FOREIGN PATENT DOCUMENTS

EP    0526102 A1    2/1993
WO    89/04193 A1    5/1989
(Continued)

OTHER PUBLICATIONS

International Search Report and Written Opinion dated Apr. 12, 2018, for PCT/IB17/01488, filed Oct. 31, 2017 (11 pages).
(Continued)

*Primary Examiner* — Leslie R Deak
(74) *Attorney, Agent, or Firm* — Brown Rudnick LLP; Adam M. Schoen

(57) ABSTRACT

Various systems and methods are provided for reducing pressure at an outflow of a duct, such as the thoracic duct or the lymphatic duct, for example, the right lymphatic duct. A catheter system can be configured to be at least partially implanted within a vein of a patient in the vicinity of an outflow port of a duct of the lymphatic system. The catheter system includes first and second selectively deployable restriction members each configured to be activated to at least partially occlude the vein within which the catheter is implanted and to thus restrict fluid within a portion of the vein. The catheter system includes an impeller configured to be driven by a motor to induce a low pressure zone between the restriction members by causing blood to be pumped through the catheter when the restriction members occlude the vein.

15 Claims, 29 Drawing Sheets

(51) Int. Cl.
*A61B 17/12* (2006.01)
*A61F 2/06* (2013.01)
*A61M 25/10* (2013.01)
*A61F 2/00* (2006.01)

(52) U.S. Cl.
CPC .................. *A61F 2/00* (2013.01); *A61F 2/06* (2013.01); *A61M 1/00* (2013.01); *A61M 25/10184* (2013.11); *A61F 2002/068* (2013.01); *A61M 2025/1015* (2013.01); *A61M 2025/1022* (2013.01); *A61M 2025/1052* (2013.01); *A61M 2025/1097* (2013.01); *A61M 2202/0405* (2013.01); *A61M 2205/3317* (2013.01); *A61M 2205/3344* (2013.01); *A61M 2205/8206* (2013.01); *A61M 2210/12* (2013.01); *A61M 2230/30* (2013.01)

(58) Field of Classification Search
CPC .. A61M 1/125; A61M 1/1018; A61M 1/1012; A61M 1/1034; A61M 1/1029; A61B 17/12136; A61B 17/12045; A61B 5/418; A61F 2/06; A61F 2/00
See application file for complete search history.

(56) References Cited

U.S. PATENT DOCUMENTS

| | | | |
|---|---|---|---|
| 4,822,341 A | 4/1989 | Colone | |
| 4,957,484 A | 9/1990 | Murtfeldt | |
| 5,005,564 A | 4/1991 | Grundei et al. | |
| 5,069,662 A | 12/1991 | Bodden | |
| 5,366,504 A | 11/1994 | Andersen et al. | |
| 5,391,143 A | 2/1995 | Kensey | |
| 5,484,412 A | 1/1996 | Pierpont | |
| 5,509,897 A | 4/1996 | Twardowski et al. | |
| 5,554,119 A | 9/1996 | Harrison et al. | |
| 5,558,642 A | 9/1996 | Schweich, Jr. et al. | |
| 5,716,340 A | 2/1998 | Schweich, Jr. et al. | |
| 5,817,046 A | 10/1998 | Glickman | |
| 5,836,912 A | 11/1998 | Kusleika | |
| 5,893,841 A | 4/1999 | Glickman | |
| 5,897,533 A | 4/1999 | Glickman | |
| 5,908,407 A | 6/1999 | Frazee et al. | |
| 5,919,163 A | 7/1999 | Glickman | |
| 6,042,569 A | 3/2000 | Finch, Jr. et al. | |
| 6,139,517 A | 10/2000 | Macoviak et al. | |
| 6,152,945 A | 11/2000 | Bachinski et al. | |
| 6,165,196 A | 12/2000 | Stack et al. | |
| 6,183,492 B1 | 2/2001 | Hart et al. | |
| 6,248,091 B1 | 6/2001 | Voelker | |
| 6,254,563 B1 | 7/2001 | Macoviak et al. | |
| 6,503,224 B1 | 1/2003 | Forman et al. | |
| 6,524,323 B1 | 2/2003 | Nash et al. | |
| 6,555,057 B1 | 4/2003 | Bendera | |
| 6,616,623 B1 | 9/2003 | Kutushov | |
| 6,635,068 B1 | 10/2003 | Dubrul et al. | |
| 6,699,231 B1 | 3/2004 | Sterman et al. | |
| 6,878,140 B2 | 4/2005 | Barbut | |
| 6,936,057 B1 | 8/2005 | Nobles | |
| 7,022,097 B2 | 4/2006 | Glickman | |
| 7,195,608 B2 | 3/2007 | Burnett | |
| 7,645,259 B2 | 1/2010 | Goldman | |
| 7,766,892 B2 | 8/2010 | Keren et al. | |
| 7,780,628 B1 | 8/2010 | Keren et al. | |
| 8,126,538 B2 | 2/2012 | Shuros et al. | |
| 8,216,122 B2 | 7/2012 | Kung | |
| 8,480,555 B2 | 7/2013 | Kung | |
| 8,679,057 B2 | 3/2014 | Fulton, III et al. | |
| 9,179,921 B1 | 11/2015 | Morris | |
| 9,405,942 B2 | 8/2016 | Liao et al. | |
| 9,421,316 B2 | 8/2016 | Leeflang et al. | |
| 9,433,713 B2 | 9/2016 | Corbett et al. | |
| 9,486,566 B2 | 11/2016 | Siess | |
| 9,533,054 B2 | 1/2017 | Yan et al. | |
| 9,533,084 B2 | 1/2017 | Siess et al. | |
| 9,642,991 B2 | 5/2017 | Eversull et al. | |
| 9,669,142 B2 | 6/2017 | Spanier et al. | |
| 9,669,144 B2 | 6/2017 | Spanier et al. | |
| 9,675,739 B2 | 6/2017 | Tanner et al. | |
| 9,682,223 B2 | 6/2017 | Callaghan et al. | |
| 9,750,861 B2 | 9/2017 | Hastie et al. | |
| 10,226,604 B2* | 3/2019 | Nitzan .................... | A61M 1/00 |
| 2003/0093109 A1 | 5/2003 | Mauch | |
| 2004/0006306 A1 | 1/2004 | Evans et al. | |
| 2004/0064091 A1 | 4/2004 | Keren et al. | |
| 2004/0147871 A1 | 7/2004 | Burnett | |
| 2004/0210296 A1 | 10/2004 | Schmitt et al. | |
| 2004/0230181 A1 | 11/2004 | Cawood | |
| 2005/0228474 A1 | 10/2005 | Laguna | |
| 2005/0251180 A1 | 11/2005 | Burton et al. | |
| 2006/0100658 A1 | 5/2006 | Obana et al. | |
| 2007/0055299 A1 | 3/2007 | Ishimaru et al. | |
| 2007/0282303 A1 | 12/2007 | Nash et al. | |
| 2007/0282382 A1 | 12/2007 | Shuros et al. | |
| 2008/0009719 A1 | 1/2008 | Shuros et al. | |
| 2008/0015628 A1 | 1/2008 | Dubrul et al. | |
| 2008/0097412 A1 | 4/2008 | Shuros et al. | |
| 2008/0103573 A1 | 5/2008 | Gerber | |
| 2008/0140000 A1 | 6/2008 | Shuros et al. | |
| 2009/0018526 A1 | 1/2009 | Power et al. | |
| 2009/0112184 A1 | 4/2009 | Fierens et al. | |
| 2009/0131785 A1 | 5/2009 | Lee et al. | |
| 2010/0168649 A1 | 7/2010 | Schwartz et al. | |
| 2010/0179389 A1 | 7/2010 | Moroney, III et al. | |
| 2011/0004046 A1 | 1/2011 | Campbell et al. | |
| 2011/0092955 A1 | 4/2011 | Purdy et al. | |
| 2011/0276023 A1 | 11/2011 | Leeflang et al. | |
| 2011/0282274 A1 | 11/2011 | Fulton, III | |
| 2012/0029466 A1 | 2/2012 | Callaghan et al. | |
| 2012/0157913 A1 | 6/2012 | Aziz et al. | |
| 2012/0259215 A1 | 10/2012 | Gerrans et al. | |
| 2013/0096494 A1 | 4/2013 | Kassab | |
| 2013/0138041 A1 | 5/2013 | Smisson, III et al. | |
| 2013/0237954 A1 | 9/2013 | Shuros et al. | |
| 2013/0245607 A1 | 9/2013 | Eversull et al. | |
| 2013/0317535 A1 | 11/2013 | Demmy | |
| 2013/0338559 A1 | 12/2013 | Franano et al. | |
| 2014/0010686 A1 | 1/2014 | Tanner et al. | |
| 2014/0128659 A1 | 5/2014 | Heuring et al. | |
| 2014/0142616 A1 | 5/2014 | Smith | |
| 2014/0155815 A1 | 6/2014 | Fulton, III et al. | |
| 2014/0220617 A1 | 8/2014 | Yung et al. | |
| 2014/0243790 A1 | 8/2014 | Callaghan et al. | |
| 2014/0303461 A1 | 10/2014 | Callaghan et al. | |
| 2015/0157777 A1 | 6/2015 | Tuval et al. | |
| 2015/0164662 A1 | 6/2015 | Tuval | |
| 2015/0283360 A1 | 10/2015 | Kelly | |
| 2015/0343136 A1 | 12/2015 | Nitzan et al. | |
| 2015/0343186 A1 | 12/2015 | Nitzan et al. | |
| 2016/0022890 A1 | 1/2016 | Schwammenthal et al. | |
| 2016/0051741 A1 | 2/2016 | Schwammenthal et al. | |
| 2016/0129266 A1 | 5/2016 | Schmidt | |
| 2016/0169630 A1 | 6/2016 | Augustine et al. | |
| 2016/0331378 A1* | 11/2016 | Nitzan ............. | A61B 17/12036 |
| 2017/0014563 A1 | 1/2017 | Khir | |
| 2017/0197021 A1 | 7/2017 | Nitzan et al. | |
| 2018/0126130 A1 | 5/2018 | Nitzan et al. | |

FOREIGN PATENT DOCUMENTS

| | | |
|---|---|---|
| WO | 01/013983 A2 | 3/2001 |
| WO | 2012/135834 A2 | 10/2012 |
| WO | 2014/141284 A2 | 9/2014 |
| WO | 2017/087556 A1 | 5/2017 |

OTHER PUBLICATIONS

International Search Report and Written Opinion dated Jun. 25, 2018, for PCT/IB18/00263, filed Mar. 1, 2018 (10 pages).

(56) References Cited

OTHER PUBLICATIONS

International Search Report and Written Opinion dated Oct. 30, 2018, for PCT/IB18/000364, filed Mar. 19, 2018 (9 pages).

* cited by examiner

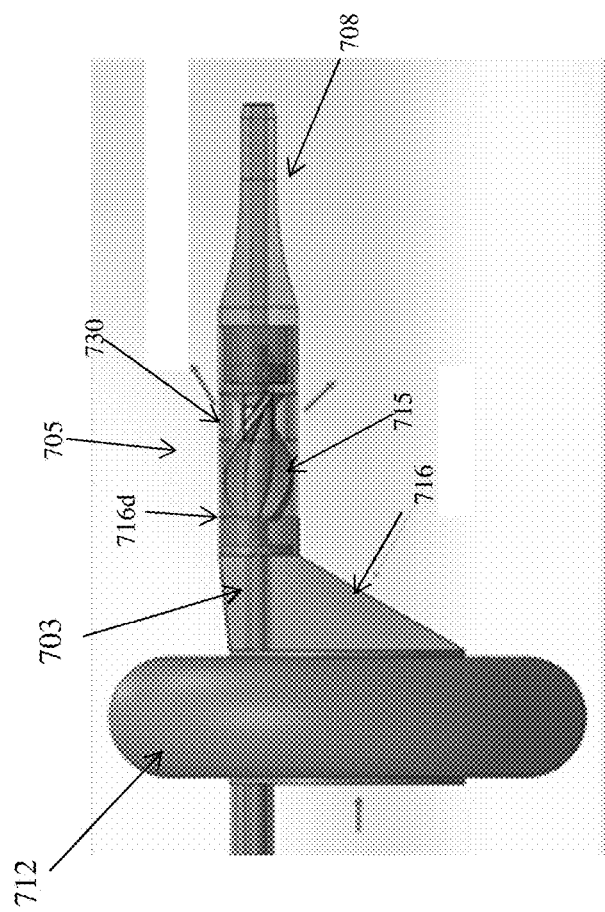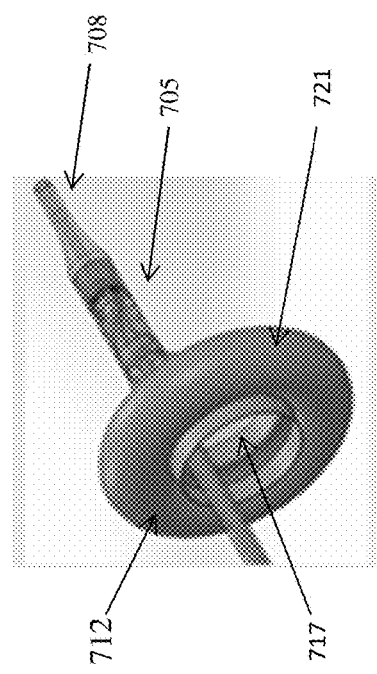
FIG. 9A
FIG. 9B

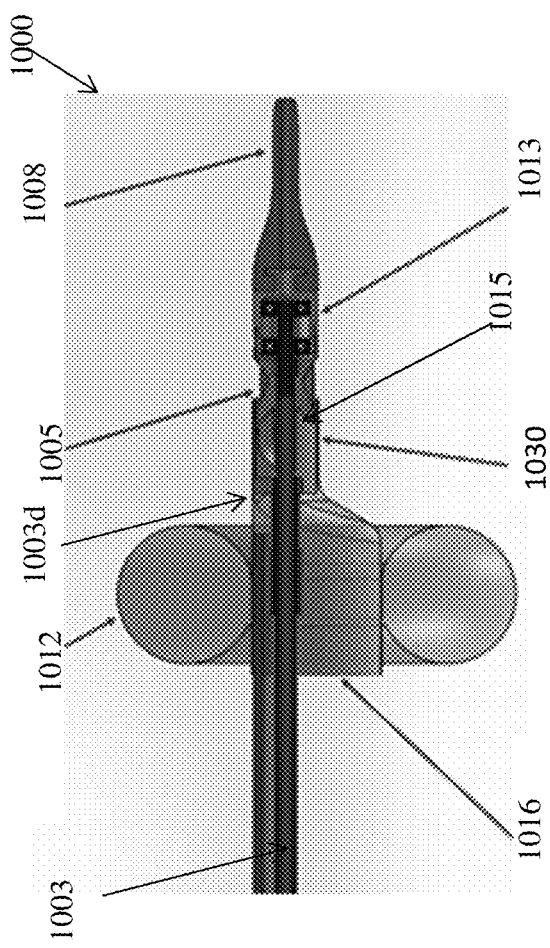
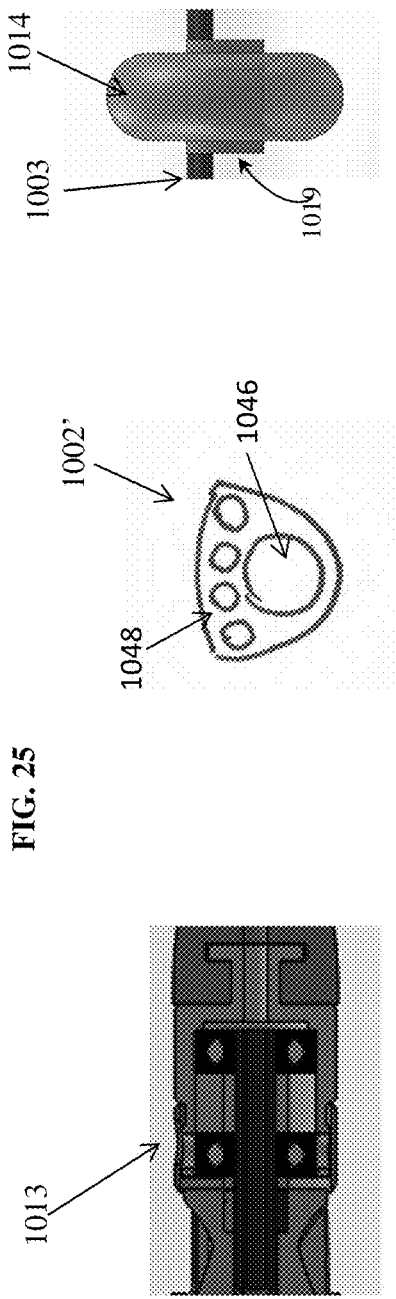
FIG. 25
FIG. 26A
FIG. 26B
FIG. 26C

SYSTEMS AND METHODS FOR TREATMENT OF FLUID OVERLOAD

CROSS REFERENCE TO RELATED APPLICATIONS

The present application claims priority to U.S. Patent Application No. 62/415,684 entitled "Systems And Methods For Treatment of Pulmonary Edema" filed Nov. 1, 2016, U.S. Patent Application No. 62/415,964 entitled "Systems and Methods for Treatment of Edema" filed Nov. 1, 2016, and U.S. Patent Application No. 62/445,231 entitled "Catheter with Impeller for Treatment of Edema" filed Jan. 11, 2017, which are hereby incorporated by reference in their entireties.

FIELD

The present disclosure relates generally to systems and methods for fluid overload relief and, in particular, for treatment of edema.

BACKGROUND

The lymphatic system is part of the circulatory system in conjunction with the arterial and venous systems. A primary function of the lymphatic system is to drain excessive interstitial fluid back into the venous system at two main locations: the thoracic duct and the lymphatic duct (the right lymphatic duct), which drain into the left and right bifurcation of the internal Jugular and subclavian veins, respectively.

Under normal circulatory conditions of the arterial and venous systems, the interstitial fluid volume balance is maintained and the lymph fluid is cleared back through the lymphatic system. In pathological conditions such as acute cardiogenic fluid overload, acutely decompensated heart failure and chronic heart failure, the capillary hydrostatic pressure and the venous pulmonary pressure can become elevated and fluid flows excessively out of the blood vessels and into the interstitial and alveolar spaces. The pressure gradient between the initial lymphatics and at the outflow of the thoracic duct and a lymphatic duct is reduced, and the lymphatic system cannot clear the additional fluid which accumulates in the air spaces of the lungs. This is a life threatening condition, as gas exchange is impaired to the extent that it may lead to respiratory failure.

Current treatment methods require extended hospitalization and treatment with loop diuretics and/or vasodilators. Oftentimes patients must also receive supplemental oxygen or, in more extreme cases, require mechanical ventilation. Many of these treatment methods are less than ideal because the edema is not always alleviated rapidly enough and for many patients renal function is adversely affected. A significant percentage of patients do not respond to this treatment and a significant percentage must be readmitted to a hospital within thirty days.

A significant problem with current treatment protocol is that it is based on the need to reduce intravascular blood pressure to move interstitial and lymphatic fluid back into the vasculature. The reduction of intravascular blood pressure may lead to hypotension and may activate the Renin Angiotenesin Aldesterone System, which may lead back to an increase in blood pressure or to worsening of renal function. Eventually, this cycle leads to diuretic resistance and the worsening of renal function in almost 30% of admitted patients.

Accordingly, there remains a need for improved methods and devices for systems and methods for treating fluid overload.

SUMMARY

In one aspect, a medical system for treating fluid overload is provided that in some embodiments includes a catheter configured for at least partial placement within a vein of a patient, and a motor. The catheter includes an indwelling catheter tube having a lumen extending therethrough, the lumen configured to receive a drive shaft having a distal end thereof operatively coupled to an impeller. The catheter also includes a first selectively deployable restriction member adjacent to the impeller, the first selectively deployable restriction member disposed around a first portion of the catheter shaft, and a second selectively deployable restriction member proximal to the first restriction member, the second selectively deployable restriction member disposed around a second portion of the catheter tube. The motor is configured to rotate the drive shaft and thereby rotate the impeller coupled to the drive shaft.

The system can vary in numerous ways. For example, the impeller can be disposed distally to the first restriction member. As another example, the system can further include a flow regulation component disposed proximally to the second restriction member and configured to direct fluid from an upstream side of the second restriction member to a downstream side of the second restriction member, the flow regulation component having at least one opening configured to allow fluid therethrough. The flow regulation component can be operatively coupled to the second restriction member. The flow regulation component can be configured to direct fluid through a lumen of the second restriction member.

In some embodiments, the system further includes a controller configured to control operation of the motor based on measurements of fluid pressure acquired by at least one pressure sensor located between the first and second restrictors.

In some embodiments, the first and second restriction members each include a selectively expandable element configured to be expanded radially. In some embodiments, the catheter tube has at least one inflation lumen configured to deliver a fluid or gas to activate the first and second restriction members.

The first restriction member can have a first inner lumen and the second restriction member can have a second inner lumen, the first and second inner lumens allow fluid to pass therethrough. In some embodiments, the first inner lumen of the first restriction member has a diameter that is greater than a diameter of the second inner lumen of the second restriction member. In some embodiments, an inner wall of the first restriction member defining the first inner lumen of the first restriction member has a shaft holder coupled thereto, the shaft holder being configured to receive the catheter tube thereto so as to maintain a position of the catheter tube. In some embodiments, the system further includes a membrane extending between the first restriction member and an impeller housing configured to encompass the impeller, the membrane being coupled to the first restriction member and defining a tunnel therethrough. The membrane can have various configurations. For example, in some embodiments, the membrane can be generally distally tapered.

The impeller housing can also have various configurations. For example, in some embodiments, the impeller housing includes at least one opening at a distal end thereof such that fluid passing through the impeller housing from a proximal end thereof towards the distal end thereof can exit the impeller housing through the at least one opening.

In another aspect, a catheter system for treating fluid overload is provided that in some embodiments includes a catheter configured for at least partial placement within a vein of a patient, the catheter including an indwelling catheter tube having a lumen extending therethrough, the lumen configured to receive a drive shaft having a distal end thereof operatively coupled to an impeller, a first selectively deployable restriction member adjacent to the impeller and disposed around the catheter tube, a second selectively deployable restriction member proximal to the first restriction member and disposed around the catheter tube. The catheter also includes a fluid flow passage defined by a second inner lumen of the second restriction member, a first inner lumen of the first restriction member, an impeller housing having the impeller in a tunnel thereof, and a membrane extending between the first restriction member and the impeller housing.

The system can vary in numerous ways. For example, the system can further include a motor operatively coupled to the drive shaft and configured to rotate the drive shaft and thereby rotate the impeller coupled to the drive shaft. As another example, the system can further include an atraumatic tip extending distally from the impeller housing.

In a further aspect, a method for treating fluid overload is provided that in some embodiments includes implanting a catheter within a vein of a patient, the catheter extending from a first position at one side of an outflow port of a duct to a second position at another side of the outflow port; creating a first restriction within the vein proximal to a distal region of the catheter; creating a second restriction within the vein proximal to a first restriction; and activating an impeller of the catheter so as to define a localized low pressure zone between the second and first restrictions and adjacent to the outflow port of the duct, the low pressure zone being created by causing fluid to pass from a proximal side of the second restriction to a distal side of the second restriction and from a proximal side of the first restriction to a distal side of the first restriction.

The method can vary in numerous ways. For example, creating the first restriction can include deploying a first selectively expandable restrictor and creating the second restriction can include deploying a second selectively expandable restrictor such that the fluid passes from the proximal side of the second restriction to the distal side of the first restriction by passing through inner lumens of the first and second restrictors and towards the impeller. As another example, the vein can be at least one of an internal jugular vein and a subclavian vein. As a further example, the duct includes one of a thoracic or a right lymphatic duct.

In some embodiments, various systems and methods are provided for reducing pressure at an outflow of a duct such as the thoracic duct or the lymphatic duct, for example, the right lymphatic duct. An indwelling catheter can be configured to be at least partially implanted within a vein of a patient in the vicinity of or within an outflow port of a duct of the lymphatic system. The catheter can include first and/or second restrictors each configured to at least partially occlude the vein within which the catheter is implanted and to thus restrict fluid within the vein when the restrictors are activated. The catheter can include a pump including an impeller disposed within a catheter shaft. The impeller can be positioned at various locations with respect to the first and second restrictors.

In one aspect, a system for treating edema is provided that in some embodiments includes an indwelling catheter configured for at least partial placement within a vein of a patient, the indwelling catheter having a catheter shaft, the catheter shaft having one or more inlet openings, a first selectively deployable restriction member, a second selectively deployable restriction member, and a lumen extending through the catheter shaft, the lumen being in fluid communication with the first and the second restriction members, wherein the first restriction member is disposed at a proximal end of the lumen and the second restriction member is disposed at a distal end of the lumen. The system also includes a pump configured to create a pressure differential to withdraw fluid from the inlet opening to withdraw a fluid within the vein from venous circulation and to return the fluid to venous circulation through the catheter system, a motor configured to cause the pump to operate, and a controller configured to control operation of the motor.

The system can vary in a number of ways. For example, the system can include an impeller associated with the catheter shaft. The impeller can be positioned proximally to the first restriction member, distally to the second restriction member, or between the first and second restriction members. As yet another example, the lumen can be expandable. As a further example, the lumen can include an expandable segment extending between an inlet opening of the lumen and the impeller In some embodiments, the controller can operate using measurements obtained by at least one sensor, the measurements including motor current and voltage consumption. In some embodiments, the first and second restrictors each include a balloon.

In some embodiments, a medical system is provided that includes a catheter shaft configured to be positioned within a vein of a patient, a first selectively deployable restrictor coupled to the catheter shaft and configured to be positioned within the vein and a second selectively deployable restrictor coupled to the catheter shaft at a location distal to the first restrictor such that a distance spans between the first and second restrictors, the second restrictor being configured to be positioned within the vein. The medical system also includes at least one inlet opening formed through a sidewall of the catheter shaft at a location between the first and second restrictors, and a pump configured to facilitate suction of fluid into the catheter shaft through the at least one inlet opening.

The medical system can vary in a number of ways. For example, the first and second restrictors can each include a balloon. As another example, the medical system can further include at least one inflation lumen extending along the catheter shaft, the at least one inflation lumen being in fluid communication with the first and second restrictors. The at least one inflation lumen can include a single lumen in fluid communication with both of the first and second restrictors. As yet another example, the first restrictor can be movable between an activated configuration in which the first restrictor has a first diameter and a relaxed configuration in which the first restrictor has a second diameter that is less than the first diameter, and the second restrictor is movable between an activated configuration in which the second restrictor has a third diameter and a relaxed configuration in which the second restrictor has a fourth diameter that is less than the third diameter.

In some embodiments, the system further includes an impeller associated with the catheter shaft. The impeller can be disposed proximally to the first restrictor, distally to the second restrictor, or between the first and second restrictors.

In some embodiments, the impeller is disposed proximally to the first restrictor, and the catheter shaft includes an inflation lumen, the inflation lumen comprising an expandable segment disposed between the at least one inlet opening and the impeller.

In some embodiments, the pump is configured to be positioned within the vein. In some embodiments, the system further includes a controller configured to actuate the pump. The controller can be configured to actuate the pump in response to user operation of a control external to the body of the patient. In some embodiments, the system further includes a pressure sensor configured to be implanted in the body of the patient, the controller being configured to actuate the pump in response to a pressure measured by the pressure sensor being different (e.g., smaller or greater) than a predefined threshold.

In some embodiments, the system further includes a pressure sensor configured to be implanted in the body of the patient, the controller being configured to control a speed of operation of the pump depending on a pressure measured by the pressure sensor. In some embodiments, the vein includes an internal jugular vein, a subclavian vein, an innominate vein or an external jugular vein.

In some embodiments, a medical method is provided that includes implanting the catheter shaft at least at least partially within a vein of a patient such that the first restrictor is positioned upstream of an outflow port of a duct of the patient's lymphatic system and such that the second restrictor is positioned downstream of the outflow port of the duct.

The medical method can vary in many ways. For example, the method can further include activating the first restrictor such that the first restrictor occludes the vein at a first occlusion site, and activating the second restrictor such that the second restrictor occludes the vein at a second occlusion site. As another example, the method can further include activating the first restrictor by inflating the first restrictor, and activating the second restrictor by inflating the second restrictor. In some embodiments, activating the first restrictor includes radially expanding the first restrictor, and activating the second restrictor includes radially expanding the second restrictor. In some embodiments, the method further includes actuating the pump, thereby creating a low pressure zone between the first and second restrictors. The duct can include a thoracic duct or a lymphatic duct (e.g., a right lymphatic duct), and the vein can include both right and left internal jugular veins, a subclavian vein, an innominate vein, or an external jugular vein.

In another aspect, a medical system is provided that in some embodiments includes a catheter shaft configured to be positioned within a vein of a patient, at least one restrictor, and a pump. The at least one restrictor is coupled to the catheter shaft and is configured to be positioned within the vein, the at least one restrictor being movable between an activated configuration in which the at least one restrictor has a first diameter and a relaxed configuration in which the at least one restrictor has a second diameter that is less than the first diameter, the at least one restrictor being configured to occlude fluid flow through the vein when the at least one restrictor is in the activated configuration within the vein. The pump is configured to pump fluid through the catheter shaft regardless of whether the at least one restrictor is in the activated configuration or the relaxed configuration.

The medical system can vary in many ways. For example, the at least one restrictor can include a single restrictor. As another example, the at least one restrictor can include a balloon. As yet another example, the system can include at least one inflation lumen extending along the catheter shaft, the at least one inflation lumen being in fluid communication with the at least one restrictor. As a further example, the system can include an impeller associated with the catheter shaft.

In some embodiments, the pump is configured to be positioned within the vein. In some embodiments, the system further includes a controller configured to actuate the pump. The controller can be configured to actuate the pump in response to user operation of a control external to the body of the patient.

In some embodiments, the system can further include a pressure sensor configured to be implanted in the body of the patient, the controller being configured to actuate the pump in response to a pressure measured by the pressure sensor exceeding a predefined threshold. The vein can include an internal jugular vein or a subclavian vein.

In some embodiments, a medical method is provided that includes implanting the catheter shaft at least at least partially within a vein of a patient such that the at least one restrictor is positioned upstream of an outflow port of a duct of the patient's lymphatic system.

The medical method can vary in many ways. For example, the method can further include activating the at least one restrictor such that the at least one restrictor occludes the vein. As another example, the method can further include activating the at least one restrictor by inflating the at least one restrictor. As a further example, the method can include activating the at least one restrictor by radially expanding the at least one restrictor. In some embodiments, the method further includes actuating the pump, thereby creating a low pressure zone adjacent the duct.

Various systems and methods are provided for reducing pressure at an outflow of a duct such as the thoracic duct or the lymphatic duct (e.g., the right lymphatic duct). An indwelling catheter can be configured to be at least partially implanted within a vein of a patient in the vicinity of or inside an outflow port of a duct of the lymphatic system.

In some aspects, a system for treating edema is provided that in some embodiments includes an indwelling catheter configured for placement within a vein of a patient. The indwelling catheter includes a drive shaft having a lumen extending therethrough, wherein a distal portion of the drive shaft is operatively coupled to an impeller. The indwelling catheter also includes a first selectively deployable restriction member adjacent and proximal to the impeller, the first restriction member having a membrane operatively coupled thereto and configured to direct fluid from an upstream side of the first restriction member to the impeller. The indwelling catheter further includes a second selectively deployable restriction member proximal to the first restriction member, the second restriction member being operatively coupled to a flow regulation component configured to direct a controlled volume of fluid from an upstream side of the second restriction member to a downstream side of the second restriction member. The system also includes a motor configured to rotate the drive shaft and the impeller.

The system can vary in a number of ways. For example, the membrane can be a conical membrane at least partially wrapped around the first restriction member. As another example, the flow regulation component can have at least one opening configured to allow fluid therethrough. As yet another example, the system can further include a controller configured to control operation of the motor. The controller can operate using measurements obtained by at least one sensor, the measurements including fluid pressure.

In some embodiments, the first and second restriction members each include a balloon. In some embodiments, the vein is an internal jugular vein or a subclavian vein. In some embodiments, the first restriction member is part of a distal assembly, and the second restriction member is part of a separate, proximal assembly.

In one aspect, a system for treatment of interstitial fluid overload, which can lead to edema, is provided that in some embodiments includes a pump configured to be implanted in a body of a patient, an inflow tube, an outflow tube, and power source. The inflow tube is fluidically coupled to an inflow port of the pump and configured to be implanted into the body of the patient so as to bring the inflow port into fluid communication with a thoracic duct or a right lymphatic duct of the patient. The outflow tube is fluidically coupled to an outflow port of the pump and configured to be implanted into the body of the patient so as to bring the outflow port into fluid communication with a vein in the body of the patient such that the pump is operative to pump fluid from the thoracic duct or the right lymphatic duct to the vein. The power source is configured to be implanted in the body of the patient and configured to provide power to the pump.

The system can vary in a number of ways. For example, the power source can include a battery. The battery can be a rechargeable battery. As another example, the pump can be configured to continuously pump the fluid from the thoracic duct to the vein.

In some embodiments, the system can further include a controller configured to activate the pump. The controller can be configured to actuate the pump in response to user operation of a control external to the body of the patient.

In some embodiments, the system can further include a pressure sensor configured to be implanted in the body of the patient, the controller being configured to actuate the pump in response to a pressure measured by the pressure sensor exceeding a predefined threshold. In some embodiments, the system can further include a pressure sensor configured to be implanted in the body of the patient, the controller being configured to control a speed of operation of the pump depending on a pressure measured by the pressure sensor.

The pump can vary in a number of ways. For example, the pump can include a pulsatile pump. As another example, the pump can be configured to pump fluid at a rate in a range of about 100 to 1000 ml/hour. As another example, the pump can be configured to pump fluid at a rate of about 300 ml/hour. As yet another example, the pump can be configured to pump fluid at a rate of about 500 ml/hour.

In another aspect, a method of treating edema is provided that in some embodiments includes implanting a pump in a body of a patient, the pump being operable to convey a bodily fluid from an inflow port of the pump to an outflow port of the pump, arranging a first tube in fluid communication with the inflow port to be in fluid communication with a thoracic duct of the patient, arranging a second tube in fluid communication with the outflow port to be in fluid communication with a vein of the patient such that the pump is operable to convey fluid from the thoracic duct to the vein, and implanting a power source configured to be implanted in the body of the patient and configured to provide power to the pump.

The method can vary in a number of ways. For example, the method can further include actuating the pump, thereby causing the pump to convey the fluid from the thoracic duct to the vein of the patient, the fluid including lymph. As another example, the pump can be actuated in response to user operation of a control external to the body of the patient. The pump can be configured to be activated periodically or continuously.

In some embodiments, the vein includes one of the patient's subclavian vein and internal jugular vein. In some embodiments, the method further includes implanting a pressure sensor in a location within the body of the patient that enables the pressure sensor to measure pressure in a desired region of the body of the patient. In some embodiments, the method further includes measuring the pressure in the desired region using the pressure sensor, and activating the pump in response to the measured pressure exceeding a predefined threshold. In some embodiments, the method further includes measuring the pressure in the desired region using the pressure sensor, and controlling a speed of operation of the pump depending on the measured pressure.

In some embodiments, the power source includes a battery. The battery can be a rechargeable battery. The method can further include activating the pump to cause the pump to continuously pump the fluid from the thoracic duct to the vein.

BRIEF DESCRIPTION OF DRAWINGS

This disclosure will be more fully understood from the following detailed description taken in conjunction with the accompanying drawings, in which:

FIG. 9A is a side view of a distal portion of the implantable system of FIG. 7;

FIG. 9B is a perspective view of the distal portion of FIG. 9A;

FIG. 13 is a cross-sectional view of a main catheter of the implantable catheter system of FIG. 7;

FIG. 16 is a side view of an impeller housing of the implantable catheter system of FIG. 7;

FIG. 25 is a partially transparent side view of a distal portion of the implantable catheter system of FIG. 24;

FIG. 26A is a cross-sectional side view of a bearing disposed in an impeller housing of the implantable catheter system of FIG. 24;

FIG. 26B is a cross-sectional view of a catheter shaft of a catheter system in accordance with the described techniques;

FIG. 26C is a perspective view of a proximal restriction member of the implantable catheter system of FIG. 24;

DETAILED DESCRIPTION

Figure 1:
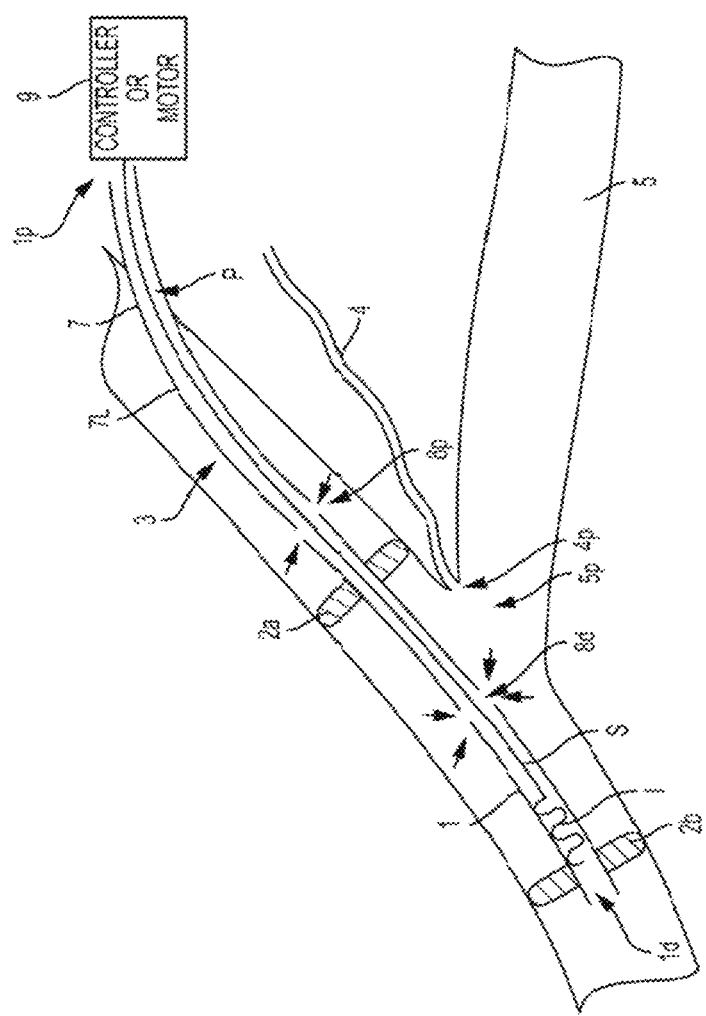
FIG. 1 is a schematic cross-sectional view of one embodiment of a catheter implanted in a vein of a patient.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Reference throughout the specification to "various embodiments," "some embodiments," "one embodiment," or "an embodiment," or the like, means that a particular feature, structure, or characteristic described in connection with the embodiment is included in at least one embodiment. Thus, appearances of the phrases "in various embodiments," "in some embodiments," "in one embodiment," or "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various systems and methods are provided for reducing pressure at an outflow of a duct such as the thoracic duct or a lymphatic duct, for example, the right lymphatic duct. In general, the systems and methods may be effective to relieve fluid overload in patients with diagnosed edema conditions and in patients at risk of developing edema, such as pulmonary edema, by lowering an outflow pressure in a region around the patient's duct outflow. As a result of lowering the outflow pressure at the thoracic and/or lymphatic ducts, higher lymphatic return will be achieved, enabling the lymphatic vessel flow to be at or near normal levels. The lymphatic drainage can be enhanced without overloading the venous system or elevating its pressure. The systems and methods may be effective to rapidly alleviate conditions of the edema and increase the patient response rate. In an exemplary embodiment, the systems and methods may be particularly useful to treat acute pulmonary edema or fluid overload as seen in most patients with acute decompensated heart failure (ADHF), however a person skilled in the art will appreciate that the systems and methods can be used in various procedures for treating a lymphatic system fluid clearance imbalance.

In one embodiment, an indwelling catheter can be configured to be at least partially implanted (e.g., partially implanted or fully implanted) within a vein of a patient in the vicinity of an outflow port of a duct of the lymphatic system, e.g., in the vicinity of an outflow port of the thoracic duct or in the vicinity of an outflow port of the lymphatic duct, for example, the right lymphatic duct. Exemplary materials from which the catheter can be made include polyurethanes or polyamides. The catheter can include first and second restrictors (also referred to herein as "restriction members") each configured to at least partially occlude the vein within which the catheter is implanted and thus to restrict fluid flow within the vein when the restrictors are activated. The restrictors can each be configured to move between an activated configuration, in which the restrictor occludes the vein, and a relaxed configuration, in which the restrictor does not occlude the vein. The restrictors can each be in the relaxed configuration during implantation of the catheter to ease introduction of the catheter into the patient's body and into the vein. Each of the restrictors can include a balloon configured to be inflated where in the relaxed configuration the balloon is not inflated and in the activated configuration in which the balloon is inflated.

The restrictors can be made from any one or more of a variety of materials configured to expand upon the delivery of a fluid thereto and to contract upon the withdrawal of the fluid. Exemplary materials from which the balloon can be made include polymeric materials such as PEBAX, silicones, polyurethanes, and nylons. The catheter can include at least one inflation lumen through which an inflation fluid (e.g., air, liquid, etc.) can be introduced to inflate/deflate the restrictors. The at least one inflation lumen can include one lumen in fluid communication with both of the restrictors such that the restrictors can be simultaneously inflated/deflated, or can include first and second lumens with the first lumen in fluid communication with the first restrictor and the second lumen in fluid communication with the second restrictor such that the restrictors can be selectively inflated simultaneously or sequentially. The catheter can include a pump, such as an axial motor pump, configured to pump fluid through the catheter. The catheter can be coupled to a motor configured to drive the pump. The motor can be included in the catheter (e.g., within a shaft of the catheter) and be configured to be implanted with the catheter, or the motor can be located outside of the catheter (e.g., outside of the catheter's shaft) and be configured to be located outside of the patient rather than be implanted therein.

In one embodiment of using the catheter, the catheter can be positioned at a desired location within the vein. The first and second restrictors can then each be activated (simultaneously or sequentially) to move from the relaxed configuration to the activated configuration. The first and the second restrictors, when activated so as to provide two occlusions within the vein, define a low pressure zone therebetween within a portion of the vein in which the catheter is positioned. Higher pressure zones or pressure zones having the same pressure as before the catheter was operated accordingly exist on either side of the restrictors. The motor can drive the pump to induce the low pressure zone by causing fluid to be pumped through the catheter. The fluid is pumped at the rate that is higher than a rate of a natural blood flow in the vein. The catheter and the restrictors can be positioned within the vein such that the low pressure zone is adjacent to an outflow port of a duct (e.g., the thoracic duct or the lymphatic duct, such as the right lymphatic duct) to allow fluid to pass from the lymph duct outflow port to the portion of the catheter housed within the vein so that fluid can flow out of the catheter.

In at least some embodiments, the restrictor(s) of a catheter can be inflated and deflated from time to time to enable free flow of blood in a patient's vein in which the restrictor(s) are positioned and thus enable the system to stop working for a period of time. This period of time can be required in such treatments to allow for the assessment of the patient's clinical condition, allow the patient to undergo other treatments or enable him to go to the bathroom and/or to wash any stagnation points that might have occurred.

The catheters described herein can be configured to be placed in a patient's body for up to about seventy-two hours, e.g., the catheter can be indwelled in the body for up to about seventy-two hours. The catheter systems described herein that include the catheters can be operated in a treatment time period in a range of about 6 to 8 hours. At the end of each treatment period, the restrictors are deflated, the catheter can be filled with a heparin catheter locking solution, and an assessment of the patient's clinical condition can be performed. The catheter system can be operated again if desired by medical personnel. Within the indwelling period of the catheter, a number of treatment periods can be in a range of 3 to 6 cycles, e.g., for a maximum of about forty hours of operation within a seventy-two hour indwelling period.

A person skilled in the art will appreciate that the systems and methods disclosed herein can be used with a variety of surgical devices, including measuring devices, sensing devices, locator devices, insertion devices, etc.

FIG. 1 illustrates one embodiment of a catheter 1 that includes at least one restrictor 2a, 2b. The at least one restrictor includes first and second restrictors 2a, 2b in this illustrated embodiment, which each include a balloon configured to be inflated (corresponding to an activated configuration) and deflated (corresponding to a relaxed configuration). The first and second restrictors 2a, 2b can be spaced a distance apart from one another along a longitudinal length of the catheter 1 such that one of the restrictors 2b is more distal than the other of the restrictors 2a. The distance between the first and second restrictors 2a, 2b can define a length of a low pressure zone that can be created when the catheter 1 is implanted within a vein. FIG. 1 shows the catheter 1 positioned within an internal jugular vein 3 of a patient with the distal restrictor 2b positioned distal to an outflow port 4p of the patient's thoracic duct 4 and the proximal restrictor 2a positioned proximal to the outflow port 4p of the patient's thoracic duct 4. The low pressure zone defined between the proximal and distal (first and second) restrictors 2a, 2b can thus be located adjacent the outflow port 4p of the thoracic duct 4. The proximal restrictor 2a being positioned proximal to (e.g., upstream) of the outflow port 4p of the thoracic duct 4 may help prevent back flow from the patient's subclavian vein 5 while providing the low pressure zone and benefit(s) thereof. The catheter 1 can be similarly positioned on a right side of the patient with the distal restrictor 2b positioned distal to an outflow port of the patient's subclavian vein 5 and an outflow port of the patient's lymphatic duct, such as, for example, the right lymphatic duct, (not shown) and the proximal restrictor 2a positioned proximal to the outflow port of the patient's subclavian vein 5 and the outflow port of the patient's lymphatic duct.

The catheter 1 can include at least one inflation lumen (omitted from FIG. 1 for clarity of illustration) configured to facilitate inflation of the first and second restrictors 2a, 2b, e.g., to facilitate movement of the restrictors 2a, 2b between the activated and relaxed configurations. The first and second restrictors 2a, 2b are shown in the activated configuration in FIG. 1 with the first and second restrictors 2a, 2b each abutting an internal surface of the jugular vein 3 so as to provide two, spaced-apart occlusions therein.

The catheter 1 can include a shaft 7 having a lumen 7L, as shown in this illustrated embodiment, configured to communicate fluid therethrough so as to accommodate the flow of fluid in a vein in which the catheter 1 is implanted. The shaft 7 can have a variety of sizes, such as having a diameter that is in the range of about 8 to 18 Fr (e.g., about 8 Fr, equal to or less than about 12 Fr, etc.) and having a length in the range of about 25 to 40 cm.

The first and second restrictors 2a, 2b can be attached to and surround the shaft 7. The first and second restrictors 2a, 2b can each be formed in the shape of a torus, as in this illustrated embodiment, to facilitate the surrounding of the shaft 1 and/or to help prevent compression of the restrictors 2a, 2b when they are moved radially outward during expansion thereof and thereby thus overcoming a possible tendency for the restrictors 2a, 2b to collapse in response to an external pressure. The first and second restrictors 2a, 2b can, however, have other shapes.

The catheter 1 can have a first or distal suction inlet 8d formed through the shaft's sidewall. The distal suction inlet can be in communication with the lumen 7L so as to allow fluid to enter the lumen 7L therethrough, as shown in FIG. 1 by four arrows at the distal suction inlet 8d pointing inward toward the lumen 7L. The distal suction inlet 8d can include any number of openings formed through the shaft's sidewall. The openings can have any of a variety of configurations, e.g., slits, circular holes, ovular holes, rectangular slots, etc. The distal suction inlet 8d can be located along the catheter's longitudinal length at a position between the first and second restrictors 2a, 2b. The distal suction inlet 8d can thus be located within the low pressure zone. In an exemplary embodiment, as shown in FIG. 1, in use, the distal suction inlet 8d can be positioned adjacent the outflow ports 4p, 5p of the thoracic duct 4 and the subclavian vein 5 so as to allow fluid exiting the outflow ports 4p, 5p to enter the catheter 1.

The catheter 1 can include a second or proximal suction inlet 8p formed through the shaft's sidewall. The proximal suction inlet 8p can be in communication with the lumen 7L so as to allow fluid to enter the catheter's lumen 7L therethrough, as shown in FIG. 1 by two arrows at the proximal suction inlet 8p pointing inward toward the lumen 7L. The proximal suction inlet 8p can include any number of openings formed through the shaft's sidewall. The openings can have any of a variety of configurations, e.g., slits, circular holes, ovular holes, rectangular slots, etc. The proximal suction inlet 8p can be located proximal to the distal suction inlet 8d and proximal to the first and second restrictors 2a, 2b. In an exemplary embodiment, as shown in FIG. 1, in use, the proximal suction inlet 8p can be positioned proximal to the outflow ports 4p, 5p of the thoracic duct 4 and the subclavian vein 5, e.g., upstream thereof. The proximal suction inlet 8p may thus allow for regular fluid flow through the jugular vein 3 even when the proximal restrictor 2a is activated and occluding the jugular vein 3.

The catheter 1 can include a distal end 1d configured to be implanted within the patient's body (e.g., within the jugular vein 3, as shown in this illustrated embodiment) and a proximal end 1p configured to not be implanted and instead be located outside the patient's body when the catheter's distal end 1d is implanted. The distal end 1d of the catheter 1 can be open so as to define a discharge opening of the catheter 1 that allows fluid in the lumen 7L to exit the catheter 1 therethrough. The distal restrictor 2b being positioned proximal to the discharge opening may help prevent back flow of fluid exiting the catheter 1 through the discharge opening. The distal restrictor 2b can thus be positioned just proximal to the discharge opening to help maximize backflow prevention. The catheter's proximal end 1p is configured to not be implanted and is shown outside of the patient's body in FIG. 1. FIG. 1 also shows a controller or motor 9 coupled to the catheter 1 and located outside of and proximal to the catheter's proximal end 1p so as to not be within the catheter's shaft 7 and to be located outside of the patient's body. Alternatively, as mentioned above, the catheter's proximal end 1p can be configured to be implanted, such as when the controller or motor 9 is included in the catheter's shaft 7.

The catheter 1 can include a pump configured to drive fluid flow through the catheter 1, e.g., through the lumen 7L thereof. The pump can have a variety of configurations. As in this illustrated embodiment, the pump can include an axial motor pump. The axial motor pump can generally be configured like an Archimedes' screw that drives fluid. The axial motor pump can include an impeller I and a drive shaft S (e.g., a cable or a rod) each located in the catheter's shaft 7, e.g., in the lumen 7L. Also as in this illustrated embodiment, the impeller I can be located fully distal to the proximal restrictor 2a and can be located at least partially proximal to the second restrictor 2b so as to be at least partially located within the low pressure zone and hence near the distal inlet opening. In this illustrated embodiment, the impeller I is fully located within the low pressure zone. The drive shaft S can extend longitudinally through the catheter 1, e.g., through the lumen 7L, to the controller or motor 9. The motor 9 can be configured to drive the drive shaft S, e.g., to rotate the drive shaft S, and hence drive the impeller I, e.g., rotate the impeller I. The drive shaft S can be a solid member, which may provide structural stability to the drive shaft S. Alternatively, the drive shaft S can be hollow, e.g., be cannulated. The drive shaft S being hollow can allow a guide wire to be advanced therethrough, which may facilitate delivery of the catheter 1 into a vein, as will be appreciated by a person skilled in the art, such as by allowing the guide wire to be introduced into a vein and the catheter 20 to then be advanced over the guide wire (and into a sheath (not shown) of the system 10 advanced over the guide wire prior to the catheter 20 being advanced over the guide wire, if the system 10 includes a sheath). For example, the guide wire can be introduced into the jugular vein 3 (e.g., a Seldinger technique via a central venous access under ultrasound guidance), and then the drive shaft S (and the catheter 1 coupled thereto) can be advanced over the guide wire into the jugular vein 3.

The pump can be configured to pump fluid at a variety of rates. In an exemplary embodiment, the pump can be configured to pump fluid at a rate in a range of about 100 to 1000 ml/min, which can provide a pressure reduction in the low pressure zone from a pressure in a range of about 10 to 20 mmHg (the pressure in the higher pressure zones) to a pressure in a range of about 0 to 6 mmHg (e.g., in a range of about 2 to 4 mmHg, which is a typical normal level, or in a range of about 2 to 5 mmHg, which is also a typical normal level). In at least some embodiments, the pump can have a static, e.g., unchangeable, flow rate. The flow rate can thus be predictable and/or chosen for a specific patient. In other embodiments, the pump can have an adjustable flow rate. The flow rate being adjustable can help the pump accommodate changes in the patient's condition over time and/or allow the pump to be driven at a selected rate for a particular patient. The flow rate can be adjustable in a variety of ways, as will be appreciated by a person skilled in the art, such as by being wirelessly adjusted using a user-operated control device located external to the patient and configured to wirelessly communicate with the pump (e.g., with the controller 9) to adjust the flow rate thereof.

In at least some embodiments, the controller 9 can be configured to be in electronic communication with at least one pressure sensor (not shown). A person skilled in the art will appreciate that a variety of suitable sensors can be used for monitoring pressure, such as central venous pressure (CVP) or other fluid pressure sensors, and blood pressure sensors. The at least one pressure sensor can be implanted in the patient as part of the pump, implanted in the patient as a separate component from the pump, or the at least one pressure sensor can be located external to the patient, such as by being on a skin surface thereof. If not already a part of the pump so as to be in electronic communication therewith, the at least one pressure sensor can be configured to be in electronic communication with the pump over a communication line such as a wired line or a wireless line. In an exemplary embodiment, two pressure sensors can be implanted in the patient. One of the pressure sensors can be implanted between the first and second restrictors 2a, 2b so as to be in the low pressure zone, and the other one of the pressure sensors can be implanted in the vein either proximal to the proximal restrictor 2a (e.g., proximal to the proximal inlet) or distal to the distal restrictor 2b (e.g., distal to the discharge opening) so as to be in one of the higher pressure zones. The two sensors can thus allow a pressure differential to be determined between the low pressure zone and the higher pressure zone. In other embodiments, another number of pressure sensors can be implanted in the patient (e.g., one, three, four etc.) and/or the pressure sensor(s) can be implanted at other locations.

The catheter 1 can include at least one lumen (not shown) configured to facilitate use of the pressure sensor(s), for example to facilitate placement of the pressure sensor(s) and/or to be filled with a fluid such as saline to allow for external pressure measurement.

In addition to or instead of the one or more pressure sensors, the controller 9 can be configured to be in electronic communication with at least one other type of sensor (not shown) configured to sense a parameter other than pressure. Examples of sensors that can be used to measure a parameter other than pressure include radio frequency transmitters and receivers, fluid sensors, bioimpedance sensors, heart rate sensors, breathing sensors, activity sensors, and optical sensors. Examples of the measured parameter include fluid amount (e.g., as measured by a fluid sensor, such as a fluid sensor placed in a lung to sense fluid amount in the lung), bioimpedance (e.g., as measured by a bioimpedance sensor), heart rate (e.g., as measured by a heart rate sensor), breathing rate (e.g., as measured by a breathing sensor), patient activity level (e.g., as measured by an activity sensor), and organ dimension (e.g., as measured by an optical sensor). The sensor can be implanted in the patient as part of the pump, implanted in the patient as a separate component from the pump (e.g., implanted in an interstitial space around a lung, implanted at a junction of a right subclavian vein of a patient and an internal jugular vein of the patient, implanted at a junction of a left subclavian vein of a patient and an internal jugular vein of the patient, etc.), or the sensor can be located external to the patient, such as by being on a skin surface thereof. If not already a part of the pump so as to be in electronic communication therewith, the non-pressure sensor(s) can be configured to be in electronic communication with the pump over a communication line such as a wired line or a wireless line. The non-pressure sensor(s) can include one or more sensors. In embodiments including a plurality of sensors, each of the sensors can be configured to measure the same parameter as or a different parameter than any one or more of the other sensors.

The motor 9 can be included as part of the pump and can be configured to be implanted in the patient with the pump, or, as in this illustrated embodiment, the 9 can be configured to be non-implantable. The motor 9 being non-implantable can help the pump have a smaller size and/or can allow the pump to be driven by a more powerful motor since the motor 9 can be larger than an implantable motor.

The controller 9 can be included as part of the pump and can be configured to be implanted in the patient with the pump, or, as in this illustrated embodiment, the controller 9 can be configured to be non-implantable. The controller 9 being part of the pump can help allow the pump to be a self-contained system, although in such a controller requires space in the pump, which can increase a size of the pump. The controller 9 being non-implantable can help the pump have a smaller size and/or can allow the pump to be controlled by a more powerful processor since the processor can be more easily upgraded than if implanted with the pump and/or since the processor's size can be less important when outside the pump as opposed to inside the pump.

The controller 9 can include any type of microprocessor or central processing unit (CPU), including programmable general-purpose or special-purpose microprocessors and/or any one of a variety of proprietary or commercially available single or multi-processor systems. The controller 9 can be a component of a control system that includes any number of additional components, such as a memory configured to can provide temporary storage and/or non-volatile storage; a bus system; a network interface configured to enable the control system to communicate with other devices, e.g., other control systems, over a network; and an input/output (I/O) interface configured to connect the control system with other electronic equipment such as I/O devices (e.g., a keyboard, a mouse, a touchscreen, a monitor, etc.) configured to receive an input from a user.

The controller 9 can be configured to receive user input thereto to control any of a variety of aspects related to the catheter 1, such as speed of the motor 9 and ideal range of pressure for the low pressure zone.

In at least some embodiments, the pump can be configured to change its pumping rate (e.g., from zero to a non-zero value, from a non-zero value to zero, or from one non-zero value to another non-zero value) based on pressure measured by the at least one pressure sensor. The controller 9 can be configured to effect such change in response to the sensed pressure. If the measured pressure exceeds a predetermined threshold maximum pressure value, the pump can be configured to increase its pump rate (e.g., increase from zero or increase from some non-zero value) in an effort to decrease the pressure. For example, if the measured pressure within the low pressure zone is too high (e.g., is above a predetermined threshold), the pump can increase its pump rate to decrease the pressure within the low pressure zone. For another example, if the measured pressure within the low pressure zone is below a predetermined threshold, the pump can decrease its pump rate to maintain or increase the pressure within the low pressure zone. For yet another example, if a measured pressure differential between the low pressure zone and the higher pressure zone is not sufficiently great (e.g., is below a predetermined threshold), the pump can increase its pump rate to increase the pressure differential.

In at least some embodiments, the catheter 1 can include only one restrictor, the proximal restrictor 2a. A higher pressure zone can thus be proximal to the proximal restrictor, and a low pressure zone can be distal to the proximal restrictor. The proximal restrictor 2a positioned proximal to (e.g., upstream) of the outflow port 4p of the thoracic duct 4 being the only restrictor of the catheter 1, instead of the distal restrictor 2b positioned distal to (e.g., downstream) of the outflow port 4p of the thoracic duct 4, may help prevent back flow from the subclavian vein 5 while providing the low pressure zone and benefit(s) thereof.

In at least some embodiments, the catheter 1 can have a soft atraumatic tip at its distal end 1d that is tapered in a distal direction and that is flexible. The soft atraumatic tip may facilitate smooth, safe introduction of the catheter 1 into the vein 3. Exemplary materials from which the atraumatic tip can be made include polyurethanes. The catheter may additionally include a flexible extension similar to a guide wire tip and/or have a hydrophilic coating, each of which may further facilitate smooth, safe introduction of the catheter 1 into the vein 3.

In at least some embodiments, the proximal restrictor 2a can be configured to only partially occlude the vein 3 in which the catheter 1 is positioned when the proximal restrictor 2a in its activated configuration. This partial occlusion may facilitate normal fluid flow through the vein 3 even when the proximal restrictor 2a is in the activated configuration. In embodiments in which the proximal restrictor 2a is configured to only partially occlude the vein 3 when in its activated configuration, the catheter 1 can, but need not, include the proximal inlet 8p to facilitate fluid flow through the vein 3. The partial occlusion can be achieved in a variety of ways. For example, the proximal restrictor 2a can have at least one lumen or hole formed therethrough configured to allow fluid flow therethrough when the proximal restrictor 2a is in the activated configuration. For another example, a maximum diameter of the proximal restrictor 2a in the activated configuration can be less than a maximum internal diameter of the vein 3 in which the catheter 1 is positioned to allow fluid flow around an exterior of the proximal restrictor 2a.

In at least some embodiments, the catheter 1 can include at least one lumen or tube (not shown) configured to pass blood therethrough outside the patient's body and back into the patient. Such functionality may allow for the monitoring of blood volume and performing hemofiltration.

In at least some embodiments, the catheter 1 can include one or more radiopaque markers (not shown) configured to be visible using an imaging technique such as fluoroscopy. The one or more radiopaque markers can be on the catheter's shaft 7 at or near one or more features along the shaft 7, such as any or all of the inlet openings or any or all of the restrictors 2a, 2b. The one or more radiopaque markers may thus facilitate proper positioning of the shaft 7 and/or features thereon within a vein. For example, prior to activation of the catheter's restrictor(s) 2a, 2b, the position of the restrictor(s) 2a, 2b within the vein 3 can be verified by visualizing the one or more radiopaque markers using an imaging system.

The first and second restrictors 2a, 2b are discussed with respect to FIG. 1 above as being balloons configured to inflate and deflate, but the first and second restrictors 2a, 2b can have other configurations. For example, the first and second restrictors 2a, 2b can each include a stent configured to expand (corresponding to an activated configuration) and constrict (corresponding to a relaxed configuration). The expandable/constrictable stents can have a variety of configurations, as will be appreciated by a person skilled in the art. Further details related to an indwelling catheter are described in U.S. application Ser. No. 15/150,637 entitled "Systems and Methods for Reducing Pressure at an Outflow of a Duct," filed May 10, 2016.

In some embodiments, a catheter can include an integral pump that can pump blood from the external volume between restrictions of the catheter into catheter's conduit. The pump can be associated with a motor (which can be similar to the motor 9 in FIG. 1) that can be configured to be non-implantable such that it is disposed outside of the patient. The pump motor can be coupled to an impeller (which can also be referred to as pump rotor) via a drive shaft, as discussed above. The motor being non-implantable can help the pump have a smaller size and/or can allow the pump to be driven by a more powerful motor since the motor can be larger than an implantable motor. Furthermore, in some embodiments, the motor can be included as part of the pump and can be configured to be implanted in the patient with the pump.

The catheter also includes first and second restrictors each configured to at least partially occlude the vein within which the catheter is implanted and thus to restrict fluid flow within the vein when the restrictors are activated. The restrictors can each be configured to move between an activated configuration in which the restrictor occludes the vein, and a relaxed configuration in which the restrictor does not occlude the vein. The restrictors can each be in the relaxed configuration during implantation of the catheter to ease introduction of the catheter into the patient's body and into the vein. Each of the restrictors can include a balloon configured to be inflated, where in the relaxed configuration the balloon is not inflated and in the activated configuration the balloon is inflated.

Figure 2:
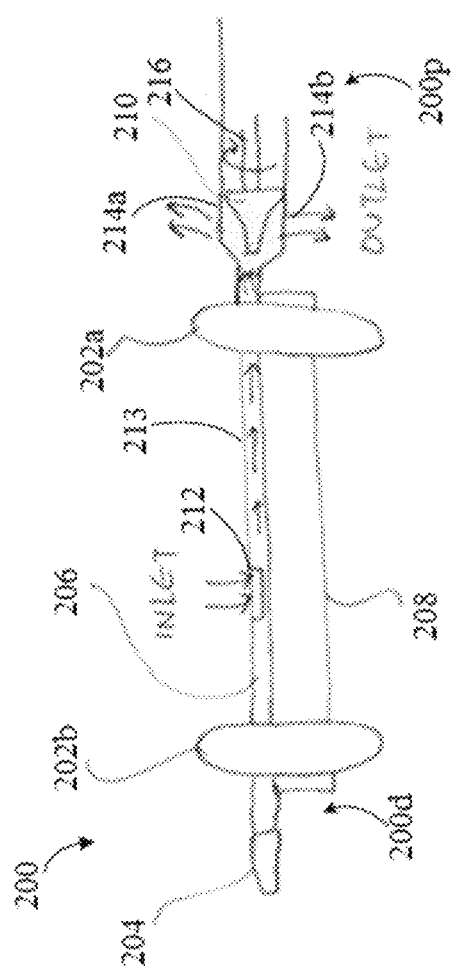
FIG. 2 is a schematic cross-sectional view of an embodiment of a catheter in accordance with the described techniques.

The impeller can be disposed at various locations within the catheter. For example, FIG. 2 illustrates schematically an example of a catheter 200, having proximal and distal ends 200p, 200d, that has first and second restrictors 202a, 202b and an impeller 210 positioned proximally of the first restrictor 202a. In this example, the first restrictor 202a is a proximal restrictor and the second restrictor 202b is a distal restrictor. The first and second restrictors 202a, 202b can be in the form of expandable elements such as balloons and are shown in FIG. 2 in an activated, inflated configuration in which they occlude the vein. The catheter 200 also has an atraumatic tip 204 that facilitates placement of the catheter into the vein of the patient, a catheter shaft 206 having an inlet tube 213 extending therethrough, a conduit 208, inlet opening 212 and two opposed outlet openings 214*a*, 214*b* formed in the wall of the catheter 200. The impeller 210 can be coupled to a motor (not shown) via a drive shaft 216. The components of the catheter 200 can be similar to the components of the catheter 1 (FIG. 1) and are therefore not described in detail.

Figure 3:
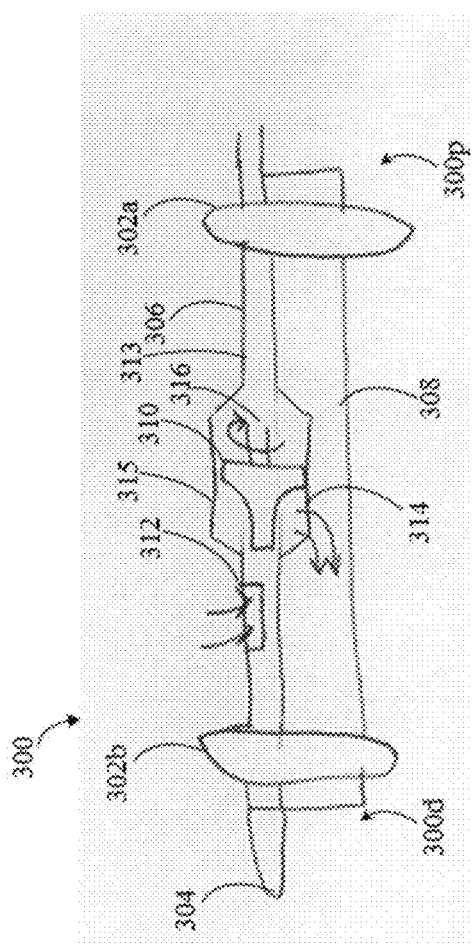
FIG. 3 is a schematic cross-sectional view of another embodiment of a catheter in accordance with the described techniques.

FIG. 3 illustrates schematically another embodiment of a catheter 300 in accordance with the described techniques having an impeller positioned between first and second restrictors. As shown in FIG. 3, a catheter 300, having proximal and distal ends 300*p*, 300*d*, has first and second restrictors 302*a*, 302*b* and an impeller 310 positioned between the first and second restrictors 302*a*, 302*b*. In this example, the first restrictor 302*a* is a proximal restrictor and the second restrictor 302*b* is a distal restrictor. The first and second restrictors 302*a*, 302*b* can be in the form of expandable elements such as balloons and are shown in FIG. 3 in an activated, inflated configuration in which they occlude the vein. Similar to the catheter 200 in FIG. 2, the catheter 300 has an atraumatic tip 304, a catheter shaft 306 having an inlet tube 313 extending therethrough, a conduit 308, and inlet and outlet openings 312, 314. In some embodiments, the outlet opening 314 can be in the form of two opposed openings formed in the wall of the inlet tube 313.

The impeller 310 can be coupled to a motor (not shown) via a drive shaft 316. As shown in FIG. 3, the impeller 310 and at least a portion of the drive shaft 316 (which is shown partially) are disposed in an enlarged portion 315 of the inlet tube 313. The components of the catheter 300 can be similar to the components of the catheter 1 (FIG. 1) and are therefore not described in detail.

Figure 4:
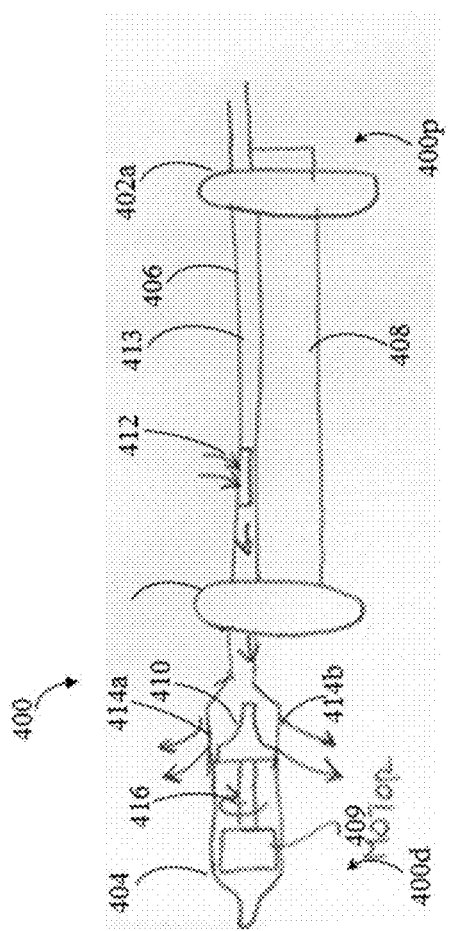
FIG. 4 is a schematic cross-sectional view of yet another embodiment of a catheter in accordance with the described techniques.

FIG. 4 illustrates schematically another embodiment of a catheter in accordance with the described techniques having an impeller positioned distally of a distal (or "second") restrictor. Thus, as shown in FIG. 4, a catheter 400, having proximal and distal ends 400*p*, 400*d*, has first (proximal) and second (distal) restrictors 402*a*, 402*b*. The first and second restrictors 402*a*, 402*b* can be in the form of expandable elements such as balloons and are shown in FIG. 4 in an activated, inflated configuration in which they occlude the vein. The catheter 400 has an impeller 410 positioned distally of the distal restrictor 402*b*. Similar to the catheter 200 in FIG. 2, the catheter 400 has an atraumatic tip 404, a catheter shaft 406 having an inlet tube 413 extending therethrough, a conduit 408, an inlet opening 412 and two opposed outlet openings 414*a*, 414*b*. As shown in FIG. 4, the impeller 410 is coupled to a motor 409 via a drive shaft 416. In this implementation, the motor 409 is disposed within an enlarged portion of the catheter's tip 404, as shown in FIG. 4.

In the examples shown in FIGS. 2, 3 and 4, an inlet opening of the pump can be within a tube or it can be formed to extent inwards from radial openings. The outlet opening of the pump can be formed into a tube or it can be formed to extend outward via radial openings. Any of the catheters 200, 300, and 400 can include one or more sensors positioned at desired locations. For example, at least one pressure sensor can be disposed between the restrictors and can monitor the lymphatic outlet pressure. The pump can be an implantable pump. The motor configured to operate the impeller can include or can be associated with a controller. The controller can control various operating parameters of the impeller, such as its speed. The lymphatic outlet pressure as well as the motor current and voltage consumption can be used as inputs to the motor controller.

Figure 5:
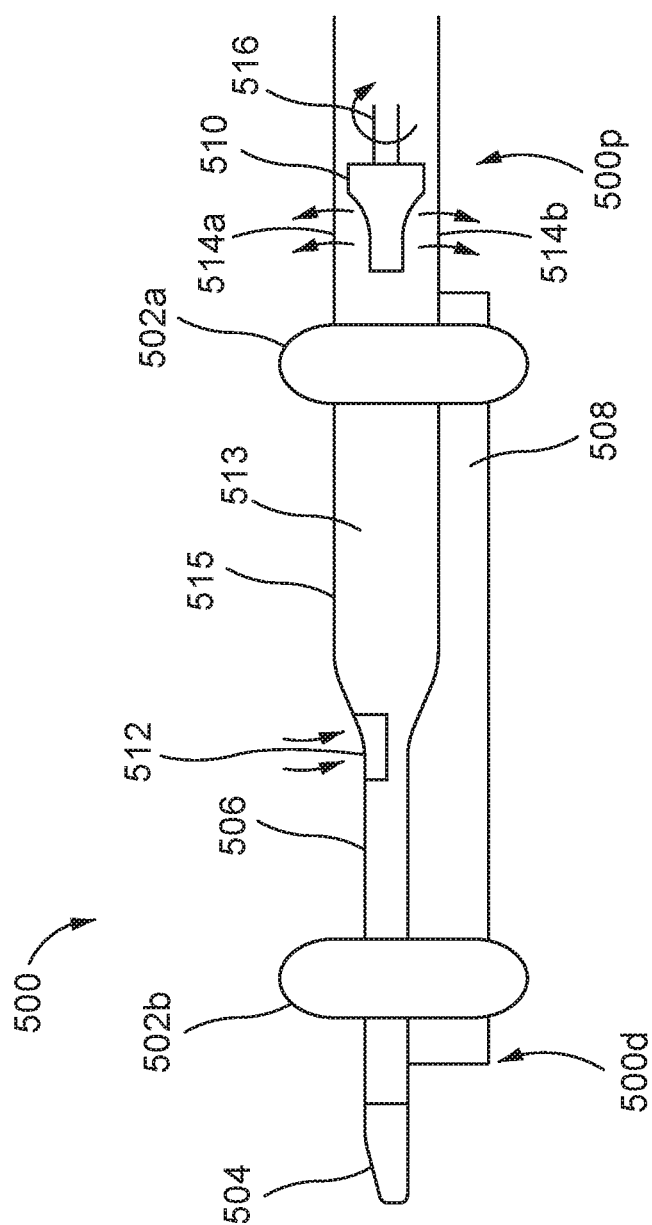
FIG. 5 is a schematic cross-sectional view of yet another embodiment of a catheter in accordance with the described techniques.

In some embodiments, the pump inlet tube can be expandable to handle more fluid (e.g., from the thoracic duct) and to reduce flow resistance. The expandable segment can extend between the inlet tube opening and the impeller. FIG. 5 illustrates schematically another embodiment of a catheter 500 in accordance with the described techniques having an impeller positioned proximally of a proximal restrictor and having an expandable inlet tube segment extending between the inlet tube opening and the impeller.

As shown in FIG. 5, the catheter 500, having proximal and distal ends 500*p*, 500*d*, has first (proximal) and second (distal) restrictors 502*a*, 502*b* and an impeller 510 positioned proximally of the proximal restrictor 502*a*. The first and second restrictors 502*a*, 502*b* can be in the form of expandable elements, such as, e.g., balloons, that are shown in FIG. 5 in an activated, inflated configuration in which they occlude the vein. The catheter 500 has an atraumatic tip 504, a catheter shaft 506 having an inlet tube 513 extending therethrough, a conduit 508, an inlet opening 512 and two opposed outlet openings 514*a*, 514*b*. As shown, the inlet tube 513 has an expanded portion 515 extending between the inlet tube opening 512 and the impeller 510.

The impeller 510 can be coupled to a motor (not shown) via a drive shaft 516. The components of the catheter 500 can be similar to the components of the catheter 1 (FIG. 1) and are therefore not described in detail.

The catheters 200, 300, 400, and 500 can be disposed within the patient's body to alleviate fluid overload similar to the manner in which catheter 1 (FIG. 1) is shown to be disposed within the patient's body. However, it should be appreciated that the catheters 200, 300, 400, and 500 can be disposed in the patient's body in other ways.

Figure 6:
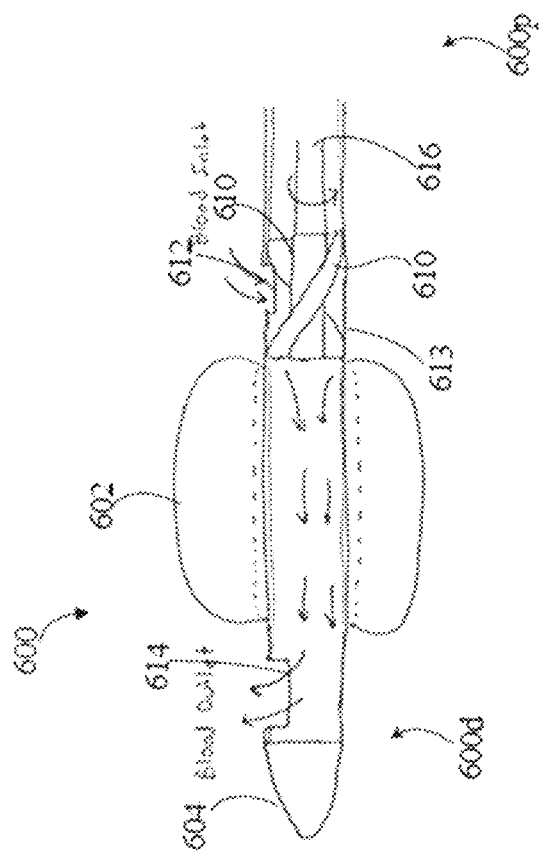
FIG. 6 is a schematic cross-sectional view of yet another embodiment of a catheter in accordance with the described techniques.

In some embodiments, a single restrictor can be used. The restrictor can be positioned, for example, in the left innominate vein so the blood pressure above the restrictor is reduced by pumping the blood downstream into the innominate vein. FIG. 6 illustrates schematically another embodiment of a catheter 600 in accordance with the described techniques having one restrictor 602 and an impeller 610 positioned proximally of the restrictor 602. The restrictor 602 can be in the form of an expandable element, such as, e.g., balloon that is shown in FIG. 6 in an activated, inflated configuration in which it occludes the vein.

As shown in FIG. 6, the catheter 600, having proximal and distal ends 600*p*, 600*d*, has an atraumatic tip 604, a catheter shaft such as an inlet tube 613, an inlet opening 612 and an outlet opening 614. The impeller 610 can be coupled to a motor (not shown) via a drive shaft 616. As shown, the impeller 610 is disposed in proximity to the inlet opening 612, to cause the blood to enter the catheter shaft. As also shown in FIG. 6, the restrictor 602 is a compliant restrictor that is disposed around the catheter shaft in a manner that allows the blood to flow therethrough. The impeller 610 is configured to pump fluid through the catheter shaft regardless of whether the restrictor 602 is in the activated configuration or the relaxed configuration. However, the catheter 600 is configured to lower the pressure at the thoracic duct outlet only when the restrictor 602 is in the activated configuration (e.g., inflated) and when the impeller 610 is operating.

It should be appreciated that the indwelling catheters 200, 300, 400, 500, and 600 are shown by way of example only. It should also be appreciated that these catheters can have other components not shown herein. For example, as mentioned above, any of the catheters can have one or more sensors of various types. Any of the catheters 200, 300, 400, 500, and 600 can include at least one inflation lumen through which an inflation fluid (e.g., air, liquid, etc.) can be introduced to inflate/deflate the restrictors. The catheters can be delivered to a treatment site using a sheath configured to be at least partially implantable within a patient's vein, the sheath having a lumen extending therethrough. The catheter shaft can be movably positioned within and extending through the lumen of the sheath, and the catheter shaft can be configured to be at least partially implantable within a patient's vein. Thus, the catheters described herein can be part of an indwelling catheter system configured for at least partial placement within a vein of a patient.

In some embodiments, various systems and methods are provided for reducing pressure at an outflow of a duct such as the thoracic duct or the lymphatic duct, for example, the right lymphatic duct. An indwelling catheter can be configured to be at least partially implanted within a vein of a patient in the vicinity of an outflow port of a duct of the lymphatic system. The catheter can include a drive shaft operatively coupled to an impeller, a first selectively deployable restriction member adjacent and proximal to the impeller and having a membrane, and a second selectively deployable restriction member proximal to the first restriction member. The second restriction member is operatively coupled to a flow regulation component configured to direct a controlled volume of fluid from an upstream side of the second restriction member to a downstream side of the second restriction member. A motor can be configured to rotate the drive shaft and the impeller.

In some embodiments, various systems and methods are provided for reducing pressure at an outflow of a duct such as the thoracic duct or the lymphatic duct, for example, the right lymphatic duct. In general, the systems and methods may be effective to reduce edema conditions, such as fluid overload, in a patient by lowering an outflow pressure in a region around the patient's thoracic/lymphatic duct outflow. As a result of lowering the outflow pressure at the thoracic and/or lymphatic ducts, higher lymphatic return will be achieved, enabling the lymphatic vessel flow to be at or near normal levels. The systems and methods may be effective to rapidly alleviate conditions of the edema and increase the patient response rate. In an exemplary embodiment, the systems and methods may be particularly useful to treat acute fluid overload, however a person skilled in the art will appreciate that the systems and methods can be used in various procedures for treating a lymphatic system fluid clearance imbalance.

In one embodiment, an indwelling catheter can be configured to be at least partially implanted (e.g., partially implanted or fully implanted) within a vein of a patient in the vicinity of an outflow port of a duct of the lymphatic system, e.g., in the vicinity of an outflow port of the thoracic duct or in the vicinity of an outflow port of the lymphatic duct, for example, the right lymphatic duct. Exemplary materials from which the catheter can be made include polyurethanes. The catheter can include first and second restrictors (also referred to herein as "restriction members"), at least one of which is configured to at least partially occlude the vein within which the catheter is implanted and thus to restrict fluid flow within the vein when the restrictors are activated. The restrictors can each be configured to move between an activated configuration, in which the restrictor occludes the vein, and a relaxed configuration, in which the restrictor does not occlude the vein. The restrictors can each be in the relaxed configuration during implantation of the catheter to ease introduction of the catheter into the patient's body and into the vein. Each of the restrictors can include a balloon configured to be inflated (such that the balloon expands radially) where in the relaxed configuration the balloon is not inflated and in the activated configuration in which the balloon is inflated. The balloon can be, for example, a doughnut-shaped. The restrictors can be configured to be inflated to expand to the same or different diameters. Also, in some embodiments, the restrictors can have inner lumens of different diameters.

The restrictors can be made from any one or more of a variety of materials configured to expand upon the delivery of a fluid thereto and to contract upon the withdrawal of the fluid. Exemplary materials from which the balloon can be made include polymeric materials such as PEBAX, silicones, polyurethanes, and nylons. The catheter can include at least one inflation lumen through which an inflation fluid (e.g., air, liquid, etc.) can be introduced to inflate/deflate the restrictors. The at least one inflation lumen can include one lumen in fluid communication with both of the restrictors such that the restrictors can be simultaneously inflated/deflated, or can include first and second lumens with the first lumen in fluid communication with the first restrictor and the second lumen in fluid communication with the second restrictor such that the restrictors can be selectively inflated simultaneously or sequentially. The catheter can include a pump, such as an axial motor pump, configured to pump fluid through the catheter. The catheter can be coupled to a motor configured to drive the pump. The motor can be included in the catheter (e.g., within a shaft of the catheter) and be configured to be implanted with the catheter, or the motor can be located outside of the catheter (e.g., outside of the catheter's shaft) and be configured to be located outside of the patient rather than be implanted therein.

In one embodiment of using the catheter, the catheter can be positioned at a desired location within the vein. The first and second restrictors can then each be activated (simultaneously or sequentially) to move from the relaxed configuration to the activated configuration. The first and the second restrictors, when activated so as to provide, in combination with other components, occlusion within the vein, define a low pressure zone therebetween within a portion of the vein in which the catheter is positioned. Higher pressure zones accordingly exist on either side of the restrictors. The motor can drive an impeller to induce the low pressure zone by causing fluid to be pumped through the catheter. The catheter and the restrictors can be positioned within the vein such that the low pressure zone is adjacent to an outflow port of a duct (e.g., the thoracic duct or the lymphatic duct, such as, for example, the right lymphatic duct) to allow fluid to pass from the lymph duct outflow port to the portion of the catheter housed within the vein so that fluid can flow out of the catheter.

In at least some embodiments, at least one of the restrictors of a catheter can be inflated and deflated from time to time to enable free flow of blood in a patient's vein in which the restrictor(s) are positioned and thus enable the system to stop working for a period of time. This period of time can be required in such treatments to allow for the assessment of the patient's clinical condition, allow the patient to undergo other treatments or enable him to go to the bathroom and/or to wash any stagnation points that might have occurred. The restrictors can be configured and operated as described, for example, in U.S. application Ser. No. 14/625,930 entitled "System And Method For Treating Pulmonary Edema," filed Feb. 19, 2015, and in U.S. application Ser. No. 14/726,715 entitled "Systems and Methods for Treating Pulmonary Edema," filed Jun. 1, 2015, the content of each of which is incorporated by reference herein in its entirety. In addition, some features of the catheter system described herein can be implemented as described in U.S. App. Publ. No. 2016/0331378 entitled "Systems and Methods for Reducing Pressure at an Outflow of a Duct," filed May 10, 2016, the content of which is incorporated by reference herein in its entirety In some embodiments, the catheters described herein can be configured to be placed in a patient's body for up to about seventy-two hours, e.g., the catheter can be indwelled in the body for up to about seventy-two hours. The catheter systems are configured to be able to be accurately fixated and deployed in a patient's body. The systems can be configured to be conveniently placed to a desired location in a patient (torque can be applied), and they possess compatibility with a guide wire and sheath, ability to overcome leads and leads effects, ability to automatically maintain a working point for 72 hours (<5 mmHg at the isolated zone), and ability to measure pressure at the pressure reduction zone. It should be appreciated, however, that in other instances a catheter system in accordance with the described techniques can be indwelled in the body for a duration of time greater than seventy-two hours. The system can be configured to maintain hemostasis.

A person skilled in the art will appreciate that the systems and methods disclosed herein can be used with a variety of surgical devices, including measuring devices, sensing devices, locator devices, insertion devices, etc.

In some embodiments, a catheter system is provided that can locally reduce pressure at an outflow of a lymphatic duct and to thus enhance lymphatic drainage, without affecting the intravascular systemic blood pressure.

Figure 7:
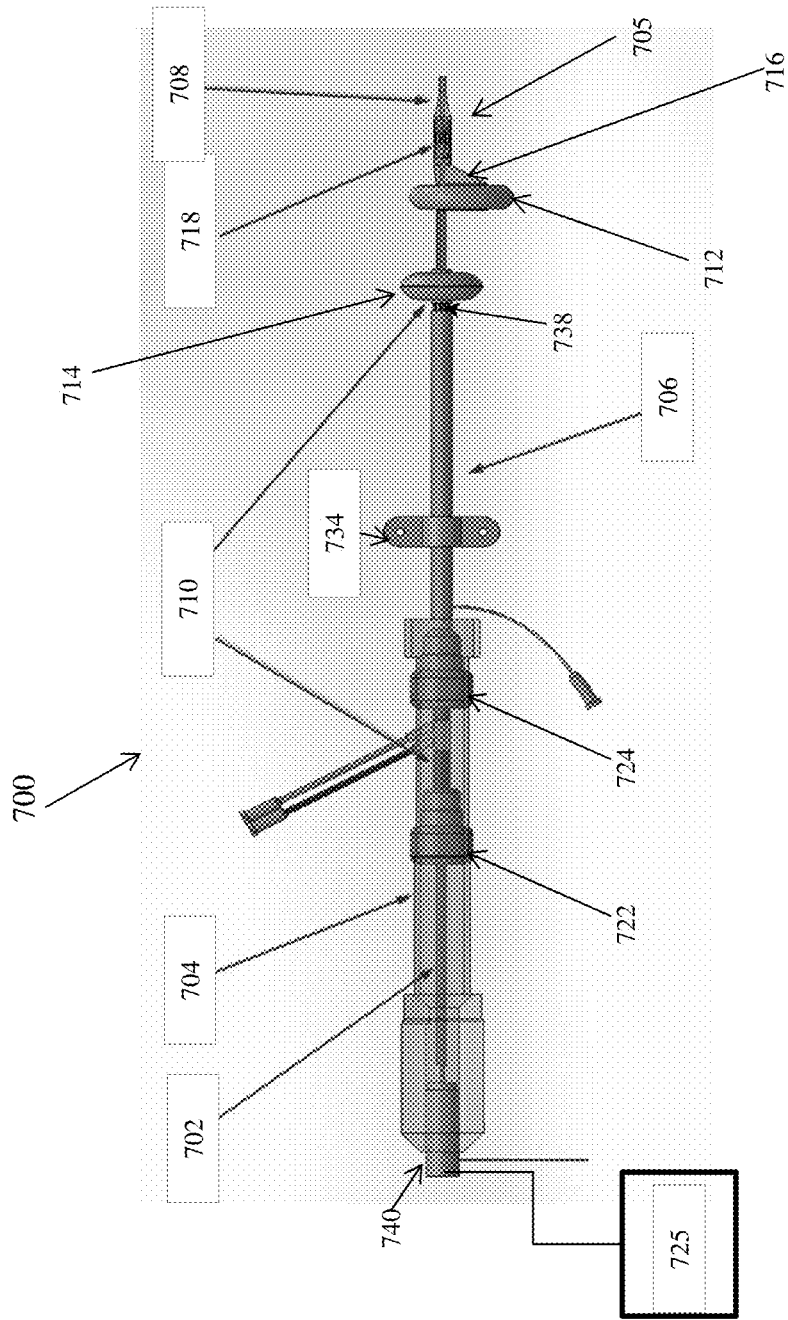
FIG. 7 is a perspective view of an embodiment of an implantable catheter system.

FIG. 7 illustrates one example of a catheter system in accordance with the described techniques. The catheter system includes an indwelling catheter, which can be in the form of a disposable catheter unit, and a mechanical fixator part which can be enclosed in a sterile package prior to use. Some components of the system, such as a console having a controller, a display configured to display information and receive user input, cables, etc., can be reusable components. As shown in FIG. 7, the system includes a main catheter tube or shaft, a distal assembly, a centralizer member, and a proximal assembly. The main catheter shaft is coupled to a propulsion system including at least an impeller and a motor (which can be disposed at least in part outside of the patient's body), a distal restriction member in the form of a distal balloon, and a distal atraumatic tip.

The centralizer member can be in the form of a housing encompassing a sealing component and at least a part of a motor. The housing is configured to keep the assemblies of the system aligned, while allowing an axial movement of the assemblies. The system includes a motor configured to move a drive shaft (e.g., a torque coiled drive shaft or a shaft having another configuration) inside a multi-lumen sleeve. In addition, the motor is configured to cause the distal balloon to inflate. One or more components of the motor can be disposed within the centralizer member. The motor can be, for example, an extracorporeal motor configured to deliver the driving force to the impeller through the drive shaft. The motor can have a shaft with a channel extending therethrough to allow a guide wire to be inserted through the shaft. Additionally or alternatively, a mechanism configured to facilitate insertion and removal of the guide wire can be utilized. The catheter can include at least one inflation lumen through which an inflation fluid (e.g., air, liquid, etc.) can be introduced to inflate/deflate the restrictors. The restrictors can be inflate/deflate using separate components. The catheter can also include a suction lumen, and any other lumens.

The proximal assembly includes a proximal assembly tube having a proximal restriction member in the form of a proximal balloon at a distal end thereof. The proximal assembly is configured to regulate blood flow in the jugular vein. The proximal assembly can include a regulation mechanism configured to adjust the central venous pressure (CVP).

FIGS. 7, 8, 9A, and 9B show one embodiment of an implantable catheter system 700 including a catheter shaft or tube 702 (which can also be referred to as a "main catheter") having a drive shaft 703 extending therethrough, a centralizer 704, a sheath 706 disposed proximally to the centralizer 704 and having the catheter tube 702 extending therethrough in a lumen thereof, and a distal tip 708. As also shown, the catheter system 700 includes distal and proximal restrictors 712, 714 disposed over the catheter tube 702. In the illustrated embodiment, the distal and proximal restrictors 712, 714 include radially expandable balloons, such as, for example, doughnut-shaped balloons. The distal tip 708 can be a distally tapered atraumatic element that facilitates insertion of the catheter system 700 into an implantation site (e.g., a vein). In some embodiments, the catheter system 700 can be fully cannulated such that a guide wire can be inserted through the entire system, including the distal tip 708.

Each of the distal and proximal restrictors 712, 714 has a lumen extending therethrough that receives the catheter tube 702 and allows the blood to pass through the lumen. In some embodiments, a diameter of the distal restrictor 712 can be greater than a diameter of the proximal restrictor 714, and a diameter of the inner lumen of the distal restrictor 712 is greater than a diameter of the inner lumen of proximal restrictor 714. In this way, whereas the proximal restrictor 714 reduces a blood flow that passes therethrough, the distal restrictor 712 allows a larger volume of the blood to flow therethrough. In other embodiments, the restrictors 712, 714 can be configured to be inflated to the same or similar diameter, whereas the distal restrictor 712 can be inflated as to become of a larger diameter than the inflated proximal restrictor 714. Also, in some implementations, the distal and proximal restrictors can have approximately the same diameter in the activated (e.g., inflated) configuration.

In some embodiments, when at least a portion of the system 700 is implanted in the patient's body and the restrictors 712, 714 are activated (or deployed), the blood passes from a proximal side of the proximal restrictor, into a zone between the restrictors, and into and through the distal restrictor, as discussed in more detail below. In this way, a low pressure zone is created between the distal and proximal restrictors 712, 714.

Figure 8:
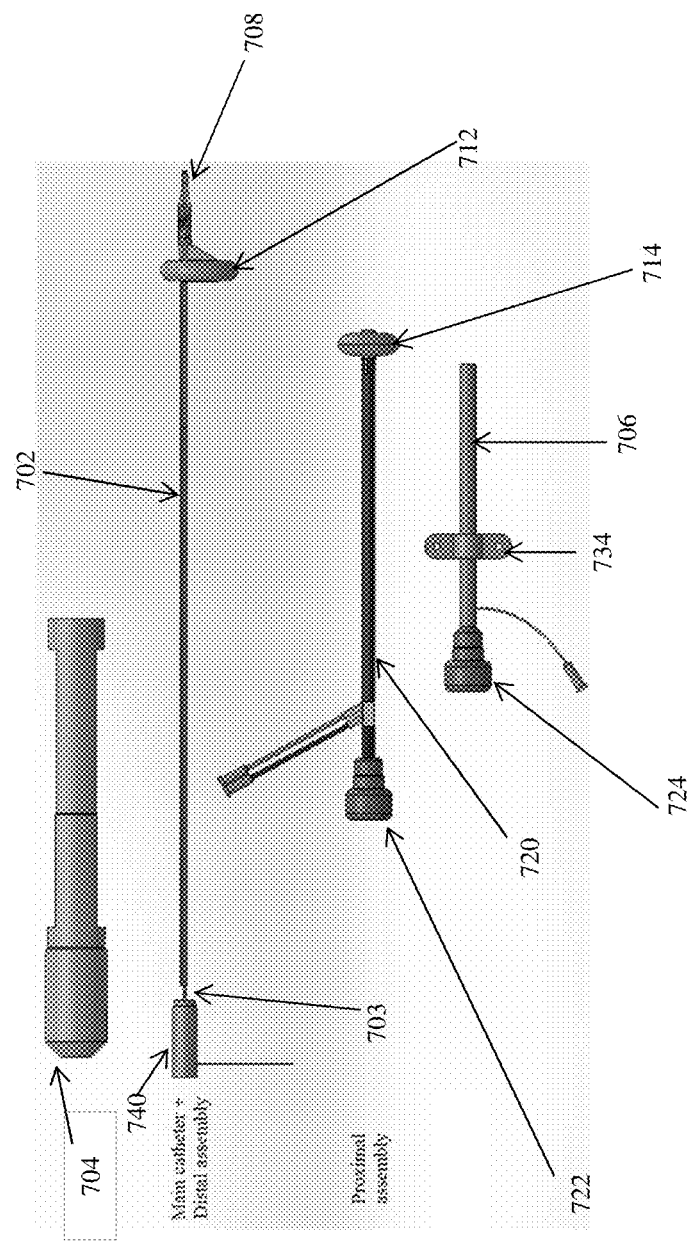
FIG. 8 is an exploded view of the implantable system of FIG. 7.

As shown in FIG. 8, a proximal assembly 710 encompasses a sleeve or proximal assembly tube 720 having a first sealing component 722 at a proximal end thereof and the proximal restrictor 714 at a distal end thereof. The catheter system 700 also includes the sheath 706 that has a portion of the proximal assembly tube 720 extending therethrough, and a second sealing component 724. In the assembled configuration, as shown in FIG. 7, the sheath 706 is disposed over the proximal assembly tube 720 such that a distal end 706d of the sheath 706 is proximal to the proximal restrictor 714. In this embodiment, an impeller assembly 705 is disposed distal to the distal restrictor 712.

As shown in FIGS. 7, 8, 9A, and 9B, a distal end of the drive shaft 703 is attached to the impeller assembly 705 that includes an impeller 715 (also shown in FIG. 15) and an impeller cage or housing 730 (also shown in FIG. 16) disposed around the impeller 715 and having openings 732

(e.g., radial openings) that allow blood to flow therefrom. The membrane 716 is, in this embodiment, a conical, distally tapered element coupled to the distal restrictor 712. The membrane 716 can define an enclosed tunnel or lumen in fluid communication with an inner lumen of the impeller housing 730 seating the impeller 715. In this way, the membrane 716 directs the fluid from the distal restrictor 712 towards the impeller 715. The distally-tapered configuration of the membrane 716 provides reduced resistance to a blood flow, thus enabling the impeller 715 to rotate as a lower speed that would otherwise be required to pump the blood at the same rate.

For example, the membrane 716 can at least partially wrap around the distal restrictor 712 or be otherwise coupled to the distal restrictor 712 to as to direct distally the blood flow that passes from a proximal to distal side of the distal restrictor 712. As shown in FIG. 9A, a distal portion 716d of the membrane 716 is attached to the impeller housing 730. For example, the distal portion 716d of the membrane 716 can at least partially wrap around a proximal end of the impeller housing 730. In this way, the blood flowing from a proximal side of the distal restrictor 712 passes through an inner lumen of the distal restrictor 712 and is directed by the membrane 716 into a tunnel or lumen of the impeller housing 730 with the impeller 715 therein. As the impeller 715 rotates, the blood (which can include other fluids) is directed from the lumen of the impeller housing 730 to the outside of the housing 730 into the vein, through openings formed in the wall of the housing 730.

In this example, as shown in FIGS. 7 and 8, the sheath 706 includes at least one fixture 734 configured to removably couple the catheter system 700 to a patient (e.g., to the patient's skin). The fixture 734 can have any suitable configuration. The sheath 706 can also have components that cover and protect the sheath 706 during deployment of the catheter system 700. In the illustrated embodiment, the sheath 706 is disposed so as to encompass at least a portion of the proximal assembly 710 such that the proximal restrictor 714 is disposed distally to the distal end 706d of the sheath 706.

As shown in FIG. 7, the drive shaft 703 extends at least partially through the proximal assembly tube 720, and the centralizer 704 encompasses at least a portion of the proximal assembly 710. The drive shaft 703 is coupled at a proximal end thereof to a motor 740 configured to operate to cause the drive shaft 703 to rotate, which causes the impeller 715 to also rotate. The motor 740 can have any suitable configuration and it can be positioned outside of the patient's body when the system 700 is at least partially implanted into the patient's body. In some implementations, the motor 740 can be positioned adjacent to the patient's body, in the vicinity of the incision made to insert the catheter into the patient's body. Additionally, the motor 740 can be detachable from the drive shaft 703 such that the motor 740 is releasably and replaceably coupled to the drive shaft 703. Thus, the motor can be reusable. Furthermore, in some implementations, the motor can be implantable, in which case it may or may not be associated with an implantable power source.

As shown schematically in FIG. 7, the catheter system 700 can be coupled to a controller device 725 configured to control operation of the motor 740. For example, the controller device 725 can receive information (e.g., fluid pressure measurements) acquired by sensor(s) associated with the catheter system 700 and the controller device 725 can control operation of the motor 740 (e.g., increase or decrease motor RPM) based on the monitored blood pressure. The motor 740 can be controlled such that operation of the system attains a certain desired blood pressure in a certain area in the patient's body, e.g., at an outflow port of a lymphatic duct, such as a right lymphatic duct. The motor 740 can be controlled using any suitable mechanism(s). For example, a closed circuit control mechanism can be used to adjust a speed of rotation of one or more components of the motor 740, to thereby control the speed of the impeller 715. The control mechanism can operate such that the motor 740 is cause to increase its RPM to thereby lower a pressure in the low pressure zone. The pressure in the low pressure zone can be monitored using one or more suitable pressure sensors.

FIGS. 9A and 9B show the distal assembly 718 that includes the impeller assembly 705 having the impeller 715 that is driven by a motor (e.g., a motor 740 of FIG. 22) to which the impeller 715 is coupled via the drive shaft 703. As shown in FIG. 9B (and also shown in FIG. 19), the restrictor 712 has an inner lumen 717 that is configured to allow fluid (e.g., blood) to pass therethrough. An outer portion 721 of the restrictor 712 surrounding the lumen 717 is selectively deployable (e.g., inflatable), and the outer portion can be coupled to an inflation lumen configured to cause the outer portion 721 to inflate. The outer portion 721 can be in the form of a compliant balloon, and the inner lumen 717 can be formed when the balloon is inflated. Furthermore, in some embodiments, the inner lumen can be defined by a separate tubular structure having the outer portion 721 coupled circumferentially thereto.

Figure 10B:
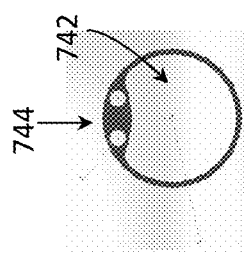
FIG. 10B is cross-section of a portion of the proximal assembly of FIG. 10A.
Figure 10A:
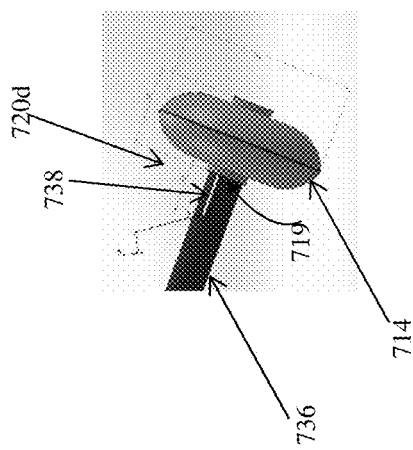
FIG. 10A is a perspective view of a portion of a proximal assembly of the implantable system of FIG. 7.

FIG. 10A illustrates a portion of the proximal assembly 710. As shown, a distal end 720d of the proximal assembly tube 720 can include or can be coupled to a flow regulator component 736. As shown in FIG. 10A, the flow regulator component 736, which is disposed proximally to the proximal restrictor 714, includes opening sections or openings 738 that allow a blood flow (e.g., a jugular blood flow) to enter through the openings 738. The flow regulator component 736 can include one or more (e.g., four) openings, though it should be appreciated that any suitable number of openings can be formed. In at least some embodiments, once the implantable catheter system 700 is implanted in the patient's body and the restrictors 712, 714 are activated, the proximal assembly 710 can regulate the jugular flow and pressure to create a low pressure zone between the restrictors 712, 714. In particular, once the impeller 815 is activated, the jugular flow is caused to enter through the openings 738 of the flow regulator component 736 and into a gap 719 (marked schematically in FIG. 10A) between an outer wall of the catheter tube 702 and an inner wall of the proximal restrictor 714 defining an inner lumen (not shown) of the proximal restrictor 714. The volume of the jugular flow is thus reduced. In at least some embodiments, the jugular flow in the range from about 100 ml/min to about 600 ml/min enters the gap 719. In the illustrated embodiments, the proximal restrictor 714 has the inner lumen that can be similar to a lumen of the distal restrictor, such as, e.g., lumen 717 in FIG. 19. A diameter of the proximal restrictor's lumen can be smaller than a diameter of the inner lumen of the distal restrictor, as shown in FIGS. 7 and 8. The proximal restrictor 714 of the proximal assembly 710 can be in the form of a balloon of a suitable size. In at least some embodiments, the balloon's diameter is from about 10 mm to about 25 mm, though it should be appreciated that the balloon can have any suitable diameter.

FIG. 10B shows an example of a cross-section of the proximal assembly 710 taken at the flow regulator component 736. The flow regulator component 736 can be part of the distal end of the proximal assembly tube 720 (FIG. 8). As shown in FIG. 10B, the proximal assembly 710 includes an inflation lumen 742 that assists in inflation of the proximal restrictor 714. In at least some embodiments, a diameter of the inflation lumen 742 is from about 0.2 mm to about 0.6 mm, though it should be appreciated that the inflation lumen 742 can have any suitable diameter. The proximal assembly 710 can have associated therewith (e.g., coupled thereto in a suitable manner) one or more pressure sensor(s) that are configured to acquire pressure measurements at the jugular and/or subclavian veins. In pathological conditions such as, for example, ADHF, the central venous pressure (CVP) can be about 15 mmHg and, in some cases, it can vary from about 10 mmHg to about 40 mmHg. When the patient has decongested, the pressure during inspiration can be lower—e.g., about −10 mmHg; and when the patient is congested and performs, for example, a Valsalva maneuver, the pressure can be higher—e.g., about 40 mmHg. The low pressure zone reduces the CVP locally at the site of the thoracic duct outflow to normal levels, such as in a range from about 2 mmHg to about 6 mmHg. In some embodiments, including any of the embodiments described herein in connection with any of catheter systems, the pressure of about 5 mmHg is maintained in the low pressure zone. As shown in FIG. 10B, the inflation lumen 742 can have one or more separate lumens 744 formed therein, which can be, for example, an inflation lumen in fluid (or air, or other gas) communication with the restrictors and configured to cause the restrictors to be activated, and a control lumen including one or more pressure sensors. The inflation lumen 742 can include any other lumens. Additionally, in some embodiments, the inflation lumen 742 can include ports that allow flushing the lumen 742.

FIGS. 13-22 illustrate examples of various components of the catheter system 700. Thus, FIG. 13, illustrating the catheter shaft or tube 702 in cross-section, shows that the catheter tube 702 includes an inner lumen 746 configured to hold the drive shaft 703. The inner lumen 746 of the catheter tube 702 can also include one or more inflation lumens 748. The lumen 746 can include any other lumens. The catheter tube 702 can have associated therewith (e.g., coupled thereto in a suitable manner) one or more pressure sensor(s) that are configured to acquire pressure measurements at the jugular and/or subclavian veins. The pressure can be about 15 mmHg and, in at least some embodiments, it can vary from about 10 mmHg to about 40 mmHg. When the patient has decongested blood flow, the pressure during inspiration can be lower—e.g., about 10 mmHg; and when the patient is congested and performs, for example, a Valsalva maneuver, the pressure can be higher—e.g., about 40 mmHg. The catheter tube 702 can have various configurations. In some embodiments, the catheter tube 702 can be flexible such that it can bend, if required. For example, in at least some embodiments, the catheter tube 702 is resiliently bendable.

Figure 14:
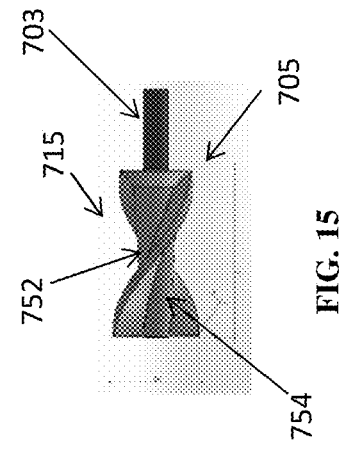
FIG. 14 is a cross-sectional view of a drive shaft of the implantable catheter system of FIG. 7.

FIG. 14 illustrates one embodiment of a cross-section of the drive shaft 703. As shown, the drive shaft 703 has an inner limner 750 extending therethrough that can receive a guidewire therein. The drive shaft 703 can be in any suitable form—for example, in at least some embodiments, it can be in the form of a torque coil cable having a lumen extending therethrough. In some embodiments, the drive shaft can be associated with a sleeve that is configured to house the drive shaft so as to reduce friction and influence of heat and wear.

Figure 15:
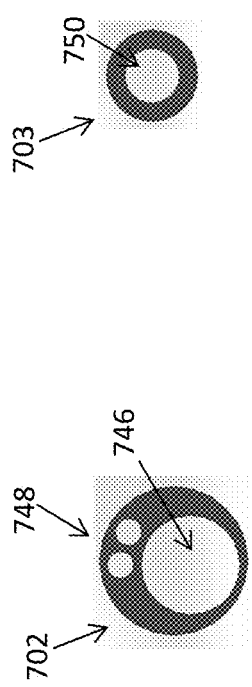
FIG. 15 is a side view of an impeller of the implantable catheter system of FIG. 7.

FIG. 15 shows the impeller assembly 705 including the impeller 715. The impeller 715 can have various configurations, and it should be appreciated that the impeller 715 is shown in FIG. 15 by way of example only. The impeller 715 is configured to operate to pump fluid, such as blood, outwards from a center of rotation. For example, the impeller 715 can pump blood from a center portion of the catheter system 700 to thereby drive the blood distally and outward towards a perimeter of the vessel in which the catheter system 700 is implanted. In this embodiment, as shown in FIG. 15, the impeller 715 is in the form of a rotatable component having one or more semi-spiral blades 754 extending axially along an impeller shaft or body 752 that extends along a longitudinal axis of the draft shaft 703. The impeller body 752 can be coupled to the distal end of the draft shaft 703 in any suitable manner. As shown in FIG. 15, the spiral blades 754 are wound around the impeller body 752 such that the impeller 715 has generally a bow-like shape as viewed along the longitudinal axis of the draft shaft 703. In some embodiments, the impeller 715 can have more than one (e.g., two, three, four, or greater than four) blades 754 extending from the impeller body 752. The impeller body 752 includes an inner lumen (not shown) extending therethrough that is configured to receive a guide wire therethrough. It should be appreciated that the impeller 715 can have any other configurations, including a configuration having one blade wound around a shaft in a spiral-like manner, a configuration having any type of semi-spiral or spiral blades, etc.

The impeller 715 can have any suitable dimensions. For example, in some embodiments, a diameter of the largest area of the impeller 715, as measured in a plane perpendicular to the longitudinal axis of the drive shaft 703, can range from about 3 mm to about 5 mm. A length of the impeller 715 can range from about 4 mm to about 8 mm. It should be appreciated, however, that the impeller can have any other suitable dimensions, as the described embodiments are not limited in this respect. Also, the impeller can have any suitable configuration and it can be part of any suitable pump. Regardless of its specific configuration, the impeller 715 is driven via a suitable motor that rotates the drive shaft 703 having the impeller 715 coupled to the distal end thereof. In some embodiments, the impeller can be driven to a rotation speed of less than about 25000 RPM (revolutions per minute). In some embodiments, the operation of the impeller causes the blood to flow at a rate of about 800 ml/min, and the pressure gradient is about 20 mmHg. The rotational speed can be selected to reduce hemolysis risk.

As mentioned above, FIG. 16 illustrates the impeller housing or cage 730. The impeller housing 730 that also house a bearing system. Regardless of its specific configuration, the impeller housing 730 is configured so as to pass blood from its proximal end to a distal end. The blood is passed through the openings 732. The impeller housing 730 can have any suitable dimensions. In some embodiments, the impeller housing dimensions follow impeller dimensions, such that only a small gap (e.g., 0.05 mm-0.2 mm) exists between the impeller (e.g., an outer surface of widest portion(s) of the impeller such as, e.g., impeller 715 of FIG. 15), and the impeller housing 730.

Figure 17:
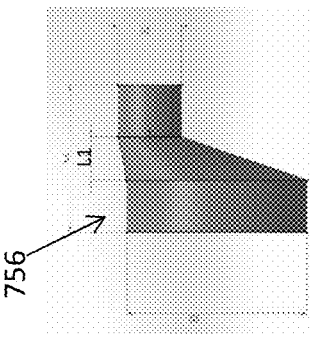
FIG. 17 is a perspective view of an embodiment of an impeller housing.

FIG. 17 illustrates an alternative embodiment of an impeller housing 730' of an indwelling catheter system. In this example, the impeller housing 730' includes an extension 731 configured to support the catheter while keeping a suction lumen of the distal restrictor fully open.

Figure 18:
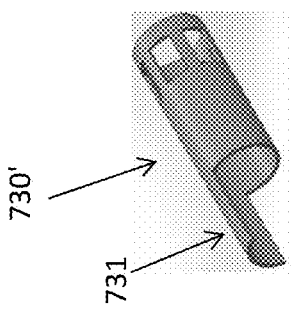
FIG. 18 is a side view of a membrane of an implantable catheter system.

FIG. 18 illustrates a membrane 756 (e.g., membrane 716 shown in FIGS. 7 and 8). In this example, the membrane 716 is a conical membrane, though it can have other configurations. The conical membrane can allow diffusing the blood flow from an isolated zone to the impeller. The conical shape facilitates delivering the flow smoothly to the impeller, which reduces resistance to the flow. The membrane 756 can have any suitable dimensions. For example, in at least one embodiment, a portion L1 of the membrane 756 having a conical shape, shown in FIG. 18, can have a length in a range from about 2 mm to about 10 mm.

Figure 20:
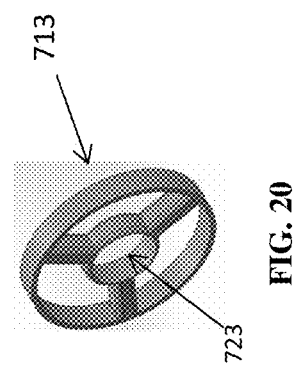
FIG. 20 is a perspective view of a drive shaft holder associated with restrictor of FIG. 19.
Figure 19:
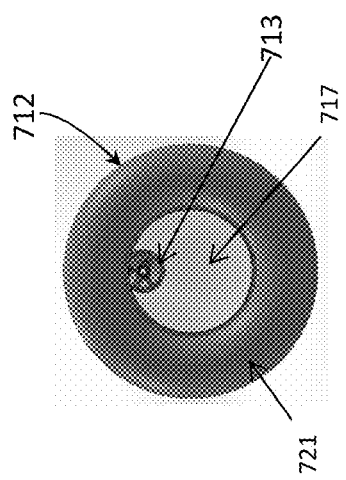
FIG. 19 is a cross-sectional view of a restrictor of the implantable catheter system of FIG. 7.

FIG. 19 shows the distal restrictor 712 that is, in the illustrated embodiments, is generally doughnut-shape having an inner lumen 717 that allows for passage of fluid therethrough. As shown, the distal restrictor 712 has a holder 713 (also shown in FIG. 20) coupled thereto. In this example, the holder 713 is in the form of a "Mercedes-wheel" shaped holder. As shown in FIGS. 19 and 20, the holder 713 has an opening 723 configured to hold the catheter tube 702 and the drive shaft 703 received within the catheter tube. The outer portion 721 of the restrictor 712 surrounding the lumen 717 is selectively deployable (e.g., inflatable), and the outer portion can be coupled to a deployment or inflation lumen configured to cause the outer portion 721 to inflate. This configuration of the holder 713 allows holding the drive shaft 703 centralized and also keeps the impeller 715 in place. The distal restrictor 712 can have any suitable size. In at least one embodiment, a diameter of the restrictor, in the deployed (inflated) configuration is in a range from about 14 mm to about 30 mm. Although not shown in FIG. 19, in the illustrated embodiments, the distal restrictor 712 has a membrane coupled thereto that directs a fluid flow towards the impeller. In addition, a proximal restrictor can be configured in a similar manner.

Figure 21:
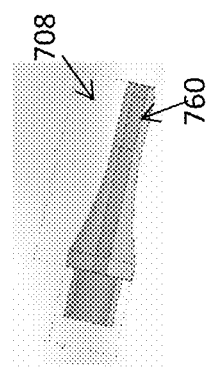
FIG. 21 is a side, partially transparent view of a distal tip of the implantable system of FIG. 7.

FIG. 21 shows a distal tip 708 of the catheter system 700, which can be an atraumatic tip that allows a gentle insertion of the catheter system 700 into a vessel in a patient's body. The distal tip 708 can have an inner lumen 760 extending therethrough that is configured to receive a guide wire therein. The distal tip 708 can have its proximal end coupled to an impeller housing—e.g., any of the housings 730 (FIG. 16), 730' (FIG. 17), or the impeller housing having any other configuration. The distal tip 708 can have any suitable dimensions. For example, in some embodiments, a length of the distal tip 708 can vary in a range from about 10 mm to about 30 mm.

Figure 22:
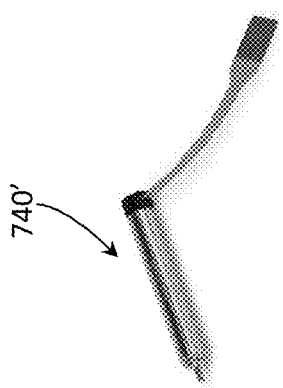
FIG. 22 is a perspective view of a motor configured to drive an impeller of an implantable system.

FIG. 22 illustrates one embodiment of a motor 740' which is configured to deliver a driving force to the impeller through the drive shaft. The motor 740' (e.g., motor 740 of FIG. 7) can be, for example, an extracorporeal motor. However, it should be appreciated that, in some implementations, the motor 740' can be implantable. In some embodiments, a shaft of the motor 740' that is configured to be driven and to cause the rotation of the drive shaft. The motor shaft can have a lumen extending therethrough (not shown) that can receive therein a guide wire. In some embodiments, the motor shaft is associated with a mechanism configured to assist in insertion and removal of the guide wire from the motor shaft's lumen. The motor 740' can have any suitable dimensions. In some embodiments, a diameter of the motor 740' can vary in a range from about 4 mm to about 30 mm, and a length of the motor 740' can vary in a range from about 10 mm to about 50 mm. It should be appreciated that the components that can be included in the catheter system 700, or other catheter systems in accordance with the described subject matter, are shown in FIGS. 13 to 22 by way of example only, and that the dimensions of the components are also shown by way of example only.

Referring back to FIGS. 11 and 12, FIG. 11 illustrates an embodiment of a catheter system 800 for treating edema with a straight multi-lumen configuration implanted in a patient's body. FIG. 12 shows a similar catheter system 900 implanted in a patient's body, the system 900 having a bent or kink 901 of a catheter tube between proximal and distal restrictors. The systems 800, 900 can have any of the components illustrated in connection with FIGS. 7 to 10B and FIGS. 13 to 22. It should be noted that the thoracic duct is not shown in FIGS. 11 and 12. In this example, each of the systems 800, 900, as well as other catheter systems described herein, can be implanted in the patient such that the distal restriction member is disposed in the innominate vein, and the proximal restriction member is disposed in the jugular vein, e.g., at a distance of about 1.5 cm from the bifurcation of the jugular and subclavian veins. It should be appreciated, however, that the restriction members can be implanted in other manners.

Figure 11:
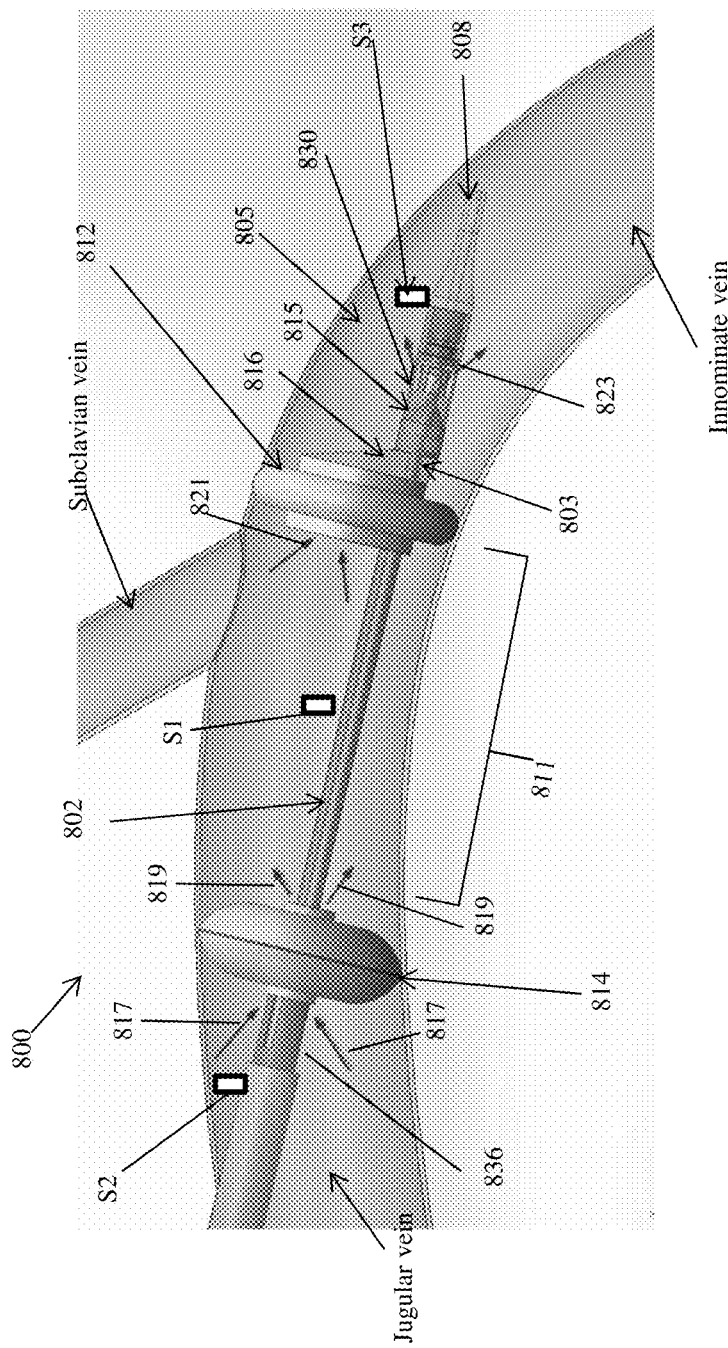
FIG. 11 is a perspective view of an embodiment of an implantable catheter system, showing the implantable system implanted in a patient's body.
Figure 12:
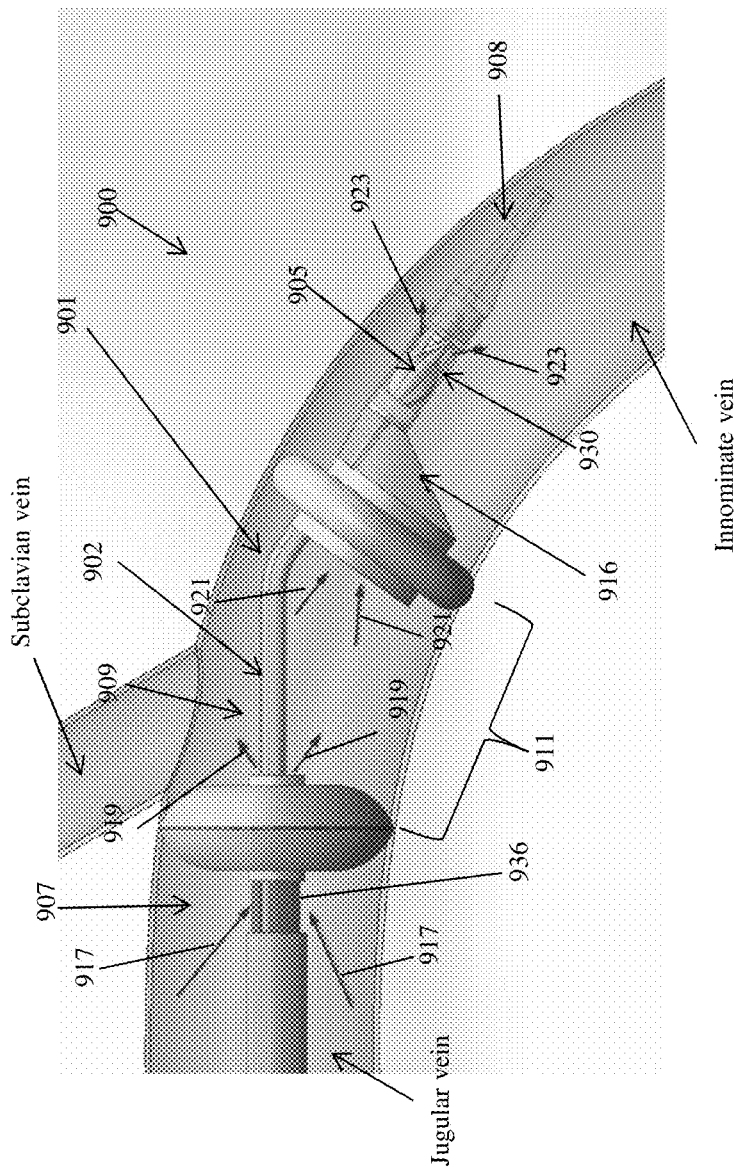
FIG. 12 is a perspective view of another embodiment of an implantable catheter system, showing the implantable system implanted in a patient's body.

As shown in FIG. 11, the catheter system 800 for treating edema includes an indwelling catheter tube or shaft 802 configured to be placed within a vein of a patient. The indwelling catheter shaft 802 has a lumen extending therethrough that receives a drive shaft 803 therein, wherein a distal portion of the drive shaft 803 is operatively coupled to an impeller 815. The catheter system 800 also includes a first selectively deployable restriction member adjacent 812 that is proximal to the impeller 815, and a distal atraumatic tip 808 extending distally from an impeller housing 830 that encompasses the impeller 815. As shown, the first restriction member 812, which can be in the form of a distal balloon, has a membrane 816 operatively coupled thereto and configured to direct fluid from an upstream side of the first restriction member 812 to the impeller 815. Similar to membrane 716 (FIG. 9A). The membrane 816 can be a conical (distally tapered) membrane defining a tunnel therethrough, though the membrane can have any other suitable configuration. The catheter 800 also includes a second selectively deployable restriction member 814 (e.g., in the form of a proximal balloon) proximal to the first restriction member 812.

In some embodiments, the catheter system 800 includes one or more pressure sensors. For example, as shown in FIG. 11, the catheter system 800 can include a pressure sensor S1 disposed between the distal and proximal restriction members 812, 814. Additionally, the catheter system 800 can include one or both of a pressure sensor S2 disposed proximally to the proximal restriction member 814 and a pressure sensor S3 disposed distally to the distal restriction member 812. The sensors S1, S2, S3 can be coupled to the catheter system 800 in any suitable manner. It should be appreciated that the S1, S2, S3 are shown in FIG. 11 schematically for illustration purposes only, and one or more of the sensors S1, S2, S3 can be disposed within a lumen, such as control lumen extending through the system, such that the sensor will not be visible in the manner as shown in FIG. 11. Furthermore, in some implementations, the sensors S1, S2, S3 may not be coupled to the catheter system 800. The sensors can transmit acquired data, via a wireless or wired connection, to a suitable controller that processes the data. A motor (e.g., motor 740 in FIG. 22, or any other motor) configured to control operation of the impeller assembly 805 can be controlled based on the pressure data acquired by the sensors.

The second restriction member 814 is operatively coupled to a flow regulation component 836 configured to direct a controlled volume of fluid from an upstream side 807 of the second restriction member 814 to a downstream side 809 of the second restriction member 814. For example, the jugular flow enters through radial openings formed in the flow regulation component 836 (which can be configured similarly to flow regulation component 736 of FIG. 10A) and follows to the gap between the catheter shaft and an inner lumen of the second restriction member 814. In this way, as shown by arrows in FIG. 11, blood flows from the upstream side 807 of the second restriction member 814, enters a portion of the catheter between the first and second restriction members 812, 814, and is directed to the downstream side 809 of the second restriction member 814. The components through which the blood flows have a common lumen extending therethrough. The impeller 815 is rotated via a draft shaft by a suitable motor. The impeller 815, as well as other components of the system 800, can be similar to respective components of the system 700 shown in FIGS. 7, 8, 9A, and 9B, and their description is therefore not repeated herein.

In FIG. 11, the first and second restriction members 812, 814 are shown in the deployed configuration. The first restriction member 812 can be, for example, doughnut shaped and it can allow for a maximum free flow of fluid through its lumen and for minimal resistance to the fluid flow. As shown in FIG. 11, the first and second restriction members 812, 814 can be implanted so as to create a low pressure zone 811 therebetween. In use, the system 800 is operated so as to regulate a fluid flow in the low pressure zone 811. Transporting the fluid through the localized low pressure zone 811 can maintain a constant pressure within the low pressure zone. The second (proximal) restriction member 814 is configured to regulate the jugular flow, and it is configured to restrict the blood flow. The conical membrane 816 can allow for diffusing the fluid flow from the low pressure zone 811 to the impeller 815.

In the example of FIG. 11, when the impeller 815 is activated, the blood flows (arrows 817) from a proximal side of the proximal restriction member 814, through the lumen in the restriction member 814, and exits (arrows 819) the restriction member 814 distally into the low pressure zone 811. The blood then flows towards (arrows 821) and through a lumen of the distal restriction member 812, and the bloods exits (arrows 823) the catheter system 800 through openings in an impeller housing 830 that houses the impeller 815 of an impeller assembly 805. The membrane 816 coupled to the distal restriction member 812 directs the blood flow from the lumen of the distal restriction member 812 to the impeller 815.

The catheter system 900 shown in FIG. 12 can be configured similar to system 800 of FIG. 11. Thus, as shown, the catheter system 900 includes a catheter shaft or 902, distal and proximal selectively deployable restrictors 912, 914 disposed at least partially around the tube 902, an impeller system 915 including an impeller housing 930 and an impeller 905, and a distal atraumatic tip 908 extending distally from the impeller housing 930. In the example of FIG. 12, when the impeller 915 is activated, the blood flows (arrows 917) from a proximal side of the proximal restriction member 914, through a lumen in the restriction member 914, and exits (arrows 919) the restriction member 914 distally into the low pressure zone 911. The blood then flows towards (arrows 921) and through a lumen of the distal restriction member 912, and the bloods exits (arrows 923) the catheter system 900 through openings in a cage or impeller housing 930 that houses the impeller 915 of an impeller assembly 905. The membrane 916 coupled to the distal restriction member 912 directs the blood flow from the lumen of the distal restriction member 912 to the impeller 915. Although not shown in FIG. 12, similar to system 800 of FIG. 11, the system 900 (as well as other catheter systems described herein) can include one or more pressure sensors, such as, for example, one or more of the sensors S1, S2, S3 (FIG. 11).

It should be appreciated that the described embodiments include an implantable catheter system that can have any of the components of the catheter systems 700, 800, and 900 (which, in turn, can be similar to one another). Also, any of the components of one of the catheter systems 700, 800, and 900 can be included into another one of the catheter systems 700, 800, and 900.

Any of the catheter systems described herein can be associated with any other components. For example, a catheter system can include a controller that can be configured to be in electronic communication with at least one pressure sensor (not shown). A person skilled in the art will appreciate that a variety of suitable sensors can be used for monitoring pressure, such as central venous pressure (CVP) or other fluid pressure sensors, and blood pressure sensors. The pressure sensor(s) can be implanted in the patient as part of the impeller, implanted in the patient as a separate component from the impeller, or the at least one pressure sensor can be located external to the patient, such as by being on a skin surface thereof. If not already a part of the impeller so as to be in electronic communication therewith, the at least one pressure sensor can be configured to be in electronic communication with the impeller over a communication line such as a wired line or a wireless line.

In an exemplary embodiment, three pressure sensors can be implanted in the patient. One of the pressure sensors can be implanted between the first and second restriction members as to be in the low pressure zone. Another pressure sensor can be implanted in the vein proximal to the second restriction member, and another pressure sensor can be implanted in the vein distal to the first restriction member, so as to be in the higher pressure zones. The sensors can allow a pressure differential to be determined between the low pressure zone and the higher pressure zone. In other embodiments, another number of pressure sensors can be implanted in the patient (e.g., one, three, four etc.) and/or the pressure sensor(s) can be implanted at other locations.

The catheter can include at least one lumen (not shown) configured to facilitate use of the pressure sensor(s), for example to facilitate placement of the pressure sensor(s) and/or to be filled with a fluid such as saline to allow for external pressure measurement.

In addition to or instead of the one or more pressure sensors, the controller can be configured to be in electronic communication with at least one other type of sensor (not shown) configured to sense a parameter other than pressure. Examples of sensors that can be used to measure a parameter other than pressure include radio frequency transmitters and receivers, fluid sensors, bioimpedance sensors, heart rate sensors, breathing sensors, activity sensors, and optical sensors. Examples of the measured parameter include fluid amount (e.g., as measured by a fluid sensor, such as a fluid sensor placed in a lung to sense fluid amount in the lung), bioimpedance (e.g., as measured by a bioimpedance sensor), heart rate (e.g., as measured by a heart rate sensor), breathing rate (e.g., as measured by a breathing sensor), patient activity level (e.g., as measured by an activity sensor), and organ dimension (e.g., as measured by an optical sensor). The sensor can be implanted in the patient as part of the pump, implanted in the patient as a separate component from the pump (e.g., implanted in an interstitial space around a lung, implanted at a junction of a right subclavian vein of a patient and an internal jugular vein of the patient, implanted at a junction of a left subclavian vein of a patient and an internal jugular vein of the patient, etc.), or the sensor can be located external to the patient, such as by being on a skin surface thereof.

The controller can include any type of microprocessor or central processing unit (CPU), including programmable general-purpose or special-purpose microprocessors and/or any one of a variety of proprietary or commercially available single or multi-processor systems. The controller can be a component of a control system that includes any number of additional components, such as a memory configured to can provide temporary storage and/or non-volatile storage; a bus system; a network interface configured to enable the control system to communicate with other devices, e.g., other control systems, over a network; and an input/output (I/O) interface configured to connect the control system with other electronic equipment such as I/O devices (e.g., a keyboard, a mouse, a touchscreen, a monitor, etc.) configured to receive an input from a user. The controller can be configured to receive user input thereto to control any of a variety of aspects related to the catheter, such as speed of the motor and ideal range of pressure for the low pressure zone.

In use, the catheter system can be attached to a patient near an incision point. One or more electronic cables can be connected to a multiuse console that includes a motor controller, a pressure sensor amplifier, firmware with data acquisition system, power supply, touch screen monitor, and any other suitable components.

In some embodiments, a method of implanting a catheter system involves delivering a sterile catheter kit to a clinical site in its open state, in which a distal portion of a distal assembly is unsheathed. Prior to an implanting procedure, a user (e.g., a physician assistant or any other medical professional) can insert the distal assembly into a sheath lumen, e.g., by using a handle Tuhy. The catheter is then inserted by the physician over a guide wire into the jugular vein (e.g., posterior approach). Once it is confirmed (using, e.g., an ultrasound technique) that the catheter is located in the jugular vein, the operator can un-sheath the distal unit in two consecutive steps. First, the distal balloon can be un-sheathed and positioned in the innominate vein just past the subclavian drainage. Second, the proximal balloon is disposed in the jugular vein, above the subclavian vein.

The guide wire can be pulled out and the sheath is fixated to the skin in a location that allows the maximal axial adjustment of the assembly. After the fixation, the centralizer is positioned, and an electric cable is connected. The motor is activated (e.g., using a controller that can be accessed via a console graphical user interface (GUI)) and causes the distal and proximal balloons to inflate. The distal balloon can be inflated prior to inflating the proximal balloon. The CVP can be measured through a sheath luer. The pressure can be adjusted using a catheter system handle by bringing a proximal assembly of the catheter assembly closer to the sheath or away from the sheath (or any other mechanism). The motor can drive the impeller to define a low pressure zone by causing fluid to be pumped through the catheter system. In this way, the system can operate automatically to keep the low pressure zone (or "isolated zone") at a nominal pressure value of, for example, 2.5±2.5 mmHg. This can be done be controlling the motor RPM.

In general, the described catheter system is configured to seal a zone at the bifurcation of the patient's jugular and subclavian veins using the distal and proximal balloons. As the impeller is operated, the blood is directed from the low pressure zone such that the pressure inside that zone is reduced. The motor receives feedback from one or more pressure sensors, and the pressure can be regulated by the motor RPM. The CVP can be adjusted by a regulation mechanism at the proximal assembly.

The described systems (e.g., any of the systems 700, 800, 900) provide various advantages over existing systems. For example, because a restrictor in the form of a balloon is inflated over the entire vessel perimeter and the suction lumen is an integrated part of the balloon, the vessel is prevented from collapsing on the suction lumen and thus blocking the blood entrance. Furthermore, since there is a free passage between the isolated zone and the innominate vein, in case of a malfunction or unintentionally stopping of the system, a pressure elevation event will be prevented in the isolated zone and stagnation of blood can be prevented.

The conical shape of the membrane, the large suction diameter and the minimal length of flow up to the impeller can provide a minimal resistance to blood flow during suction and therefore increases the impeller ability to pump the required amount of blood at a lower rotational speed as compared to other systems. Mechanical hemolysis can occur due to high shear stresses on the blood cells. Thus, the lower the rotational speed of the impeller, the lower the shear stress, which increases safety of the catheter system. Additionally, a lower rotational speed provides a wider range of flow rate and reduces a possibility of the system not being able to reduce the pressure because of a rotational speed limitation.

As another advantage, the described catheter system can eliminate a need for a conduit coupled between the jugular vein and the innominate and allows for pressure regulation in the jugular vein. Thus, unavoidable pressure elevation of the jugular vein does not take place. Furthermore, the proximal and distal balloons are configured to be inflated using separate mechanisms of the proximal and distal assemblies, respectively, a distance between the proximal and distal balloons can be determined and adjusted. This provides an additional flexibility of the system which allows adjusting the system to the specific anatomy of a patient.

Figure 23B:
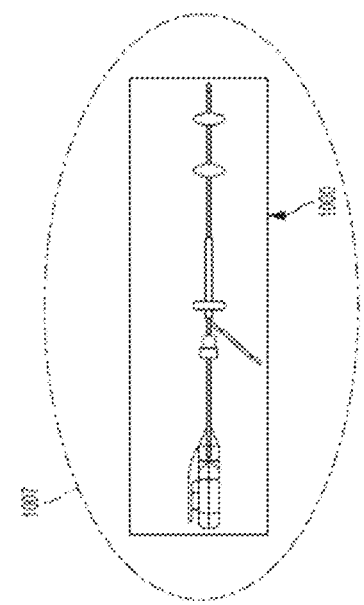
FIG. 23B is an enlarged side view of the implantable catheter system of FIG. 23A.
Figure 23A:
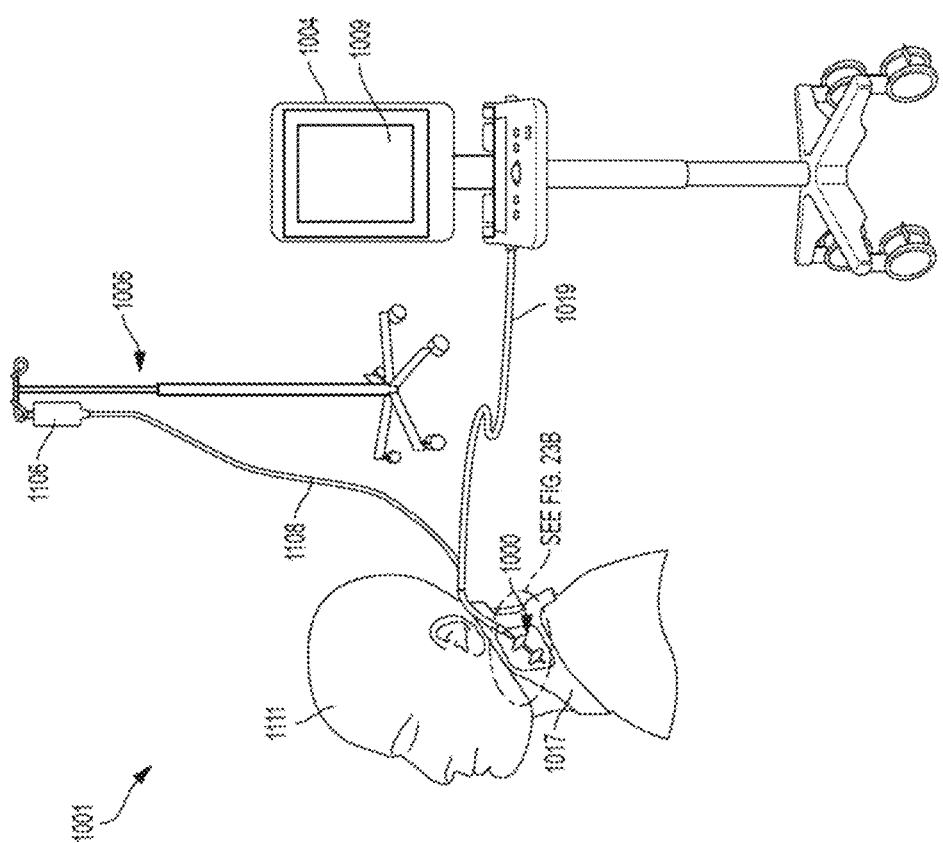
FIG. 23A is a perspective view of a system in accordance with some embodiments, the system including an implantable catheter system shown implanted in a patient.

In some embodiments, a catheter system is associated with an infusion/purging system configured to infuse fluids into a certain portion of the catheter system to thereby prevent an undesirable event of the blood entering that portion. Thus, FIG. 23A illustrates schematically a system 1001 in which some embodiments can be implemented. The system 1001 includes a catheter system 1000 that can be at least partially implanted into a patient 1111, a control system 1004 coupled to the catheter system 1000, and an infusion system 1006. The patient 1111 has an incision through which the catheter system 1000 is delivered into the patient. As shown in FIG. 23A, the catheter system 1000, which is also shown enlarged in an inset 1007 in FIG. 23B, can be coupled to a fixture or holder device 1017 that is worn by the patient 1001. The holder device 1017 can have any suitable configuration that allows it to assist in maintaining a position of the catheter system 1000 with respect to a patient's body. In this example, the holder device 1017 is in the form of a collar-like device configured to be coupled to the patient's neck. The control system 1004, which is, in this example, in the form of a console device, has various components, non-limiting examples of which include a motor controller, a pressure sensor amplifier, a processing hardware including a data acquisition and processing system, and a power supply. The control system 1004 includes processors configured to acquire, process, and analyze data collected during operation of the catheter system 1000.

As shown in FIG. 23A, the control system 1004 includes a display 1009 that can be a touch screen display. The display 1009 is configured to display information related to operation and control of the catheter system 1000. The control system 1004 can be coupled to the catheter system 1000 via a cable 1019; however, in some embodiments, the connection can be wireless such that the control system 1004 or a part thereof can be located remotely to the catheter system 1000. The infusion system 1006, having an infusion container 1106 (e.g., a bag or any other type of a container), is configured to allow fluid to access a space between a drive shaft 1003 (shown in FIG. 25) and a sleeve of the catheter system 1000 that encloses at least a portion of the drive shaft 1003, as discussed in more detail below.

Figure 24:
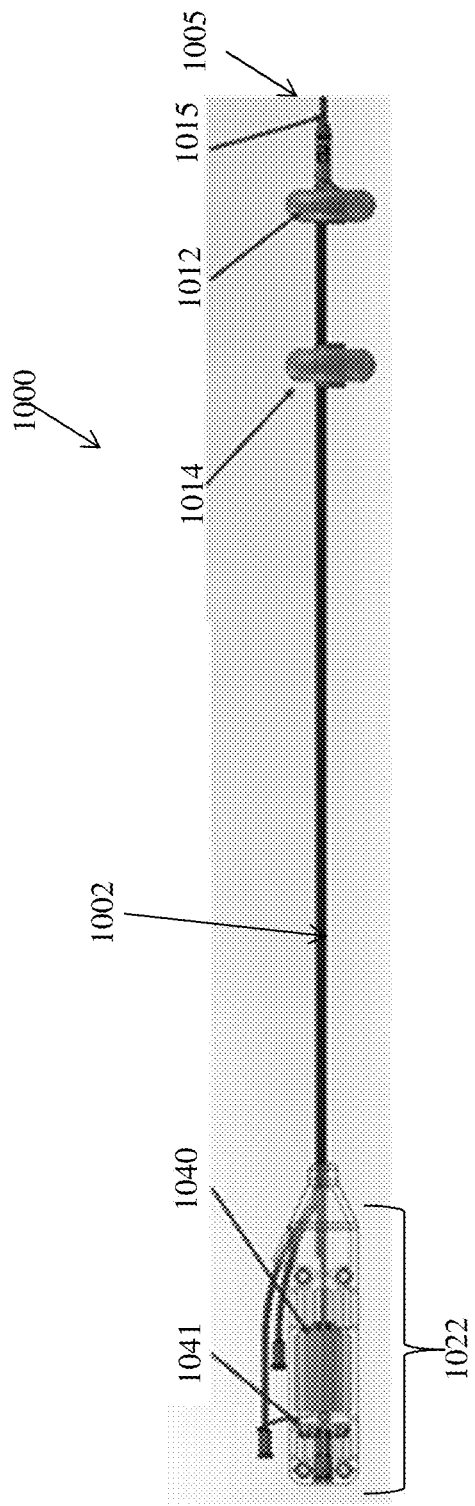
FIG. 24 is a partially transparent side view of the implantable catheter system of FIG. 23A.

FIG. 24 illustrates the catheter system 1000 in more detail. As shown in FIG. 24, the catheter system 1000 includes a catheter tube 1002, distal and proximal restrictors or restriction members 1012, 1014, a distal tip 1008, and an impeller system 1005. A proximal portion 1022 of the catheter system 1000 includes, among other components, a motor 1040 and fans 1041. The motor 1040 can be similar to motor 740 (FIG. 7). The proximal portion 1022 can be in the form of a handle at least a portion of which can be held by a user when the catheter system 1000 is inserted into the patient's body. Similar to distal restrictor 712 (FIGS. 7, 8, and 9A), the distal restriction member 1012 has a membrane 1016 coupled thereto. In this embodiment, the distal and proximal restriction members 1012, 1014 are in the form of expandable elements, such as balloons, each of which is configured to at least partially restrict a vessel (e.g., a vein) of a patient in which it is implanted. Thus, the distal and proximal restriction members 1012, 1014 are moveable between a pre-activated (e.g., not expanded or non-inflated) and activated (e.g., expanded or inflated) configurations. In the illustrated embodiments, a diameter of the inner lumen of the distal restriction member 1012 can be greater than a diameter of an inner lumen of the proximal restriction member 1014. In this way, whereas the proximal restriction member 1014 reduces a blood flow that passes therethrough (e.g., causes the jugular flow to reduce), the distal restriction member 1012 allows a larger volume of the blood flow to pass therethrough. Furthermore, in some implementations, the distal restriction member 1012 allows blood to flow freely through its lumen.

FIG. 25 shows a distal portion of the catheter system 1000 in more detail. Thus, as shown, the impeller system 1005 includes an impeller 1015 disposed within an impeller housing 1030 that also includes a bearing system 1013 shown separately in FIG. 26A. The membrane 1016 coupled to the distal restriction member 1012 has a conically-shaped portions, as membranes in other embodiments described herein. It should be appreciated, however, that the membrane 1016 can additionally or alternatively have other configurations.

FIG. 26B illustrates one embodiment of a catheter shaft or tube 1002' of a catheter system in accordance with the described techniques, such as, for example, the catheter tube 1002 of FIG. 24. As shown, the catheter tube 1002', shown in FIG. 26B in cross-section, includes an inner lumen 1046' configured to receive a sleeve and a drive shaft, with the drive shaft received within a sleeve's lumen. In this example, the catheter tube 1002' also includes lumens 1048. In this embodiment, the lumens 1048 include a proximal restrictor inflation lumen, a distal restrictor inflation lumen, a pressure sensor lumen, and an infusion (or "purge") lumen. These four lumens can be disposed in any suitable order within the catheter tube 1002'. Furthermore, it should be appreciated that the catheter tube 1002' can have other lumens, and it can have fewer or greater than four lumens.

FIG. 26C illustrates the proximal restriction member 1014 having an inner lumen 1019 configured to receive the drive shaft 1003 therethrough. The lumen 1019 is configured to pass fluid (e.g., blood) therethrough. In some embodiments, a diameter of the fluid flow lumen 1019 of the proximal restriction member 1014 in an activated (e.g., inflated) configuration is less than a diameter of a fluid flow lumen of the proximal restriction member 1012 in an activated (e.g., inflated) configuration.

As in the other embodiments described herein, the catheter system 1000 is configured to reduce pressure in a specified partially isolated zone, which becomes a low pressure zone. The isolated zone is defined between the distal and proximal restriction members 1012, 1014 when the restriction members 1012, 1014 are implanted in the patient's body and are activated (e.g., inflated). A blood pressure between the implanted distal and proximal restriction members 1012, 1014 is reduced when the blood is pumped out at a higher rate than can be supplied by the surrounding veins. The pumping of the blood can be accomplished by using a motor that is configured, when activated, to rotate a drive shaft 1003 inside a sleeve component. A distal end 1003*d* of the drive shaft 1003 is coupled to the impeller 1015 that is supported by the bearing system 1013 disposed within the impeller holder or housing 1030. The impeller 1015, which can be similar to impeller 715 (FIG. 15), is configured to pump blood in an axial direction through the membrane 1016 and to discharge the blood radially through radial openings in the impeller housing 1030. The impeller housing 1030 is configured similar to impeller housing 730 (FIG. 16) that has radial openings 732, and the impeller housing 1030 therefore has similar radial openings configured to discharge blood therethrough. In some embodiments, however, the impeller housing 1030 can be configured similar to impeller housing 730' (FIG. 17), or the impeller housing 1030 can have other configuration such that blood is discharged from inside the housing to the outer side thereof.

The catheter system 1000 includes at least one pressure sensor disposed, e.g., between the distal and proximal restriction members 1012, 1014, and such pressure sensor(s) acquire data indicative of measurements of blood flow in a zone between the restriction members 1012, 1014. The motor that activates the impeller 1015 can be controlled such that an increase in an RPM (revolutions per minute) of the motor results in a decrease of the pressure in the zone between the distal and proximal restriction members 1012, 1014.

Figure 27:
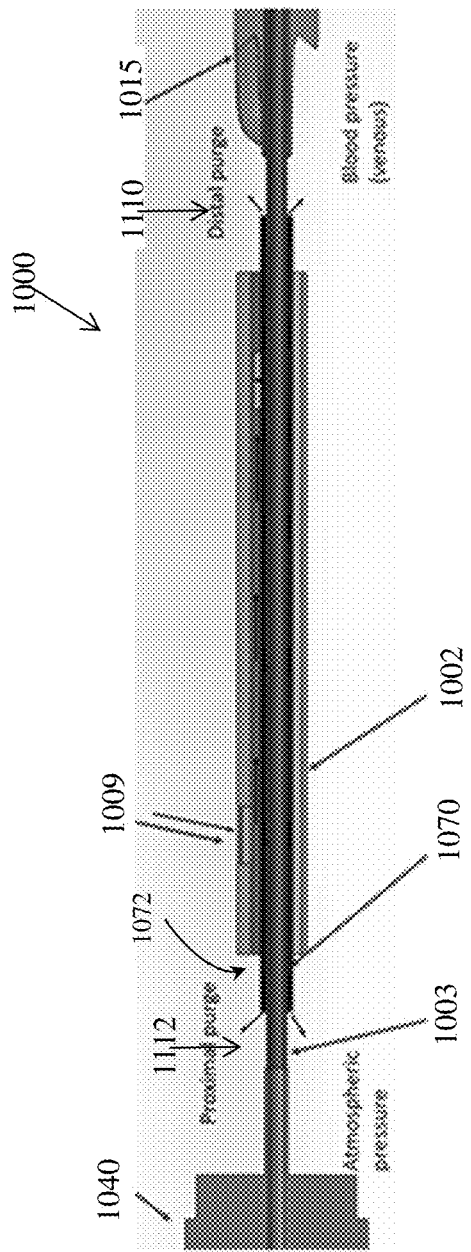
FIG. 27 is a cross-sectional side view of a portion of the implantable catheter system of FIG. 24.

FIG. 27 illustrates a portion of the catheter system 1000 having the catheter tube 1002 (a multi-lumen tube) that has a tubular sleeve 1070 extending through its inner lumen. The sleeve 1070 has the drive shaft 1003 extending therethrough, and the drive shaft 1003 rotates inside the sleeve 1070. A space or gap 1072 between an outer wall of the drive shaft 1003 and an inner wall of the sleeve 1070 is not hermetically sealed. Accordingly, in some embodiments, an infusion/purging system is provided that allows to fill the gap 1072 between the drive shaft 1003 and the sleeve 1072. The gap 1072 can be filled with fluid to avoid penetration of air into the patient's venous system and blood leakage into the catheter tube. Referring back to FIG. 23, the system 1001 includes the infusion system 1006 configured to deliver a fluid into the gap 1072 between the drive shaft 1003 and the sleeve 1072. Because fluid(s) are delivered through the relatively narrow gap 1072, at a controlled rate, the infusion/purging system 1006 can allow infusing fluid(s) to a patient which has fluid intake limitations. The infusion system 1006 is also configured to flash to the blood stream particles and other material that can be produced, for example, due to friction between the drive shaft and the sleeve.

In use, the infusion system 1006 is configured to deliver a fluid to the gap 1072 between the drive shaft 1003 and the sleeve 1070 via an infusion port 1009. In the illustrated embodiment, the fluid can flow from the infusion port 1009 proximally towards a proximal end or point 1112 of the gap 1072 and/or from the infusion port 1009 distally towards a distal end or point 1110 of the gap 1072. The fluid can be, for example, saline heparin or saline, or other suitable fluid. The fluid can be delivered at a relatively slow rate such as, for example, in a range from about 1 ml/hr to about 10 ml/hr. Referring back to FIG. 23, in some embodiments, an infusion line 1108 between the infusion container 1106 and the catheter system 1000 can be coupled to a proximal port on the catheter's multi-lumen tube 1002. The infusion container 1106 releasably storing the fluid can be located at a height in a range from about 10 cm to about 40 cm relative to a point of incision created in the patient to deliver the catheter system 1000. The rate of the fluid delivery can be controlled by adjusting a height of the infusion container 1106 relative to the catheter system 1000. As shown in FIG. 27, the infusion system, which delivers the infusion fluid to the catheter system 1000 via the infusion port 1009, can flash particles out from the catheter tube through the proximal purge outflow towards the proximal point 1112. A minimum amount of fluid can be delivered into the patient from the infusion port 1009 and through the distal purge outflow towards the distal point 1110, thereby preventing blood from flowing up and into the catheter (i.e., to the left in FIG. 27). In addition, in some embodiments, the fluid can be delivered into the gap 1072 through a gap's distal point or side 1110. The distal point 1110 can be disposed, e.g., at about 1-2 cm proximal to the impeller 1015. In the illustrated embodiments, a first volume of the infusion/purge fluid can flow proximally (from the infusion port 1009 towards the proximal point 1112), and a second volume of the infusion/purge fluid can flow distally (from the infusion port 1009 towards the distal point 1112), with the first volume being greater than the second volume.

In the illustrated embodiment, a distance between the infusion port 1009 and the distal end 1110 of the gap 1072, as well as a distance between the infusion port 1009 and the proximal end 1112 of the gap 1072 determine a resistance to blood flow in the patient's body that can be created by the infusion fluid flowing through the catheter system. In particular, the ratio of these distances determines the resistance of the infusion flow to the blood flow. Thus, the closer the infusion port 1009 is to the distal end 1110 of the gap 1072, the higher is the distal pressure of the infusion fluid that blocks blood from entering the gap 1072. In this way, the ratio of the distances between the infusion port 1009 and the distal end 1110 of the gap 1072 and between the infusion port 1009 and the proximal end 1110 of the gap 1072, as well as the height of the infusion container 1106 relative to the catheter system 1000 at least partially implanted into the patient, together control resistance to the flow and the pressure of the fluid introduced into the system 1000 through the infusion port 1009. In some embodiments, the height of the infusion container 1106 can be adjusted so as to deliver the fluid through an infusion port 1009, such that the fluid leaves the gap 1072 via a proximal side 1112 of the gap 1072. The flow rate can be adjusted by the height of the infusion container creating a pressure gradient that determines the flow rate. The height of the infusion container minus the blood pressure at the distal purge defines the driving force for the flow of fluids into the patient. In order to prevent blood from flowing up into the catheter, there has to be flow into the patient. It is desirable to have this flow into the patient as small as possible so as not to overload the patient with fluids. Accordingly, the height of the infusion container 1106 is adjusted so as to achieve a pressure gradient of about 5 mmHg, such that the infusion/purge fluid flows into the patient in a rate that is equal to or less than 2 ml/hr. The delivery of the fluid through the infusion port 1009 allows the fluid to flow from the infusion port 1009, through the gap 1072, and towards the distal side 1110. When the air or liquid(s) flow through the gap 1072 towards the proximal side 1112, as in the described embodiment, this may additionally assist in cooling the motor 1040.

Figure 28:
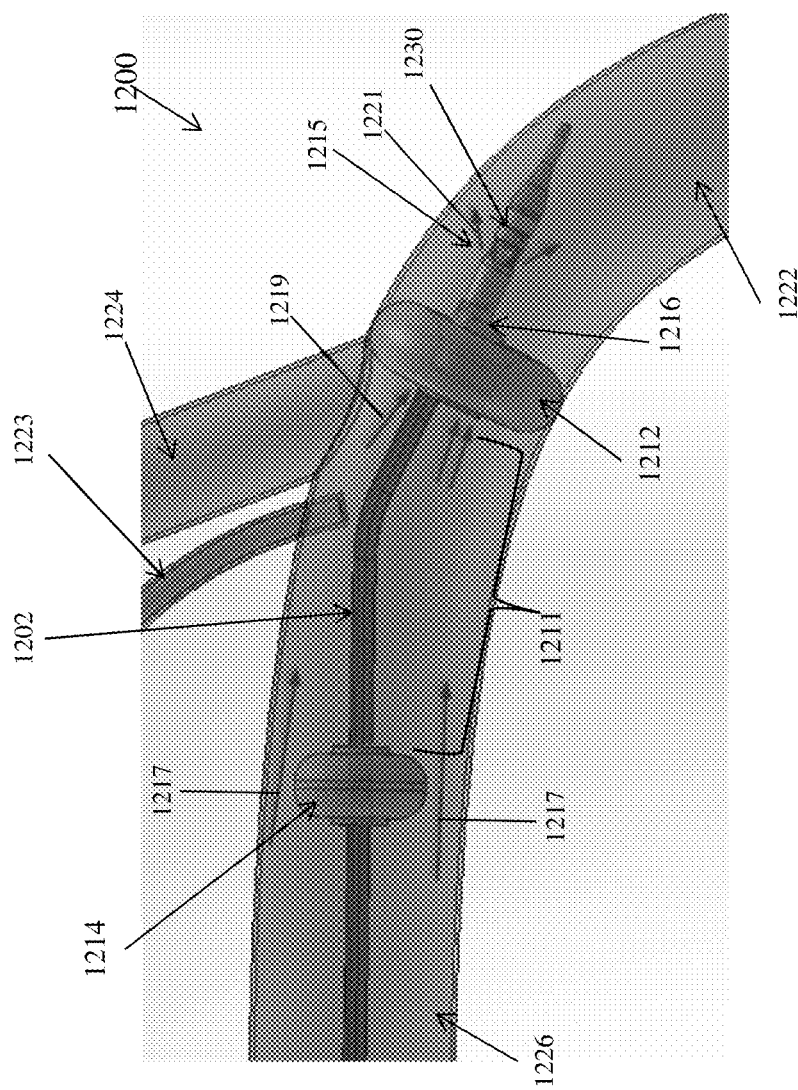
FIG. 28 is a perspective view of an embodiment of an implantable catheter system, showing the implantable system implanted in a patient's body.
Figure 29:
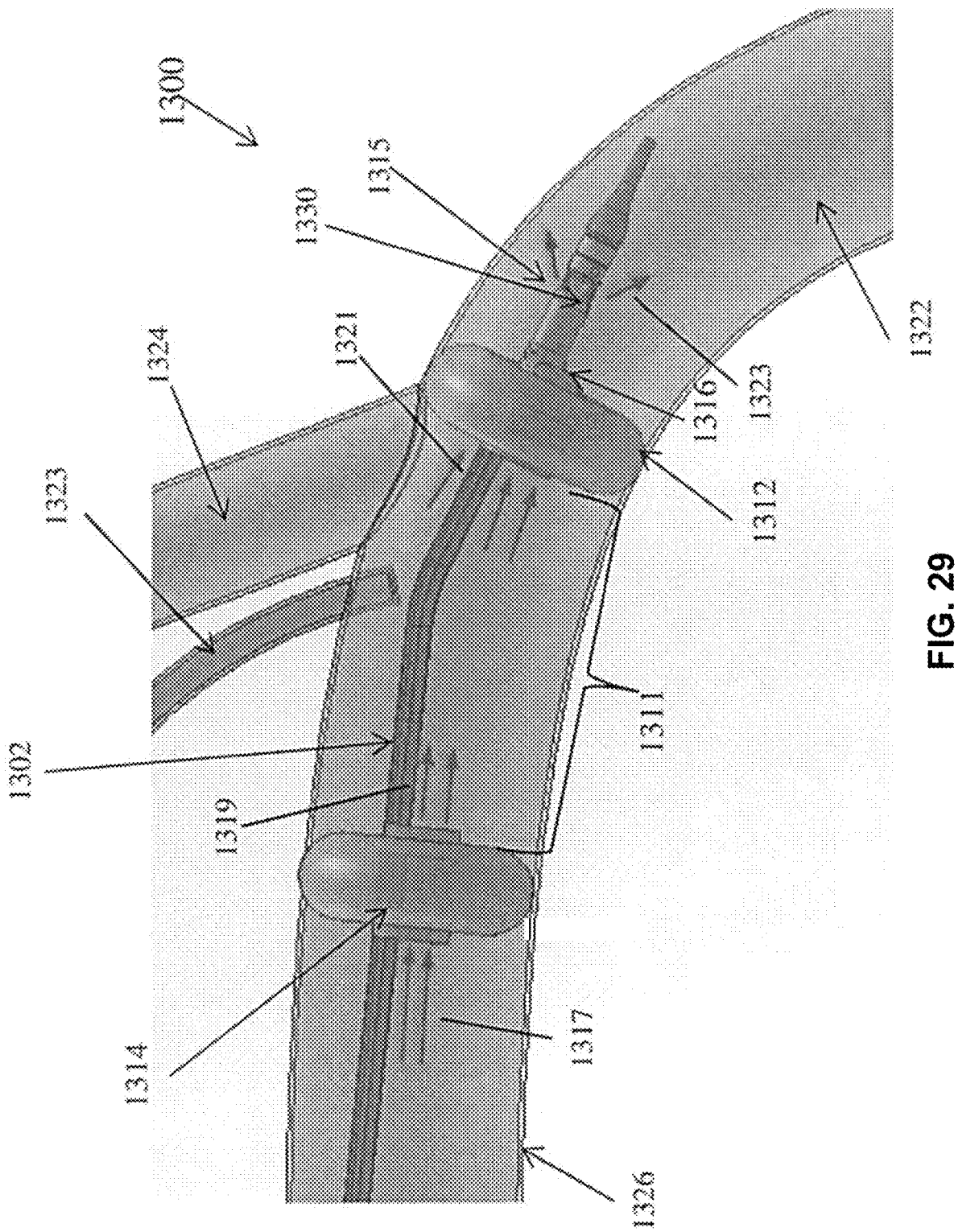
FIG. 29 is a perspective view of another embodiment of an implantable catheter system, showing the implantable system implanted in a patient's body.

FIGS. 28 and 29 show examples of implantable catheter systems in which the described embodiments can be implemented. Thus, FIG. 28 shows a catheter system 1200 having a catheter tube 1202, an impeller 1215, and distal and proximal restriction members 1212, 1214, which are shown in FIG. 28 in the activated (e.g., inflated) configuration. The catheter system 1200 can be similar to any of the system 1000 (FIGS. 23 and 24), system 700 (FIG. 7), system 800 (FIG. 11), and system 900 (FIG. 12) and is therefore not described in detail herein. As shown in FIG. 28, the catheter system 1200 can be implanted into the patient's body such that the distal restriction member 1212 is disposed in the innominate vein 1222 in proximity to the subclavian vein 1226, and the proximal restriction member 1214 is disposed proximal to the distal restriction member 1212 in the jugular vein of the patient at least about 1 cm before its confluence with the subclavian vein so as not to block the outflow of the thoracic duct. The same apparatus can be in either left or right sides of the neck, i.e., inserted through the right or left internal jugular veins. In some embodiments, an inner lumen of the proximal restriction member 1214 can have a diameter that is less than a diameter of an inner lumen of the distal restriction member 1212. However, in some implementations, these diameters can be substantially (e.g., with a small deviation, such as, e.g., from about 5% to 10%) the same.

In this example, as shown in FIG. 28, the proximal restriction member 1214 is moved into the activated (e.g., inflated) configuration such that its outer surface is spaced away from the inner wall of the jugular vein 1226. In this way, a diameter of the expanded proximal restriction member 1214 is less than a diameter of the expanded distal restriction member 1212, and the fluid is allowed to be passed in the gap between the outer surface of the proximal restriction member 1214 and an inner wall of the vein. The catheter system 1200 can be attached at an implantation site at the vein such that its position is maintained, and such that the proximal restriction member 1214 is disposed approximately centrally within the vein.

FIG. 29 illustrates a catheter system 1300 having a catheter tube 1302, an impeller 1315, and distal and proximal restriction members 1312, 1314, which are shown in FIG. 29 in the activated (e.g., inflated) configuration. The catheter system 1300 can be similar to any of the system 1000 (FIGS. 23 and 24), system 700 (FIG. 7), system 800 (FIG. 11), system 900 (FIG. 12), and system 1200 (FIG. 28), and is therefore not described in detail herein. As shown in FIG. 29, the catheter system 1300 can be implanted into the patient's body such that the distal restriction member 1312 is disposed in the innominate vein 1322 in proximity to the subclavian vein 1324, and the proximal restriction member 1314 is disposed proximal to the distal restriction member 1312 in the jugular vein 1326 of the patient. In this example, as shown in FIG. 29, the proximal restriction member 1314 is moved into the activated (e.g., inflated) configuration such that its outer surface is adjacent to the inner wall of the jugular vein 1326. In this way, the restriction member 1314 can be inflated such that its outer surface is in contact with the inner wall of the jugular vein 1326. In some embodiments, an inner lumen of the proximal restriction member 1314 can have a diameter that is less than a diameter of an inner lumen of the distal restriction member 1312. However, in some implementations, these diameters can be substantially (e.g., with a small deviation, such as, e.g., from about 5% to 10%) the same.

As shown in FIGS. 28 and 29, the catheter system can be implanted such that a zone at the bifurcation of the patient's jugular and subclavian veins in proximity to an outflow of a thoracic duct (1223 in FIGS. 28 and 1323 in FIG. 29) is at least partially sealed using the distal and proximal restriction members. Once the impeller of the catheter system is operated by a motor, the blood is caused to be pumped and the pressure inside an isolated zone will be dropped. Thus, FIG. 28 shows a low pressure zone 1211 that is created between the distal and proximal restriction members 1212, 1214. Similarly, FIG. 29 shows a low pressure zone 1311 that is created between the distal and proximal restriction members 1312, 1314.

In the example of FIG. 28, when the impeller 1215 is activated, blood flows (arrows 1217) from a proximal side of the proximal restriction member 1214 such that the blood passes between the outer surface of the proximal restriction member 1214 and an inner wall of the vein. The blood can also flow through an inner lumen of the proximal restriction member 1214. The blood then follows from the proximal restriction member 1214 towards (arrows 1219) and through a lumen of the distal restriction member 1212, and the bloods exits (arrows 1221) the catheter system 1200 via openings in an impeller housing 1230 having the impeller 1215 therein. Similar to other embodiments, the blood is directed from the lumen of the distal restriction member 1212 to the impeller housing 1230 via a membrane 1216, such as, e.g., a conical membrane.

In the example of FIG. 29, when the impeller 1315 is activated, the blood flows toward (arrows 1317) and through (arrows 1319) a lumen of the proximal restriction member 1314, towards (arrows 1321) and through a lumen of the distal restriction member 1312, and the bloods exits (arrows 1323) the catheter system 1300 via openings in an impeller housing 1330 having the impeller 1315 therein. The blood is directed from the lumen of the distal restriction member 1312 to the impeller housing 1330 via a membrane 1316, such as, e.g., a conical membrane. As discussed above, one or more pressure sensors can be disposed between the distal and proximal restrictors, and/or on one or both sides of the restrictors. The blood pressure is regulated by controlling a motor RPM based on blood pressure measurements acquired from the sensors.

It should be appreciated that, although not shown, the catheter system 1000 (FIGS. 24, 25, and 27), catheter system 1200 (FIG. 28), and catheter system 1300 (FIG. 29) can include or can be associated with one or more pressure sensors, such as, for example, one or more of pressure sensors S1, S2, S3 (FIG. 11). Furthermore, any of the catheter systems described herein can be associated with sensors of any other type.

A catheter system, such as, for example, catheter system 1200, catheter system 1300, or any other catheter system in accordance with the described subject matter, can be delivered into an implantation site in various ways. In some embodiments, an introducer sheath is inserted through an incision and into the jugular vein of a patient, e.g., approximately 10 cm above the subclavian vein junction (venous angle). The catheter system, having distal and proximal restrictors in a non-deployed configuration, is then inserted over a guide wire into the jugular vein (posterior approach). The catheter system is inserted such that the proximal restrictor, in a non-deployed configuration, is positioned in the jugular vein, e.g., about 1.5 cm above (toward the patient's head) the subclavian drainage. Once it is determined (e.g., using ultrasound or another imaging technique) that the catheter system is positioned as desired, the guide wire is removed. The sheath is then attached to the patient (e.g., to the patient's skin) at a location that allows for axial adjustment of the catheter system. The catheter system can be associated with one or more pressure sensors.

Once the sheath is attached to the patient, fluid, such as, e.g., heparin bolus, is administered to the patient and a motor coupled to the catheter system can be connected to a power source and to an infusion system. The motor can be activated to operate, e.g., at $22k$ RPM (or another rate) to allow a constant blood flow through the blood pathway. The distal restrictor is then deployed (inflated) to radially expand so as to constrict the vein. The proximal restrictor is then deployed until a change in pressure is detected (e.g., using the pressure sensor(s)). The inflation of the distal restrictor is then determined to be completed, and the motor is controlled based on a predefined pressure value. Such value can be set via a suitable control system. The CVP is be measured trough the sheath luer at any time point from this point forward the system will be operated automatically to keep isolated zone at nominal pressure value of about 2.5 mmHg by controlling the motor RPM.

The embodiments described in connection with FIGS. 23-29, which include a catheter system associated with an infusion system, can provide various advantageous features. For example, because at least one of the distal and proximal restrictors is deployed (e.g., inflated) to occupy at least partially the perimeter of a vessel in a patient's body, and because a suction lumen is defined by the restrictors, the vessel is prevented from collapsing on the suction lumen and thus blocking the blood entrance. Furthermore, because there is a free passage between the isolated zone and the innominate vein, in case of a malfunction of the system or an unintentional interruption of a motor, a risk of undesirable pressure elevation and blood stagnation within the isolated zone is decreased or eliminated. Furthermore, the configuration of the system's components, such as a membrane with a conically-shaped portion, a relatively large suction diameter of the distal restrictor and a position of the impeller in proximity to the distal restrictor allows achieving a decreased resistance to blood flow during suction. This allows the impeller to pump the required amount of blood at a reduced rotational speed, which decreases a possibility of mechanical hemolysis (which can occur due to high shear stresses on the blood cells) and improves overall safety of the catheter system. Additionally, a need for a jugular flow bypass can be eliminated. Furthermore, flow rates and blood pressure are controlled by controlling the motor to increase and decrease RPM continuously and in real time. In this way, the operation of the system can account for the pressure changes in the venous system due to the heart beats and breathing.

It should be appreciated that the catheter system described in connection with FIGS. 23-29 can have any suitable variations. Also, other components can be used in conjunction with the catheter system to facilitate blood pressure reduction in the patient's vein in a desired manner. For example, in at least one embodiments, a venous constrictor cuff of any suitable configuration can be placed on the patient's forearm so as to restrict subclavian vein flow to a rate in a range from about 50 ml/min to about 100 ml/min, thus enabling less blood needing to be circulated by the impeller.

In some embodiments, various systems and methods are provided for treating edema, for example, chronic fluid overload or other edema. In general, a pump can be configured to be implanted within a patient at risk of developing edema. The pump can be configured to pump fluid out of the patient's lungs, e.g., out of the patient's interstitial and alveolar spaces. The pump can be configured to be fully implanted within the patient's body. The pump can be configured to continuously pump fluid, or the pump can be configured to be selectively actuatable in response to a trigger event. In an exemplary embodiment, the pump can include an inflow port coupled to an inflow tube in fluid communication with a lymphatic vessel of the patient, an outflow port coupled to an outflow tube in fluid communication with a vein of the patient, and an implantable battery.

Accordingly, in some embodiments, various systems and methods are provided for reducing pressure at an outflow of a duct such as the thoracic duct or the lymphatic duct, such as the right lymphatic duct. In general, the systems and methods may be effective to reduce edema conditions, such as, for example, fluid overload, in a patient by lowering an outflow pressure in a region around the patient's thoracic/lymphatic duct outflow. As a result of lowering the outflow pressure at the thoracic and/or lymphatic ducts, higher lymphatic return will be achieved, enabling the lymphatic vessel flow to be at or near normal levels. The systems and methods may be effective to alleviate conditions of the edema and increase the patient response rate. In exemplary embodiments, the systems and methods may be particularly useful to treat long-term, or chronic, fluid overload, however a person skilled in the art will appreciate that the systems and methods can be used in various procedures for treating a lymphatic system fluid clearance imbalance.

At least some embodiments described herein generally relate to systems and methods for treating chronic fluid overload. In general, a pump can be configured to be implanted within a patient at risk of developing edema. The pump can be configured to pump fluid out of the patient's lungs, e.g., out of the patient's interstitial and alveolar spaces, which can help prevent the fluid from building up to a dangerous degree. The pump can thus be configured to facilitate prevention of edema by limiting fluid build-up in the lungs, if not preventing fluid build-up entirely. In other words, the pump can be configured to facilitate treatment of chronic edema, such as can occur in connection with chronic heart failure. The pump can be configured to facilitate higher lymphatic return by lowering outflow pressure at a lymphatic vessel of the patient, e.g., at the patient's thoracic duct and/or lymphatic duct, for example, the right lymphatic duct.

The pump can be configured to be fully implanted within the patient's body, thereby helping the device to be unobtrusive in the patient's daily life, similar to a pacemaker. The pump can be configured to be operated using a battery. In some embodiments, a single battery can be used for any suitable time period during which the pump remains implanted in a patient's body. The pump can be configured to continuously pump fluid, which can help ensure the removal of fluid that collects in the lung space before a dangerous amount of the fluid builds up and/or can help ensure the long term patency of the pump. Alternatively, the pump can be configured to be selectively actuated in response to a trigger event, such as in response to a value of a measured parameter (e.g., pressure, fluid amount, bioimpedance, heart rate, breathing rate, patient activity level, organ dimension, etc.) or in response to receiving a user input requesting pumping. The pump can thus be configured to only periodically pump fluid, e.g., only periodically run so as to alternate between periods in which the pump is running to provide fluid flow and in which the pump is not running. Running periodically can help conserve power (e.g., battery power) and/or can be appropriate for patients with lower risks of developing edema and/or for patients who tend to be more at risk of developing edema at certain times (e.g., during the day instead of at night, when exercising, etc.) instead of having a more constant risk. In at least some embodiments, the pump can be configured to be selectively switched between a continuous mode in which the pump runs continuously and a periodic mode in which the pump runs periodically, which can help the pump be most effectively used according to each patient's current needs.

In some embodiments, the system can include any one or more of the following components: an implantable device that includes an implantable device, an implantable pump, one or more sensors, and a controller. The components of the system can operate to alleviate chromic fluid overload.

Figure 30:
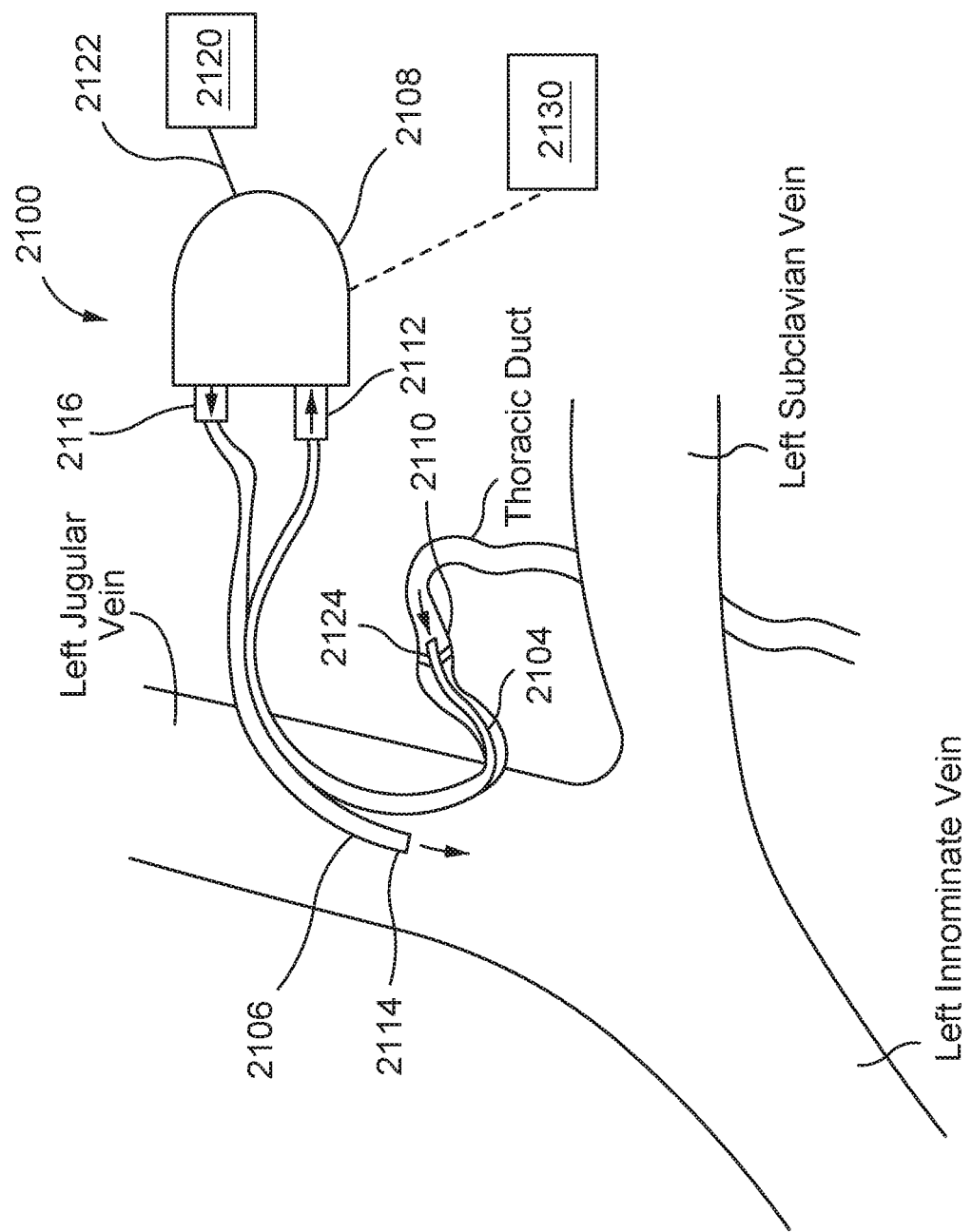
FIG. 30 is a schematic perspective view of an embodiment of an implantable device implanted in a body.

FIG. 30 illustrates an example of an implantable device 2100 in accordance with some implementations of the current subject matter. The implantable device 2100 is configured to be implanted in a body of a patient and can be used to withdraw lymph fluid from the thoracic duct of a patient, as shown schematically in FIG. 30. The implantable device 2100 includes an inlet or inflow tube 2104, an outlet or outflow tube 2106, and an implantable pump 2108. The inflow and outflow tubes 2104, 2106 are connected to the implantable pump 2108 as shown in FIG. 30.

As illustrated, the inflow tube 2104 having an inflow opening 2110 can be coupled to an inflow port 2112 of the pump 2108, and the outflow tube 2106 having an outflow opening 2114 can be coupled to an outflow port 2116 of the pump 2108. For reference, FIG. 30 also shows the patient's left subclavian vein, thoracic duct, left innominate vein and jugular vein. As shown, the inflow opening 2110 of the inflow tube 2104 can be positioned within the thoracic duct. The valves of the thoracic duct ("valve") are shown in FIG. 30. The outflow opening 2114 of the outlet tube 2106 is positioned within a blood vessel such as, in this example, the jugular vein.

Thus, the pump 2108 in this illustrated embodiment generally provides a bypass from the thoracic duct to the left jugular vein, thereby allowing for a constant draining option for the lymphatic duct (e.g., the right lymphatic duct) in case venous pressures elevate. The pump 2108 can be configured to be automatically activated to drain fluid on demand in response to a measured increase in pressure. Also, the pump 2108 can be activated in response to a user input, or in other manner. A bypass can be similarly provided by positioning the outflow opening 2114 at the subclavian vein instead of the left jugular vein.

As shown in FIG. 30, the inflow port 2112 coupled to the inflow tube 2104 is in fluid communication with the thoracic duct of the patient, and the outflow port 2116 coupled to the outflow tube 2106 is in fluid communication with a vein of the patient, e.g., the patient's internal jugular vein. The outflow port 2116 can alternatively be in fluid communication with a subclavian vein, innominate vein (also referred to as a "brachiocephalic vein"), or superior vena cava. The pump can thus be configured to pump fluid from the thoracic duct to the vein so as to facilitate removal of fluid from the thoracic duct and thereby facilitate higher lymphatic return by lowering outflow pressure at the lymphatic vessel. Because lymphatic systems can have different anatomies in different patients, the inflow tube can be positioned to be in fluid communication with the patient's thoracic duct or any duct that drains into the patient's subclavian vein, jugular vein, innominate vein, or superior vena cava The implantable pump 2108 can have a variety of sizes, shapes, and configurations. In an exemplary embodiment, the pump 2108 can be any one of a pulsatile pump, a periodical pump, and a continuous flow pump.

The pump 2108 can have a size configured to facilitate implantation of the pump 2108 within the patient's lung. In at least some embodiments, the pump 2108 can have a size configured to allow the pump 2108 to be implanted within a duct of the patient, such as a thoracic duct of the patient. In an exemplary embodiment, the pump 2108 can have a length in a range of about 2 to 3 cm and a diameter of about 20 mm.

In an exemplary embodiment, the pump 2108 can be configured to pump fluid at a rate in a range of about 10 to 1000 ml/hour (milliliters per hour), e.g., in a range or about 200 to 600 ml/hour, about 300 ml/hour, about 500 ml/hour, etc. In at least some embodiments, the pump 2108 can have a static, e.g., unchangeable, flow rate. The flow rate can thus be predictable and/or chosen for a specific patient. In other embodiments, the pump 2108 can have an adjustable flow rate. The flow rate being adjustable can help the pump 2108 accommodate changes in the patient's condition over time. The flow rate can be adjustable in a variety of ways, as will be appreciated by a person skilled in the art, such as by being wirelessly adjusted using a user-operated control device located external to the patient and configured to wirelessly communicate with the pump 2108 to adjust the flow rate thereof. The pressure gradient that the pump 2108 discharges against is less than about 15 mmHg. A total power of the pump can be in the range from about 0.02 Watt to about 0.7 Watt. In one embodiment, total power of the pump is about 0.166 Watt.

As shown in FIG. 30, the pump 2108 can be powered using an implantable battery 2120. The battery 2120, which can be rechargeable (including wirelessly) and/or replaceable, can have electrical capacity from about 25 mAh (milliamp Hour) to about 10 Ah. Thus, the battery 2120 can be able to operate for an extended period of time. For example, the total working time for the battery 2120 can be 22-9000 hours. In some embodiments, an average number of days that the pump 2108 remains implanted in the patient's body can be about 500 days. Thus, in the illustrated implementation, the implantable device 2100, once implanted, can be operated over a relatively long period of time to alleviate chronic edema, using a single battery.

The inflow tube 2104 can be secured to the thoracic duct using an attachment feature 2124 that can be in the form of an implantable balloon, a stent-like self-expanding structure, or an attachment feature having any other suitable configuration. The inflow and outflow tubes 2104, 2106 tubes can be manufactured from biocompatible materials, such as, e.g., silicone or thermoplastic polyurethane (TPU). Other biocompatible materials can be used additionally or alternatively.

The inflow and outflow tubes 2104, 2106 can each be removably coupled to their respective ports 2112, 2116 of the pump 2108 or can each be permanently coupled to their respective ports. The inflow and outflow tubes can each be flexible to facilitate their positioning within tortuous and/or curved lumens in the patient's body. The inflow and flexible tubes can each include, e.g., indwelling catheters. In an exemplary embodiment, both of the inflow and outflow tubes are coupled to the pump 2108 in a same manner, e.g., both removable or both permanent. As will be appreciated by a person skilled in the art, fluid can be configured to flow in to the pump 2108 through the inflow port and out of the pump 2108 through the outflow port, thereby facilitating pumping of the fluid.

The pump 2108 can be powered in a variety of ways. In at least some embodiments, the pump 2108 can be configured to be powered by an implantable power source in the form of the single battery 2120. In this illustrated embodiment, the pump 2108 is coupled to the battery 2120 via a power lead 2122. The battery 2120 can be rechargeable battery, which, in some implementations, can be configured to be recharged wirelessly. The implantable power source 14 can have a variety of sizes, shapes, and configurations. It should be appreciated that the power source can have other forms and/or can include a plurality of power sources. The battery 2120 can be included as part of the pump 2108. Alternatively, as in this illustrated embodiment, the battery 2120 can be a separate component from the pump 2108 and can be configured to be in electronic communication therewith along a power line, e.g., the power lead 2122, etc. The battery 2120 can be implanted at an anatomical location outside the patient's lung, such as a shoulder of the patient, or in other anatomical areas.

The pump 2108 can be configured to continuously pump fluid, e.g., continuously pump fluid through the inflow port and out the outflow port. The pump 2108 can thus be configured to continuously pump fluid out of the area at which an input opening of the inflow tube coupled to the inflow port is located, e.g., out of the patient's thoracic duct and into the area at which an output opening of the outflow tube coupled to the inflow port is located, e.g., into a vein of the patient such as the patient's subclavian vein, internal jugular vein, innominate vein, or superior vena cava.

The pump 2108 can be configured to periodically pump fluid, e.g., have alternating periods of pumping and no pumping, based on information acquired by one or more sensors. Operation of the pump 2108 is controlled by a controller 2130 schematically shown in FIG. 30. The controller 2130 can be configured to be implanted in the patient's body and it can communicate with the pump 2108 via a wired or a wireless connection. The controller can be configured to cause the pump 2108 to not pump (e.g., be in an idle state) until the occurrence of a trigger event. In other words, the pump 2108 can have a default idle state and can be configured to move between the default idle state and an active state in which the pump 2108 pumps fluid in response to the trigger event. The trigger event can be a dynamic trigger event generated based on certain measurements acquired by the sensors.

In some implementations, a dynamic trigger event can include a value of a measured parameter being out of range as compared to a threshold value and/or threshold range of values. The parameter can be measured using a sensor (not shown) associated with the patient having the pump 2108 implanted therein. Examples of sensors that can be used to measure a parameter include pressure sensors (e.g., central venous pressure (CVP) or other fluid pressure sensors, and blood pressure sensors), radio frequency transmitters and receivers, fluid sensors, bioimpedance sensors, heart rate sensors, breathing sensors, activity sensors, optical sensors. Pressure sensors can be placed, for example, in the patient's venous system, in the patient's heart, in the patient's arterial system, and/or in the patient's body at target anatomical sites that may suffer from an increase of interstitial fluid overload. Fluid sensors can be placed, for example, in the lungs. Examples of the measured parameter include pressure (e.g., as measured by a pressure sensor), fluid amount (e.g., as measured by a fluid sensor), bioimpedance (e.g., as measured by a bioimpedance sensor), heart rate (e.g., as measured by a heart rate sensor), breathing rate (e.g., as measured by a breathing sensor), patient activity level (e.g., as measured by an activity sensor), and organ dimension (e.g., as measured by an optical sensor). The sensor can be implanted in the patient as part of the pump 2108, implanted in the patient as a separate component from the pump 2108, or the sensor can be located external to the patient, such as by being on a skin surface thereof. If not already a part of the pump 2108 so as to be in electronic communication therewith, the sensor can be configured to be in electronic communication with the pump 2108 over a communication line such as a wired line or a wireless line. The sensor can include one or more sensors. In embodiments including a plurality of sensors, each of the sensors can be configured to measure the same parameter as or a different parameter than any one or more of the other sensors.

Accordingly, in some implementations, one or more sensors as described herein can be used to detect congestion in the form of accumulation of fluid in the thoracic duct and the pump 2108 can be activated dynamically, in response to the detection of the congestion. Additionally or alternatively, the congestion can be detected based on measurements of current and/or voltage consumption by the pump 2108.

In some implementations, the pump 2108 can be configured to pump/not pump in response to a trigger event generated based on user input. The pump 2108 can thus be configured for on-demand pumping. The user can therefore cause pumping when desired (e.g., during a shortness of breath episode, when the user notices a slight weight gain, etc.) which can help the pump 2108 run efficiently and when most needed as determined by the user. The user can include the patient or another person, such as the patient's doctor, the patient's caretaker, etc. The input can be provided to the pump 2108 in a variety of ways. In an exemplary embodiment, the input can be provided wirelessly to the pump 2108 using a user-operated control device located external to the patient and configured to wirelessly communicate with the pump 2108 to cause the pump 2108 to start pumping (e.g., change the pump 2108 from the idle state to the active state) or to stop pumping (e.g., change the pump 2108 from the active state to the idle state).

Also, in some embodiments, the pump 2108 can be configured to periodically pump on a set schedule, e.g., alternately pump for x minutes and not pump for y minutes, where "x" and "y" can be equal or different. The set schedule can be preprogrammed into the pump 2108, e.g., in a controller thereof (discussed further below). The set schedule can be static or can be adjustable. The set schedule can be adjustable in a variety of ways, as will be appreciated by a person skilled in the art, such as by being wirelessly adjusted using a user-operated control device located external to the patient and configured to wirelessly communicate with the pump 2108 to adjust the pumping schedule thereof. Having a set schedule can allow the pump 2108 to be relatively simple electronically and not require much processing capability.

In at least some embodiments, the pump 2108 can be configured to change its pumping rate (e.g., from zero to a non-zero value, from a non-zero value to zero, or from one non-zero value to another non-zero value) based on a fluid amount measured by a fluid sensor. If the measured fluid amount exceeds a predetermined threshold maximum fluid amount value, the pump 2108 can be configured to increase its pump rate (e.g., increase from zero or increase from some non-zero value) in an effort to decrease the amount of fluid present.

Also, in some embodiments, the pump 2108 can be configured to operate in more than one mode, such that it can switch between being operated in response to a manual trigger (based on user input), in response to an event defected based on sensor-acquired measurements (a dynamic control), or based on a predetermined schedule. The switching between them can be controlled based on user input or automatically.

The pump 2108 can include only a continuous mode of operation such that the pump 2108 can only continuously pump fluid, the pump 2108 can include only a periodic mode of operation such that the pump 2108 can only periodically pump fluid, or the pump 2108 can include the continuous and periodic modes of operation and be configured to be selectively switched between the continuous mode of operation and the periodic mode of operation. The mode switching can be accomplished in a variety of ways, as will be appreciated by a person skilled in the art such as by being wirelessly switched using a user-operated control device located external to the patient and configured to wirelessly communicate with the pump 2108 to change the mode of operation thereof.

The controller 2130 (e.g., a processor, a microcontroller, etc.) in electronic communication with the pump 2108 can be configured to facilitate control of the pump 2108, e.g., control changing the pump's mode of operation, etc. The controller can be included as part of the pump 2108 so as to be configured to be implanted in the patient with the pump 2108 or, as in this illustrated embodiment, the controller can be a separate component from the pump 2108. The controller being part of the pump 2108 can help allow the pump 2108 to be a self-contained system, although in such a controller requires space in the pump 2108, which can increase a size of the pump 2108. The controller being a separate component from the pump 2108 can help the pump 2108 have a smaller size and/or can allow the pump 2108 to be controlled by a more powerful processor since the processor can be more easily upgraded than if implanted with the pump 2108 and/or since the processor's size can be less important when outside the pump 2108 as opposed to inside the pump 2108.

Figure 31:
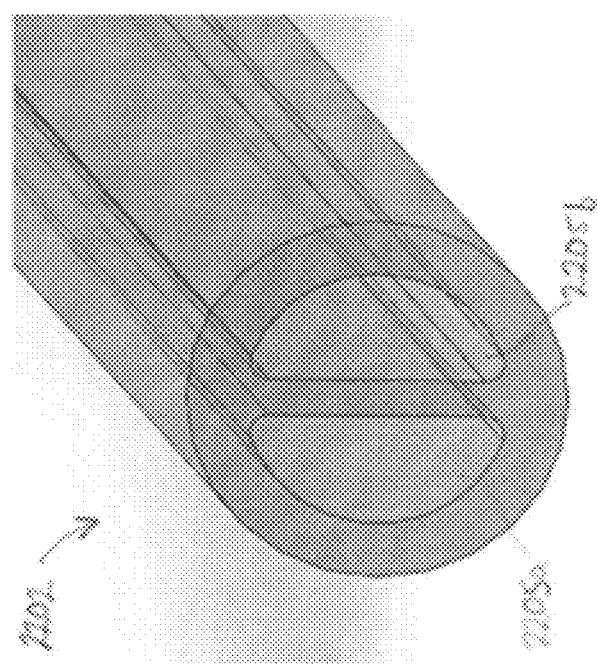
FIG. 31 is a partially transparent, cross-sectional view of an embodiment of a tube that can be used in the implantable pump system of FIG. 30.

Each of the inflow and outflow tubes 2104, 2106 can be a multi-lumen channel, with separate lumens to withdraw fluid from the thoracic duct to the pump 2108 and to direct fluid from the pump 2108 to the venous system. FIG. 31 illustrates an embodiment of a tube 2202 which can be any of the inflow or outflow tubes 2104, 2106. As shown, the tube 2202 has a generally circular cross-section and includes first and second lumens 2205*a*, 2205*b* which do not communicate with one another and thus provide separate flows. The inflow and outflow tubes 2104, 2106 can have more than two lumens. The first lumen 2205*a* can be a suction lumen, and the second lumen 2205*b* can be a discharge lumen. For example, the inflow tube 2104 can have a third lumen for inflating an attachment feature 2124 when it is an expandable element such as a balloon-type element. The inflow and outflow tubes 2104, 2106 can have a diameter from about 1 mm to about 3 mm, from about 2 mm to about 3 mm, or other diameters such that the tubes can be disposed within the thoracic duct and the vein.

Figure 32:
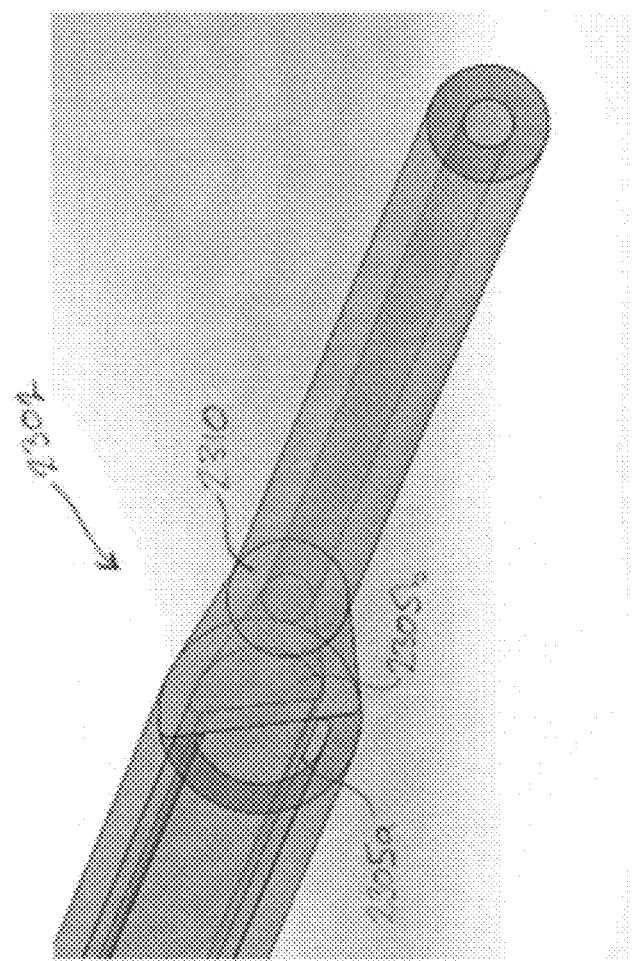
FIG. 32 is a partially transparent, cross-sectional view of a portion of the implantable device of FIG. 30.

In some embodiments, each of the inflow or outflow tubes 2104, 2106 can have a subcutaneous port accessible from outside of the patient's body and configured to be used to access the tubes 2104, 2106 to clean them when the implantable device 2100 is used over a prolonged period of time. The cleaning can be performed between treatment periods, and it can involve flushing the inflow and outflow tubes 2104, 2106 with an antiseptic solution. FIG. 32 illustrates an embodiment of a tube 2302 which can be any of the inflow or outflow tubes 2104, 2106. As shown, the tube 2202 has a generally circular cross-section and includes first and second lumens 2305a, 2305b which can be similar to the lumens 2205a, 2205b shown in FIG. 31. The tube 2302 has a subcutaneous port 2310 that can be used to clean the inflow and outflow tubes 2104, 2106 as part of maintenance of the implantable device 2100. The port 2310 can be manufactured from an elastomeric material and can be used to inject an antiseptic or other solution into the inflow and outflow tubes 2104, 2106 and to remove the solution from the tubes 2104, 2106 after it has been used.

Figure 33:
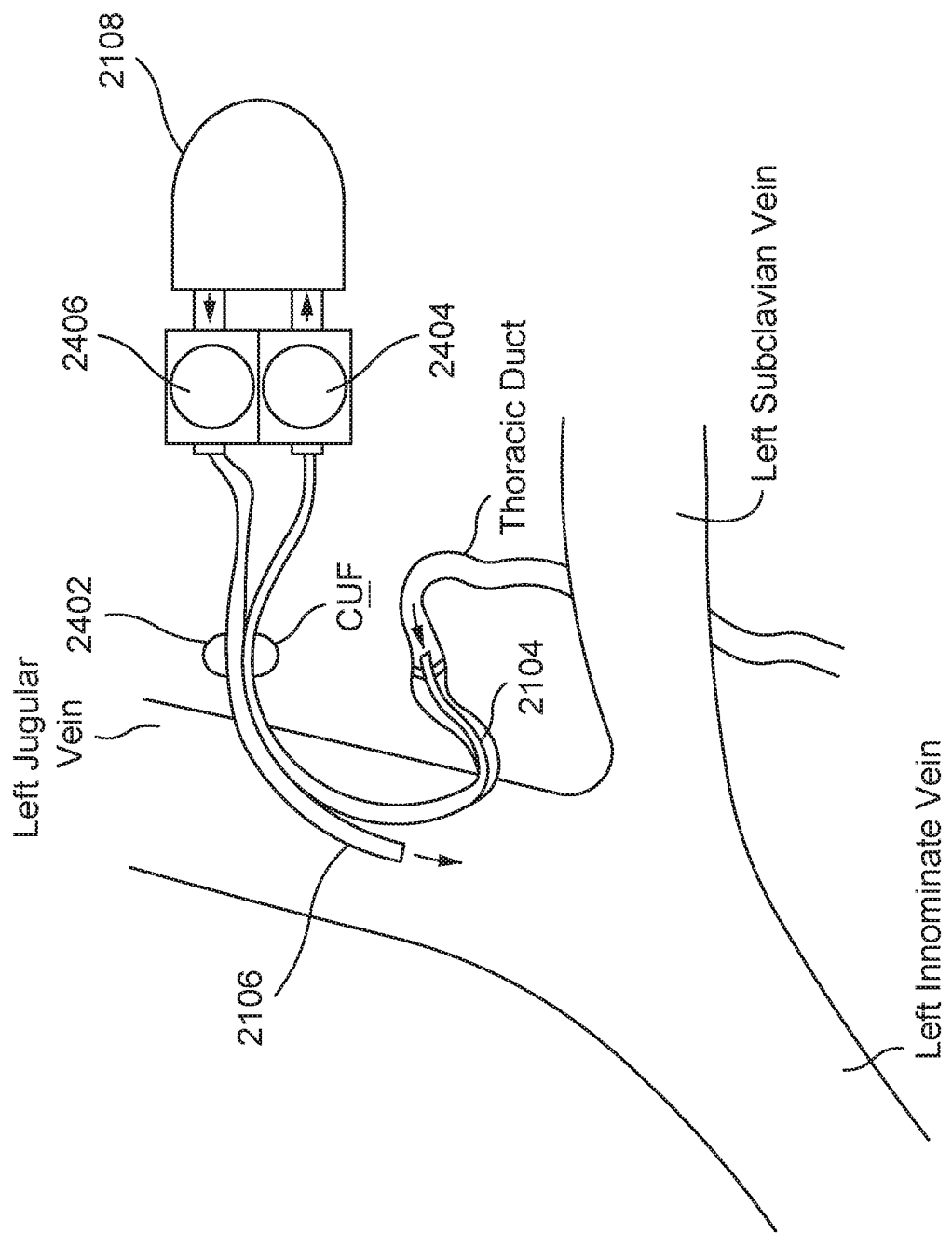
FIG. 33 is another perspective view of the implantable device of FIG. 30, illustrating the implantable device including an antimicrobial cuff.

In some embodiments, as shown in FIG. 33, each of the inflow and outflow tubes 2104, 2106 has a protective element configured to prevent contamination of the implantable device 2100. The protective element can be in the form of a cuff 2402 or other barrier that is disposed around the tubes 2104, 2106 in the vicinity of subcutaneous ports 2404, 2406 accessible from outside of the patient's body. The subcutaneous ports 2404, 2406 are configured to be used to access the tubes 2104, 2106 for cleaning or other purposes. The cuff 2402 protects contamination of the blood stream and thus reduces a possibility of infection. The cuff 2402 can be in the form of a sponge or other material including an antimicrobial agent. The material can be slow-releasing material which releases the antimicrobial agent slowly, over an extended time period.

Figure 34B:
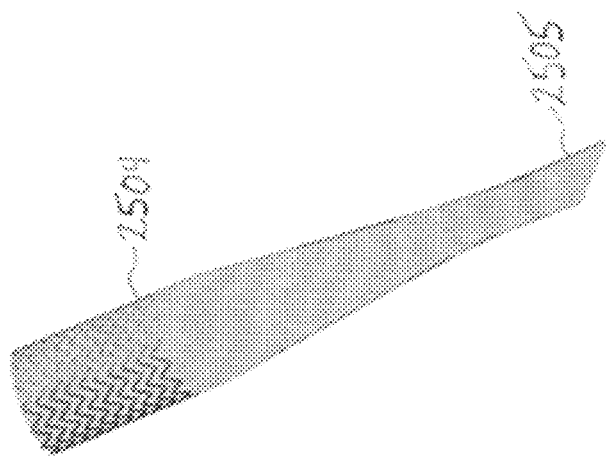
FIG. 34B is a perspective view of another stent that can be used in connection with the implantable device of FIG. 30.
Figure 34A:
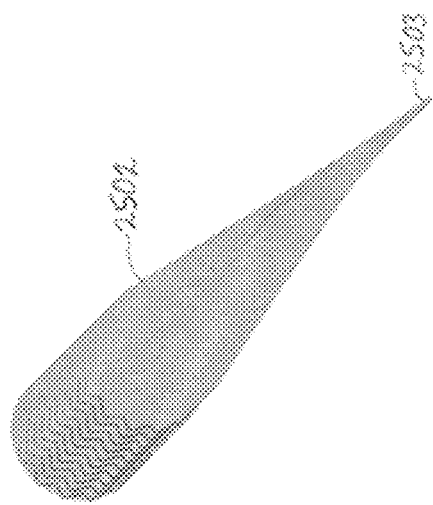
FIG. 34A is a perspective view of a stent that can be used in connection with the implantable device of FIG. 30.

The ostial valve of the thoracic duct is opened at low vein wall tension and closed at high venous wall tension. Therefore, patients with distended jugular pressure may exhibit low lymphatic flow due to closure of the ostial valve of the thoracic duct. FIGS. 34A and 34B illustrate examples of stents or stent-like devices 2502 and 2504 that can be implanted to alleviate the ostial valve closure by enabling the valve to release the lymph fluid. The stents can be configured to expand (corresponding to an activated configuration) and constrict (corresponding to a relaxed configuration). The stent-like device 2502 can be tapered and has a rounded tip 2503. The stent-like device 2504 can also be tapered and has a slanted tip 2505. The stent-like devices 2502 and 2504 can have a variety of other configurations. The stent-like devices 2502 and 2504 can include a valve (e.g., a duckbill valve or valve of another type(s)) (not shown) configured to cause release of the lymph fluid. The devices 2502 and 2504 can be manufactured from such material such as, e.g., polytetrafluoroethylene (ePTFE). The stent-like devices 2502 and 2504 can be attached to the inflow tube 2104 and can additionally be used for anchoring the inflow tube 2104 within the thoracic duct. In some embodiments, the stent-like devices 2502 and 2504 can be connected to an implanted pump (e.g., the pump 2108 in FIG. 30) and function as an inlet port.

Figure 34C:
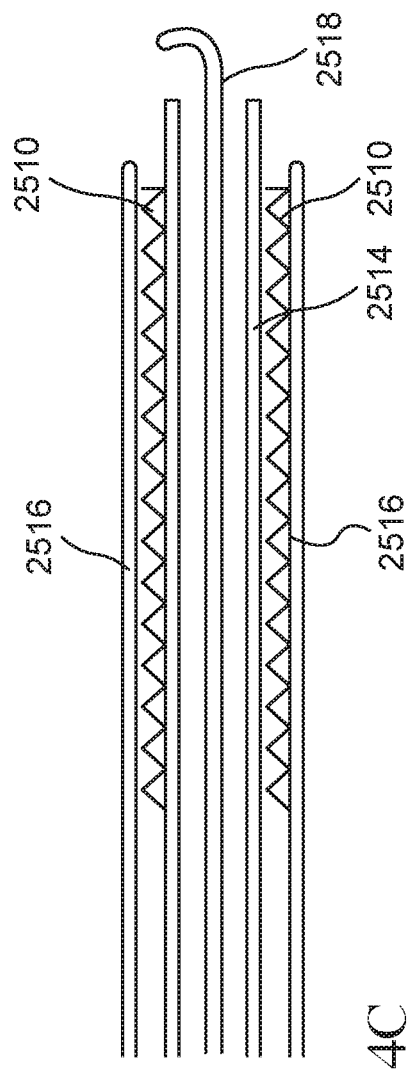
FIG. 34C is a schematic side diagram illustrating deployment of a stent.
Figure 34D:
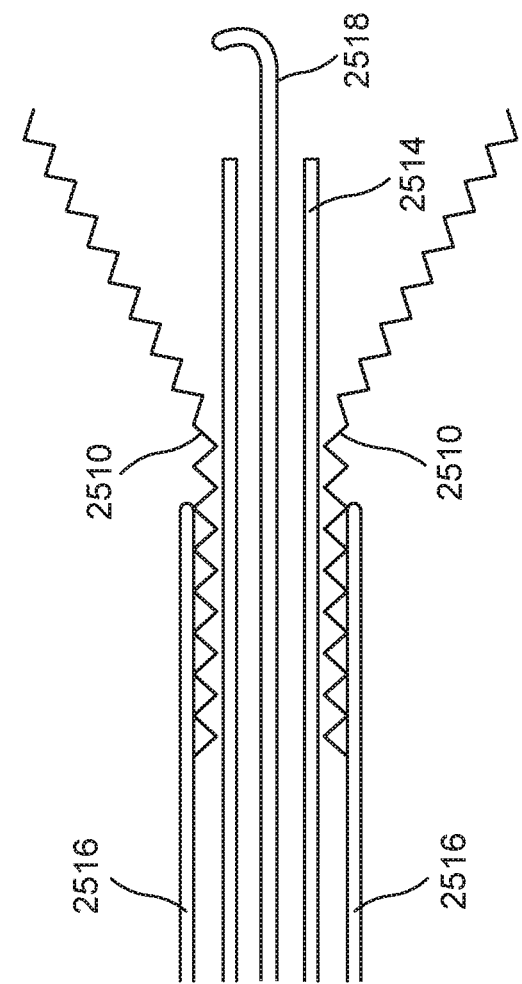
FIG. 34D is another schematic diagram illustrating deployment of the stent of FIG. 34C.

FIGS. 34C and 34D illustrate an example of one embodiment of deployment of a stent 2510 in a thoracic duct (not shown) of a patient, such as within the ostial valve of the thoracic duct. The stent 2510, shown partially in FIGS. 34C and 34D, can be any of the stent-like devices 2502 and 2504, or a stent having another configuration. As shown in FIG. 34C, the stent 2510 is inserted into an inner tube 2514 extending through a sheath 2516 of an inserter disposed in the thoracic duct. In FIG. 34C, the stent 2510 is inserted in a compressed or unexpanded configuration. The stent 2510 is inserted over a guidewire 2518 extending through the inner tube 2514, as also shown in FIG. 34C. After the stent 2510 is inserted, the sheath 2516 can be retrieved by a user (e.g., any medical personnel) while holding the inner tube 2514 in place, as shown in FIG. 34D, to thus cause the stent 2510 to move to an expanded configuration to thereby alleviate the ostial valve closure by enabling the valve to release the lymph fluid. The guidewire 2518 and the inner tube 2514 may then be removed.

The pump 2108 can be implanted in a subcutaneous pocket created for the pump 2108, which can help ensure that the pump 2108 has adequate space within the patient's body. In the exemplary embodiment (FIG. 30), the pump 2108 can be implanted adjacent the junction of the internal jugular vein of the patient and the left subclavian vein of the patient, where the patient's thoracic duct and lymphatic duct (e.g., the right lymphatic duct) drain. For patients at risk of developing edema, outflow pressure at the junction is typically highly elevated, e.g., to values greater than about 10 mmHg, over normal outflow pressure, e.g., about 5 mmHg. Providing the pump 2108 can help regulate fluid at the junction, it can help prevent edema from occurring. The pump 2108 can be configured to regulate the pressure at the junction to which it is adjacent to a safe, non-edemic level such as its normal level, e.g., about 5 mmHg, or within a range of about 2 to 6 mmHg. The pressure gradient that that pump 2108 discharges against is less than about 15 mmHg. This relatively low flow rate and this pressure gradient can allow the pump 2108 to function with a very low energy consumption (e.g., with a low drain on the battery 2120), can allow for a very small power source (e.g., a very small battery such as those used with pacemakers and implantable cardioverter-defibrillators (ICDs)), and/or can allow for the pump 2108 to be very small and thereby facilitate implantation thereof.

Figure 35:
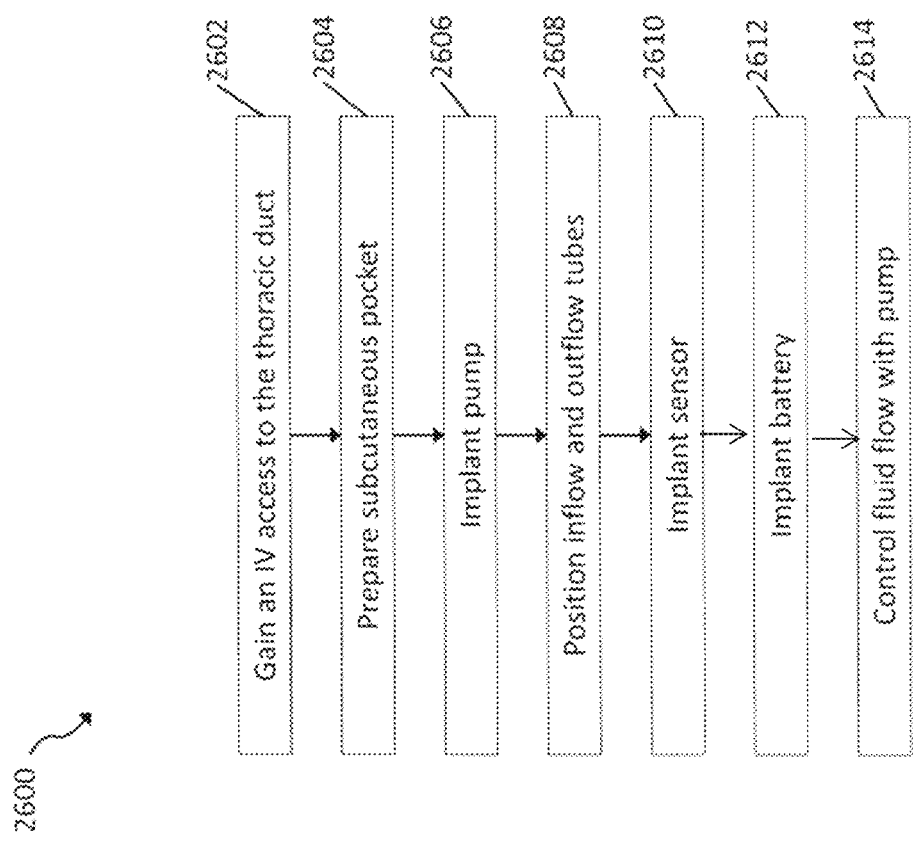
FIG. 35 is a flowchart of one embodiment of a method of treating edema using an implantable device in accordance with the described techniques.

FIG. 35 illustrates of one embodiment of a method 2600 of treating edema (e.g., fluid overload) using an implantable device (e.g., the implantable device 2100 in FIG. 30) in accordance with the described techniques. The method 2600 includes gaining an intravenous (IV) access to the thoracic duct, at block 2602. This can involve placing a guidewire towards the treatment site. The method 2600 further includes preparing, at block 2604, a subcutaneous pocket in a patient to seat the implantable pump (e.g., the pump 2108) therein. The subcutaneous pocket can be created, or, if such pocket already exists, it can be prepared for receiving the pump therein. Although not shown as a separate step, the method 2600 can also include subcutaneously creating a tunnel between the subcutaneous pocket and the IV access point.

The method 2600 can also include verifying a location of the patient's thoracic duct and/or the patient's lymphatic duct (e.g., the right lymphatic duct), which can help a surgeon and/or other medical professional involved in performing a surgical procedure that includes implanting, at block 2606, the pump verify that the pump, an inflow tube coupled to the pump, and/or an outflow tube coupled to the pump are implanted in the correct locations within the patient. If any one or more of the pump, the inflow tube, and the outflow tube is being implanted in one of the patient's thoracic duct and/or the patient's lymphatic duct, the location at least that one of the thoracic duct and lymphatic duct can be verified to help ensure that the pump, the inflow tube, and/or the outflow tube are implanted at the desired location(s). The verification can be performed in any of a variety of ways, as will be appreciated by a person skilled in the art, such as by using an imaging technique such as echo or fluoroscopy. The verification of the location of the patient's thoracic duct (and/or the patient's (right) lymphatic duct) and occur after the implantation of the pump such that the implanted location of the pump can be determined in view of the verification and adjusted if need be in view of the verification. Additionally or alternatively, the verification can be performed prior to the implantation of the pump.

After the pump is inserted into the subcutaneous pocket, the inflow and outflow tubes (e.g., the inflow and outflow tubes 2104, 2106 in FIG. 30) are positioned, at block 2608, in the patient such that their respective inflow and outflow openings are desirably positioned. The positioning of the inflow and outflow tubes can involve dilatation of the IV access, introduction of an introducer (e.g., a peel-away sheath) through the IV access, and insertion of the pump tubes through the introducer, and peel away sheath. After that, the inflow tube is removably anchored within the thoracic duct (e.g., using the attachment feature 2124 shown in FIG. 30), and the outflow tube is positioned within the vein, such as the jugular, subclavian, or innominate vein. The introducer can then be removed from the treatment site. The guidewire can be removed when it is no longer needed. The inflow and outflow tubes can be positioned (2608) in a variety of ways, as will be appreciated by a person skilled in the art, such as by using a central line procedure. Positioning tubes such as catheters is further described in U.S. application Ser. No. 14/625,930 entitled "System And Method For Treating Pulmonary Edema," filed Feb. 19, 2015. Other examples of a method of treating pulmonary edema using an implantable pump are described in U.S. application Ser. No. 14/726,715 entitled "Systems and Methods for Treating Pulmonary Edema," filed Jun. 1, 2015.

In some embodiments, as in the example of FIG. 35, one or more sensors (e.g., pressure sensors or other type(s) of sensors) can be implanted. It should be appreciated however the sensor in some embodiments is not implanted and is instead located outside the patient's body, and/or at least one sensor is implanted and at least one sensor is located outside the patient's body. As another variation, the sensor(s) may not need to be implanted separately, as it can be included with one or more other components of the implantable device.

The method 2600 also involves implanting a battery, at block 2612. It should be appreciated that the order of the steps shown in FIG. 35 is exemplary only, and that the battery can be implanted, e.g., before one or more sensors are implanted, or at any other time. Also, the order of the other steps is exemplary only. Before the battery is implanted, a location for it can be prepared within the patient's body.

After the pump is implanted (2606), the inflow and outflow tubes are positioned (2608), the sensor is optionally implanted (2610), and the battery is implanted (2612), the method includes controlling fluid flow with the pump of the implantable device, at block 2614. The control can generally occur as described above. In at least some embodiments, controlling of the pump can include continuously running the pump which can involve operating the pump in an idle mode and activating it in response to a trigger. The selection of one or more modes of operation of the pump can be done based on the patient's characteristics, a condition being treated, etc. The implantable device implanted into the patient's body as discussed above can then operate to alleviate chronic fluid overload conditions in the patient.

Figure 36:
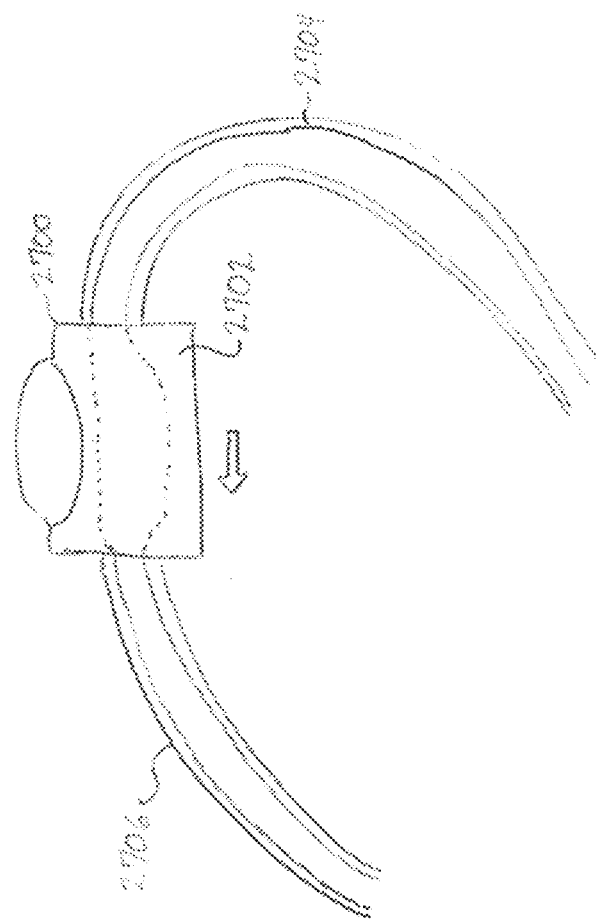
FIG. 36 is a schematic perspective view of an embodiment of an implantable port implanted in a patient's body.
Figure 37:
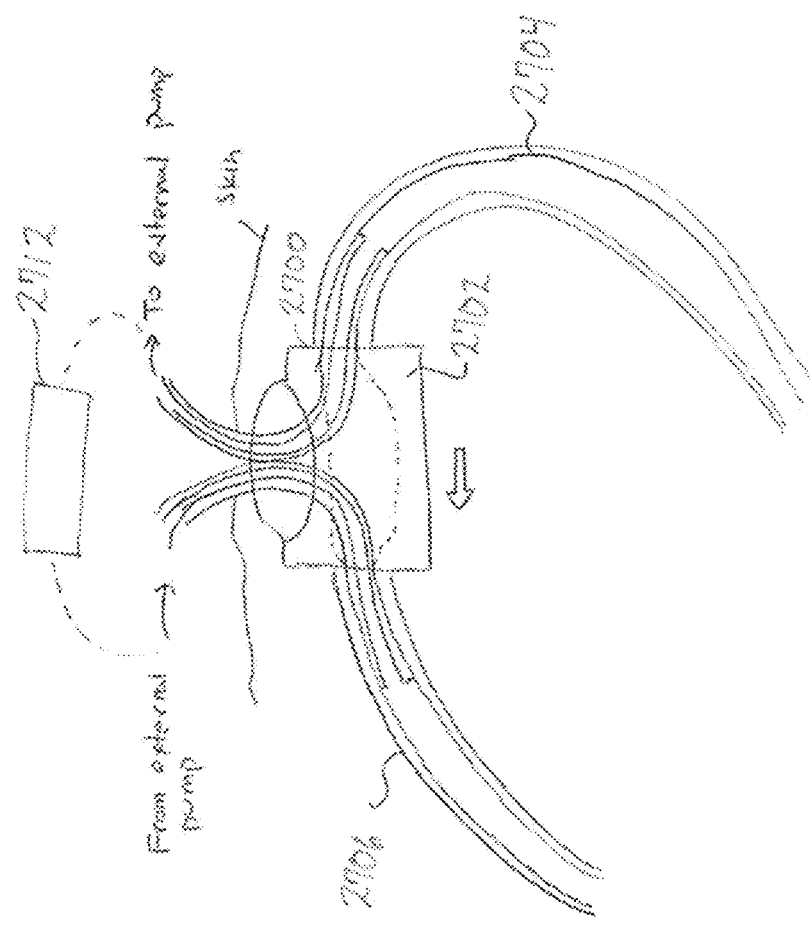
FIG. 37 is another perspective view of the implantable port of FIG. 36.

The described techniques discussed above relate to using an implantable device for treatment of chronic fluid overload, which can result in edema, such as pulmonary edema. In some circumstances, it may be desired to implant into a patient's body a system or device that can be used for a rapid alleviation of fluid overload. In such circumstances, the patient may not need to have the pump implanted in his/her body implanted for an extended period of time. At the same time, the patient may be at risk of developing fluid overload symptoms, and a rapid response can be required to address this condition. FIGS. 36 and 37 illustrate such alternative embodiment of an implantable device (which can have a single or dual chamber) 2700 having an access port 2702. The device 2700 with the port 2702 can be implanted subcutaneously, while a pump may not be implanted. The device 2700 can have or can be coupled to subcutaneously implanted inlet or inflow tube 2704 and outlet or outflow tube 2706, which can be similar to the inflow and outflow tubes 2104, 2106 (FIG. 30), respectively. Also, the inflow and outflow tubes 2704, 2706 can be placed within the patient's body similar to the tubes 2104, 2106 as shown in FIG. 30, or other can be placed in other locations. It should be appreciated that the implantable device 2700 and the tubes 2704, 2706 can have any other components and feature not shown herein for the sake of simplicity.

When a treatment (e.g., active pumping) is required, the tubes 2704, 2706 can be accessed via the port 2702 and can be used to allow the lymphatic fluids to flow more easily and thus reduce the edema. The port 2702 can be accessed externally using, e.g., a needle and it can be coupled to an external pump 2712, such as a peristaltic pump or other type of pump, as shown in FIG. 37. After the use, the tubes 2704, 2706 can be removed, whereas the port 2702 can remain implanted within the patient's body. If a subsequent treatment is required, a new set of inflow and outflow tubes can be introduced, the tubes can be connected to the external pump, and the treatment can be performed for a desired period of time, which can be from about 2 hours to about 2 days. The tubes can then be removed and, if still desired, the device 2700 with the port 2702 can remain implanted. In this way, the accessible system for multiple "on-demand" treatments is provided.

In the described embodiments, as mentioned above, a component or feature of any one of the embodiments can be used in combination with any other component or feature of another embodiment. Thus, if a certain feature is not described in a connection with one embodiment while it is shown in connection with another embodiment, it should be appreciated that the former embodiment may have that feature. Non-limiting examples of such features include various sensors, control elements, various types of lumens, fixation elements used to attached the catheter to the patient, etc.

It should be appreciated that the systems and methods disclosed herein can be used with a variety of surgical devices, including measuring devices, sensing devices, locator devices, insertion devices, etc. It should further be appreciated that the systems and methods described herein can have various modifications and variations. For example, any of the implantable catheter systems described herein can have first (e.g., distal) and second (e.g., proximal) selectively deployable restriction members having approximately the same or different diameters once deployed. The restriction members can be deployed in any suitable order. For example, in some embodiments, the distal restriction member can be deployed prior to deployment of the proximal restriction members. However, in some embodiments, the distal and proximal restriction members can be deployed such that the proximal restriction member is deployed first.

Furthermore, in some embodiments, the catheter system can be fully cannulated, such that a guide wire can be received therethrough. In some embodiments, a motor configured to rotate a drive shaft and thereby rotate an impeller coupled to the drive shaft is cannulated and can thus also receive a guidewire therethrough. As discussed above, each of the described catheter systems can have one or more pressure, or other types of sensors that can be disposed at suitable locations to monitor various parameters at a low pressure zone created in the patient's vein(s), as well as at other locations.

One skilled in the art will appreciate further features and advantages of the described subject matter based on the above-described embodiments. Accordingly, the present disclosure is not to be limited by what has been particularly shown and described, except as indicated by the appended claims. All publications and references cited herein are expressly incorporated herein by reference in their entirety.

What is claimed is:

1. A medical system for treating fluid overload, comprising:
    a catheter configured for at least partial placement within a vein of a patient, the catheter including
        an indwelling catheter tube having a lumen extending therethrough, the lumen configured to receive a drive shaft having a distal end thereof operatively coupled to an impeller,
        a first selectively deployable restriction member adjacent to the impeller, the impeller disposed at least partially distal to the first selectively deployable restriction member, the first selectively deployable restriction member disposed around a first portion of the catheter shaft;
        a second selectively deployable restriction member proximal to the first restriction member when the catheter is inside the vein; and
    a motor configured to rotate the drive shaft and thereby rotate the impeller coupled to the drive shaft.

2. The system of claim 1, further comprising a flow regulation component configured to direct a controlled volume of fluid from an upstream side of the second restriction member to a downstream side of the second restriction member, the flow regulation component having at least one opening configured to allow fluid flow therethrough.

3. The system of claim 2, wherein the flow regulation component is operatively coupled to the second restriction member.

4. The system of claim 2, wherein the flow regulation component is configured to direct fluid through a lumen defined by second restriction member.

5. The system of claim 1, further comprising a controller configured to control operation of the motor based on measurements of fluid pressure acquired by at least one pressure sensor located between the first and second restrictors.

6. The system of claim 1, wherein the first and second restriction members each include a selectively expandable element configured to be expanded radially.

7. The system of claim 1, wherein the catheter tube has at least one inflation lumen configured to deliver a fluid or gas to activate the first and second restriction members.

8. The system of claim 1, wherein the first restriction member has a first inner lumen that allows fluid to pass therethrough.

9. The system of claim 8, further comprising an impeller housing configured to encompass the impeller.

10. The system of claim 9, wherein the impeller housing comprises at least one opening at a distal end thereof such that fluid passing through the impeller housing from a proximal end thereof towards the distal end thereof can exit the impeller housing through the opening.

11. A medical system for treating fluid overload, comprising:
    a catheter configured for at least partial placement within a vein of a patient, the catheter including
        an indwelling catheter tube having a lumen extending therethrough, the lumen configured to receive a drive shaft having a distal end thereof operatively coupled to an impeller,
        a first selectively deployable restriction member adjacent to the impeller the first selectively deployable restriction member disposed around a first portion of the catheter shaft;
        a second selectively deployable restriction member proximal to the first restriction member when the catheter is inside the vein wherein the first restriction member has a first inner lumen comprising a shaft holder, the shaft holder being configured to receive the catheter tube thereto so as to maintain a position of the catheter tube; and
    a motor configured to rotate the drive shaft and thereby rotate the impeller coupled to the drive shaft.

12. A method of treating fluid overload, comprising:
    implanting a catheter within a vein of a patient, the catheter extending from a first position at one side of an outflow port of a duct to a second position at another side of the outflow port;
    creating a first restriction within the vein proximal to a distal region of the catheter;
    creating a second restriction within the vein proximal to a first restriction; and
    activating an impeller of the catheter so as to define a localized low pressure zone between the second and first restrictions and adjacent to the outflow port of the duct, at least a portion of the impeller located distal to the first restriction, the low pressure zone being created by causing fluid to pass from a proximal side of the second restriction to a distal side of the second restriction and from a proximal side of the first restriction to a distal side of the first restriction.

13. The method of claim 12, wherein creating the first restriction comprises deploying a first selectively expandable restrictor and creating the second restriction comprises deploying a second selectively expandable restrictor such that the fluid passes from the proximal side of the second restriction to the distal side of the first restriction by passing through an inner lumens of the first restrictor and towards the impeller.

14. The method of claim 12, wherein the vein includes at least one of an internal jugular vein and a subclavian vein.

15. The method of claim 12, wherein the duct includes one of a thoracic or a right lymphatic duct.

* * * * *